(12) United States Patent
Kato

(10) Patent No.: US 8,586,206 B2
(45) Date of Patent: Nov. 19, 2013

(54) AROMATIC AMINE DERIVATIVE AND ORGANIC ELECTROLUMINESCENCE DEVICE USING THE SAME

(75) Inventor: Tomoki Kato, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 306 days.

(21) Appl. No.: 12/923,008

(22) Filed: Aug. 27, 2010

(65) Prior Publication Data

US 2012/0001154 A1 Jan. 5, 2012

(30) Foreign Application Priority Data

Jun. 30, 2010 (JP) ................................. 2010-150091

(51) Int. Cl.
*H01L 51/54* (2006.01)
(52) U.S. Cl.
USPC ........... 428/690; 428/917; 313/504; 313/505; 313/506; 257/40; 257/E51.05; 257/E51.026; 257/E51.032; 564/46; 564/426; 564/434
(58) Field of Classification Search
USPC .................. 428/690, 917; 313/504, 505, 506; 564/426, 434, 26; 257/40, E51.05, 257/E51.026, E51.032
See application file for complete search history.

(56) References Cited

U.S. PATENT DOCUMENTS

| | | | | |
|---|---|---|---|---|
| 6,361,885 | B1 * | 3/2002 | Chou | 428/690 |
| 2004/0265630 | A1 * | 12/2004 | Suh et al. | 428/690 |

FOREIGN PATENT DOCUMENTS

| | | |
|---|---|---|
| JP | 02-052360 | 2/1990 |
| JP | 04-304465 A | 10/1992 |
| JP | 07-011246 A | 1/1995 |
| JP | 11-222590 | 8/1999 |
| JP | 2005-085658 | 3/2005 |
| JP | 2009-246097 * | 10/2009 |
| KR | 10-2010-075079 A | 7/2010 |
| WO | WO 2010/110553 A2 | 9/2010 |
| WO | WO 2010/131930 A2 | 11/2010 |
| WO | WO 2010/151083 A2 | 12/2010 |
| WO | WO 2011/055912 A1 | 5/2011 |

OTHER PUBLICATIONS

International Search Report issued Aug. 2, 2011, in PCT/JP2011/003721, 13 pages, with partial English translation, 2 pages.
Brandl et al., "An Efficient New Pyrimidine Synthesis—A Pathway to Octupoles," Journal fur praktische Chemie/Chemiker-Zeitung, 1996, 338(5):451-459.
Bushby et al., "Ferromagnetic spin-coupling 4,4"-through metaterphenyl: models for high-spin polymers," Journal of Materials Chemistry, 2007, 17(10):955-964.
Huang et al., "Synthesis and characterization of new fluorescent two-photon absorption chromophores," Journal of Materials Chemistry, 2006, 16(9):850-857.

* cited by examiner

*Primary Examiner* — Jennifer Chriss
*Assistant Examiner* — Gregory Clark
(74) *Attorney, Agent, or Firm* — Foley & Lardner LLP

(57) ABSTRACT

An aromatic amine derivative represented by the following formula (1), wherein at least one of $Ar^1$ to $Ar^3$ is represented by the following formula (2), wherein $X_1$ to $X_3$ are independently a nitrogen atom or $CR^2$, provided that two of $X_1$ to $X_3$ are a nitrogen atom and $X_1$ and $X_3$ are not simultaneously a nitrogen atom.

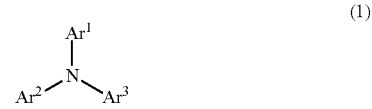

(1)

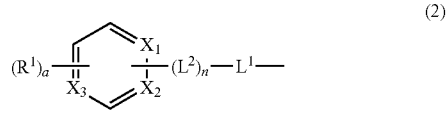

(2)

9 Claims, No Drawings

AROMATIC AMINE DERIVATIVE AND ORGANIC ELECTROLUMINESCENCE DEVICE USING THE SAME

TECHNICAL FIELD

The invention relates to an aromatic amine derivative and organic electroluminescence device using the same.

BACKGROUND ART

An organic electroluminescent device (organic EL device) is a promising solid-state emitting type inexpensive and large full-color display device, and has been extensively developed. In general, an organic EL device includes an emitting layer and a pair of opposing electrodes holding the emitting layer therebetween. When an electric field is applied between the electrodes, electrons are injected from the cathode and holes are injected from the anode. The electrons recombine with the holes in the emitting layer to produce an excited state, and energy is emitted as light when the excited state returns to the ground state.

Early organic EL devices are insufficient in driving voltage, luminous efficiency and durability, and various technical improvements have been made for the problems.

The improvements of luminous efficiency and lifetime of the organic EL device are important subjects which lead to a low power consumption of display and improvement of durability. Therefore, further improvement is required.

To solve the problems, Patent Document 1 discloses a triarylamine derivative which can be used as a hole-transporting material and emitting material. This triarylamine derivative has an electron-trapping function. Patent Document 2 discloses a compound having a specific structure in which a diarylamine or nitrogen-containing heterocyclic group bonds via a biphenylene linking group.

Patent Document 3 tries to improve device performance using a compound with a heterocyclic group (pyrimidine, triazine and the like) containing at least two nitrogen atoms at certain positions. Patent Document 4 discloses a compound having a pyrimidine skeleton for an electrophotographic photoreceptor.

| | |
|---|---|
| [Patent Document 1] | JP-A-H11-222590 |
| [Patent Document 2] | JP-A-2005-085658 |
| [Patent Document 3] | JP-A-2009-246097 |
| [Patent Document 4] | JP-A-H02-052360 |

DISCLOSURE OF THE INVENTION

An object of the invention is to provide an aromatic amine derivative which is useful for a high luminous efficiency and long lifetime of an organic EL device.

According to the invention, the following aromatic amine derivative can be provided.

1. An aromatic amine derivative represented by the following formula (1):

wherein at least one of $Ar^1$ to $Ar^3$ is represented by the following formula (2):

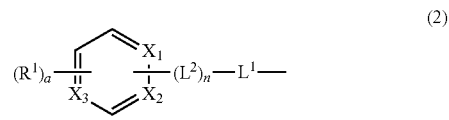

wherein $X_1$ to $X_3$ are independently a nitrogen atom or $CR^2$, provided that two of $X_1$ to $X_3$ are a nitrogen atom and $X_1$ and $X_3$ are not simultaneously a nitrogen atom, $R^1$ is a linear or branched alkyl group having 1 to 10 carbon atoms, a cycloalkyl group having 3 to 10 carbon atoms that form a ring (hereinafter referred to as ring carbon atoms), a substituted or unsubstituted silyl group, an aryl group having 6 to 50 ring carbon atoms, a heteroaryl group having 5 to 50 atoms that form a ring (hereinafter referred to as ring atoms), a halogen atom or a cyano group, $R^2$ is a hydrogen atom or a group represented by $R^1$, a is an integer of 1 to 2 and n is an integer of 0 to 3, $L^1$ is a substituted or unsubstituted arylene group having 6 to 50 ring carbon atoms, $L^2$ is a substituted or unsubstituted arylene group having 6 to 50 ring carbon atoms, or a substituted or unsubstituted heteroarylene group having 5 to 50 ring atoms, $Ar^1$ to $Ar^3$ that are not the group of formula (2) are independently a substituted or unsubstituted aryl group having 6 to 50 ring carbon atoms, when $L^1$, $L^2$ and $Ar^1$ to $Ar^3$ that are not the group of formula (2) have a substituent, the substitutes are independently a linear or branched alkyl group having 1 to 10 carbon atoms, a cycloalkyl group having 3 to 10 ring carbon atoms, a substituted or unsubstituted silyl group, an aryl group having 6 to 14 ring carbon atoms, a heteroaryl group having 5 to 20 ring atoms, a halogen atom or a cyano group, when two or more of $Ar^1$ to $Ar^3$ are the groups of formula (2), the groups of formula (2) may be the same or different, when a is 2, $R^1$s may be the same or different, and when n is 2 or more, $L^2$s may be the same or different.

2. The aromatic amine derivative according to 1, wherein $L^1$ is any one of a substituted or unsubstituted phenylene group, naphthyl group, biphenylene group and fluorenylene group.

3. The aromatic amine derivative according to 1 or 2, wherein the at most two of $Ar^1$ to $Ar^3$ that are not the group of formula (2) are independently any one of a phenyl group, biphenyl group, terphenyl group and 9,9-dimethylfluorenyl group.

4. The aromatic amine derivative represented by any one of the following formulas (6) to (9):

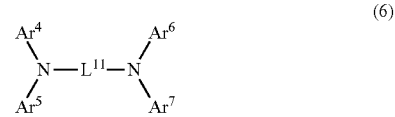

-continued

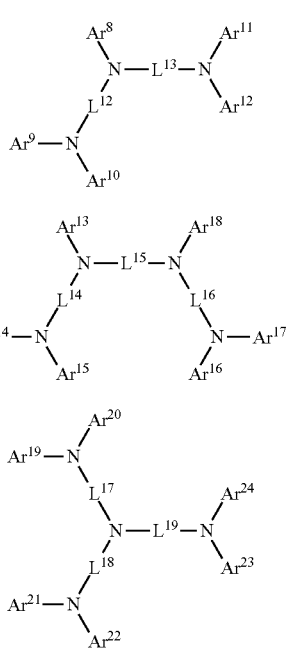

wherein at least one of $Ar^4$ to $Ar^7$ is represented by the following formula (2), at least one of $Ar^8$ to $Ar^{12}$ is represented by the following formula (2), at least one of $Ar^{13}$ to $Ar^{18}$ is represented by the following formula (2), and at least one of $Ar^{19}$ to $Ar^{24}$ is represented by the following formula (2),

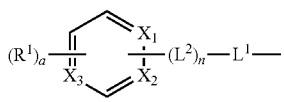

wherein $X_1$ to $X_3$ are independently a nitrogen atom or $CR^2$, provided that two of $X_1$ to $X_3$ are a nitrogen atom and $X_1$ and $X_3$ are not simultaneously a nitrogen atom, $R^1$ is a linear or branched alkyl group having 1 to 10 carbon atoms, a cycloalkyl group having 3 to 10 ring carbon atoms, a substituted or unsubstituted silyl group, an aryl group having 6 to 50 ring carbon atoms, a heteroaryl group having 5 to 50 ring atoms, a halogen atom or a cyano group, $R^2$ is a hydrogen atom or a group represented by $R^1$, a is an integer of 1 to 2 and n is an integer of 0 to 3, $L^1$ is a substituted or unsubstituted arylene group having 6 to 50 ring carbon atoms, $L^2$ is a substituted or unsubstituted arylene group having 6 to 50 ring carbon atoms, or a substituted or unsubstituted heteroarylene group having 5 to 50 ring atoms, the substituents of $L^1$ and $L^2$ are independently a linear or branched alkyl group having 1 to 10 carbon atoms, a cycloalkyl group having 3 to 10 ring carbon atoms, a substituted or unsubstituted silyl group, an aryl group having 6 to 14 ring carbon atoms, a halogen atom or a cyano group, $Ar^4$ to $Ar^{24}$ that are not the group of formula (2) are independently a substituted or unsubstituted aryl group having 6 to 50 ring carbon atoms, $L^{11}$ to $L^{19}$ are independently a substituted or unsubstituted arylene group having 6 to 50 ring carbon atoms, when $Ar^4$ to $Ar^{24}$ that are not the group of formula (2) and $L^{11}$ to $L^{19}$ have a substituent, the substitutes are independently a linear or branched alkyl group having 1 to 10 carbon atoms, a cycloalkyl group having 3 to 10 ring carbon atoms, a substituted or unsubstituted silyl group, an aryl group having 6 to 14 ring carbon atoms, a heteroaryl group having 5 to 20 ring atoms, a halogen atom or a cyano group, when two or more of $Ar^4$ to $Ar^7$, $Ar^8$ to $Ar^{12}$, $Ar^{13}$ to $Ar^{18}$, or $Ar^{19}$ to $Ar^{24}$ are the groups of formula (2), the groups of formula (2) may be the same or different, when a is 2, $R^1$s may be the same or different, and when n is 2 or more, $L^2$s may be the same or different.

5. The aromatic amine derivative according to 4, wherein $L^{11}$ to $L^{19}$ are independently any one of a substituted or unsubstituted phenylene group, biphenylene group and fluorenylene group.

6. The aromatic amine derivative according to 4 or 5, wherein the groups of $Ar^4$ to $Ar^{24}$ that are not the group of formula (2) are independently any one of a phenyl group, naphthyl group, biphenyl group, terphenyl group and 9,9-dimethylfluorenyl group.

7. The aromatic amine derivative according to any one of claims 1 to 6, which is a material for an organic electroluminescence device.

8. The aromatic amine derivative according to any one of claims 1 to 6, which is a hole transporting material for an organic electroluminescence device.

9. The aromatic amine derivative according to any one of claims 1 to 6, which is a phosphorescent host material for an organic electroluminescence device.

10. An organic electroluminescence device comprising:

a cathode, an anode, and one or more organic thin films including an emitting layer therebetween, wherein at least one layer of the organic thin films comprises the aromatic amine derivative according to any one of claims 1 to 6.

11. The organic electroluminescence device according to 10, wherein at least one layer of the organic thin films is a hole transporting layer and/or hole injecting layer, and the aromatic amine derivative is contained in at least one of the hole transporting layer and/or hole injecting layer.

12. The organic electroluminescence device according to 11, wherein the aromatic amine derivative is contained in at least one of the hole transporting layer and/or hole injecting layer as the main component.

13. The organic electroluminescence device according to 11 or 12, wherein a layer contacting the anode of the hole injecting layer and/or hole transporting layer comprises an acceptor material.

14. The organic electroluminescence device according to 10, wherein the aromatic amine derivative is contained in at least one layer of the emitting layers.

15. The organic electroluminescence device according to 10, wherein the aromatic amine derivative and a phosphorescent dopant are contained in at least one emitting layer.

According to the invention, an aromatic amine derivative which is useful for a high luminous efficiency and long lifetime of an organic EL device can be provided.

BEST MODE FOR CARRYING OUT THE INVENTION

The aromatic amine derivative of the invention is shown by the following formula (1):

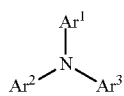
(1)

wherein at least one (preferably one) of $Ar^1$ to $Ar^3$ is shown by the following formula (2).

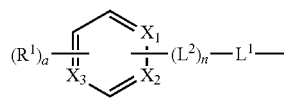
(2)

In the formula (2), $X_1$ to $X_3$ are independently a nitrogen atom or $CR^2$, provided that two of $X_1$ to $X_3$ are a nitrogen atom and $X_1$ and $X_3$ are not simultaneously a nitrogen atom.

$R^1$ is a linear or branched alkyl group having 1 to 10 carbon atoms, a cycloalkyl group having 3 to 10 ring carbon atoms, a substituted or unsubstituted silyl group, an aryl group having 6 to 50 ring carbon atoms, a heteroaryl group having 5 to 50 ring atoms, a halogen atom or a cyano group.

$R^2$ is a hydrogen atom or a group represented by $R^1$.

$(R^1)_a$— and $-L^1-(L^2)_n-$ are bonded to carbon atoms other than $X_1$ to $X_3$ in the six-membered ring, respectively.

a is an integer of 1 or 2. When the six-membered ring of the formula (2) is a pyridazine skelton or a pyrimidine skelton, a is preferably 1.

n is an integer of 0 or 3. n is preferably 0 or 1, and more preferably 0.

$L^1$ is a substituted or unsubstituted arylene group having 6 to 50 ring carbon atoms.

$L^2$ is a substituted or unsubstituted arylene group having 6 to 50 ring carbon atoms, or a substituted or unsubstituted heteroarylene group having 5 to 50 ring atoms.

$Ar^1$ to $Ar^3$ that are not the group of formula (2) are independently a substituted or unsubstituted aryl group having 6 to 50 ring carbon atoms, and preferably independently a phenyl group, a naphthyl group, a biphenyl group, a terphenyl group or 9,9-dimethylfluorenyl group.

When $L^1$, $L^2$ and $Ar^1$ to $Ar^3$ that are not the group of formula (2) have a substituent, the substitutes are independently a linear or branched alkyl group having 1 to 10 carbon atoms, a cycloalkyl group having 3 to 10 ring carbon atoms, a substituted or unsubstituted silyl group, an aryl group having 6 to 14 ring carbon atoms, a heteroaryl group having 5 to 20 ring atoms, a halogen atom or a cyano group.

When two or more of $Ar^1$ to $Ar^3$ are the groups of formula (2), the groups of formula (2) may be the same or different.

When a is 2, $R^1$s may be the same or different.

When n is 2 or more, $L^2$s may be the same or different.

$L^1$ is preferably a substituted or unsubstituted arylene group having 6 to 30 ring carbon atoms, more preferably a substituted or unsubstituted arylene group having 6 to 20 ring carbon atoms, and particularly preferably any one of a substituted or unsubstituted phenylene group, biphenylene group and fluorenylene group.

As specific examples of $L^1$, groups shown by the following structural formulas can be given, but $L^1$ is not limited thereto.

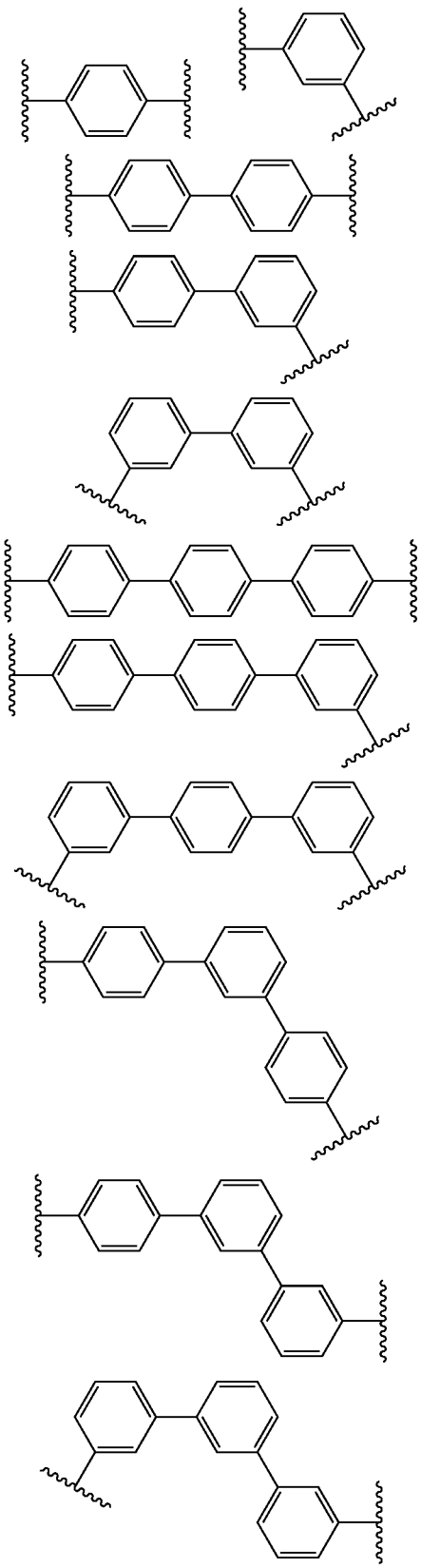

-continued

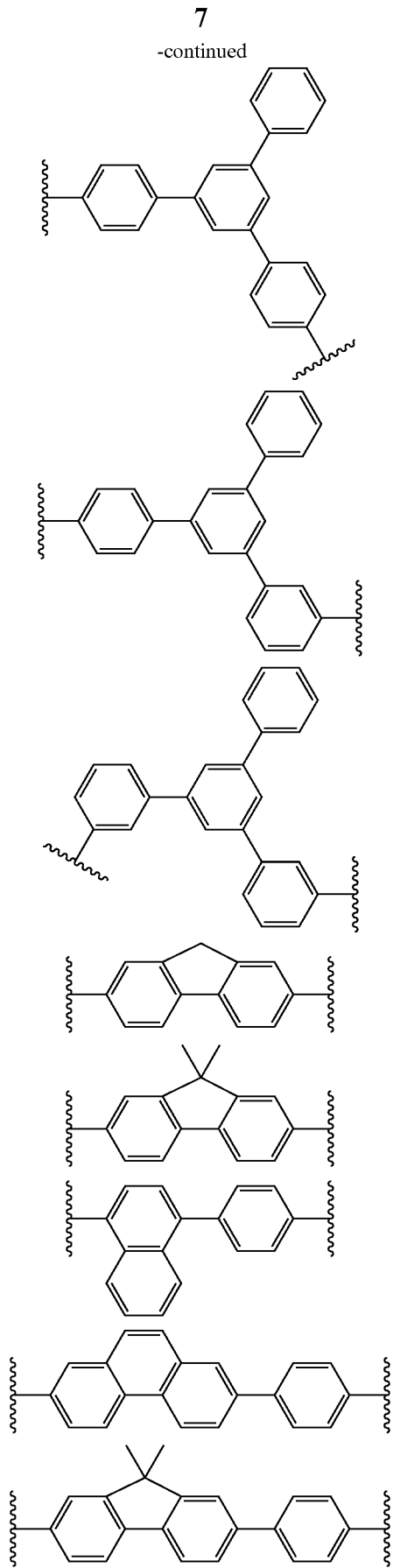

-continued

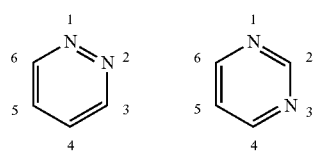

$L^2$ is preferably a substituted or unsubstituted arylene group having 6 to 30 ring carbon atoms or a substituted or unsubstituted divalent heteroarylene group having 5 to 30 ring atoms, more preferably a substituted or unsubstituted arylene group having 6 to 20 ring carbon atoms or a substituted or unsubstituted heteroarylene group having 5 to 20 ring atoms, and particularly preferably any one of a substituted or unsubstituted phenylene group, biphenylene group, fluorenylene group, carbazolyl group, dibenzofuranyl group and dibenzothiophenyl group.

As specific examples of $L^2$, the same groups as exemplified as ones of $L^1$ can be given, but $L^2$ is not limited thereto.

In the aromatic amine derivative (1) of the invention, the six-membered ring of formula (2) containing $X_1$ to $X_3$ functions as an electron-transporting part, and the triarylamine part functions as a hole-transporting part. Having such a structure, the aromatic amine derivative (1) can transport both holes and electrons.

Since the six-membered ring of formula (2) has two nitrogen atoms, the compound is high in electron-attracting effect, and it does not attract electrons excessively and the effect is not too weak, which is preferable.

The following compounds (pyridazine and pyrimidine from the left) can be given as the six-membered ring of the formula (2).

In general, a compound is required to be carrier-resistant when it is used as an organic EL material. Thus in the compound of the invention, the six-membered ring containing $X_1$ to $X_3$ preferably has a substituent.

For example, if the six-membered ring of formula (2) is pyridazine shown above, it is preferable that pyridazine have a substituent at one or more of positions 3 and 6; if the six-membered ring of formula (2) is pyrimidine, it is preferable that pyrimidine have a substituent at one or more of positions 2, 4 and 6.

$R_1$ and $R_2$ are preferably an electrochemically stable substituent, and examples thereof include an aryl group having 6 to 50 ring carbon atoms, heterocyclic group having 5 to 50 ring atoms, fluorine atom and cyano group.

These preferable substituents tend to enhance the electrochemical stability and charge-resistance of the amine compound, leading to the long life time.

The inventor considers as folllows.

The six-membered ring of formula (2) containing $X_1$ to $X_3$ decide the LUMO level and electron distribution area in LUMO of compound (1). The compound of the invention has a deep LUMO level in comparison with conventional compounds, such as NPD, which do not have an electron-transporting part. In addition, in the compound of the invention, the electron distribution area of HOMO and that of LUMO are clearly separated, and therefore the energy gap (Eg) thereof increases.

If the electron distribution areas of HOMO and LUMO are clearly separated, when the compound is reduced, electrons preferentially enter the LUMO level and the stability of the compound increases. If the electron distribution areas of HOMO and LUMO are clearly separated, the compound is stable since electrons do not enter the HOMO level.

In general, to be a hole-transporting part (high in hole resistance), a compound is required to be high in resistance under oxidative conditions in which holes are generated.

If alkyl or heteroaryl bonds directly to the amine, the compound is not resistant to oxidization, since the electron density becomes high. In order to increase the resistance, the amine needed to be directly connected with an aryl group which has a neutral electron density. Thus, the triarylamine part of the above aromatic amine derivative can be a hole-transporting part.

In addition, if an aryl group which directly connects to the amine is substituted with alkyl or heteroaryl, the compound is resistant since the electron density does not become high.

As mentioned above, the inventor considers that when the compound is used in a hole-transporting layer or hole-injecting layer, the compound can prevent the layers from deterioration since the aromatic amine derivative of the invention is carrier-resistant, and therefore the lifetime of the device is improved. Due to the wide gap, triplet excitons are trapped in an emitting layer, they collide with each other, and singlet excitons are generated to emit light (TTF effect), thereby improving the efficiency.

The aromatic amine derivative of the invention can be used in a carrier blocking layer for a white light emitting device since the compound can transport both holes and electrons. The high carrier transporting properties of the device enable low-voltage drive and the wide gap enables the adjustment of carrier balance, leading in a high emitting efficiency and long life time.

The aromatic amine derivative of the invention can be used as a phosphorescent host and the like. In this case, an emitting layer preferably contains the aromatic amine derivative of the invention and a phosphorescent dopant described later. Since the compound is superior in carrier balance, the recombination probability and efficiency are increased. In addition, since an emitting area does not lean to a hole-transporting layer, the deterioration of the hole-transporting layer can be prevented, and the lifetime lengthens.

Furthermore, the aromatic amine derivative of the invention is shown by any one of the following formulas (6) to (9).

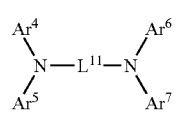

(6)

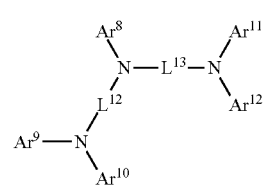

(7)

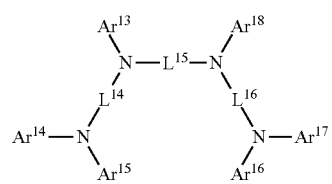

(8)

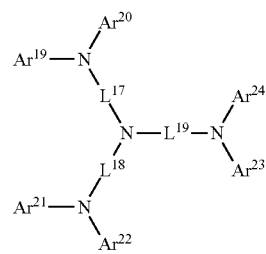

(9)

At least one of $Ar^4$ to $Ar^7$, at least one of $Ar^8$ to $Ar^{12}$, at least one of $Ar^{13}$ to $Ar^{18}$ and at least one of $Ar^{19}$ to $Ar^{24}$ are represented by the above-mentioned formula (2). The "at least one" thereof is preferably one or two.

$Ar^4$ to $Ar^{24}$ that are not the group of formula (2) are independently a substituted or unsubstituted aryl group having 6 to 50 ring carbon atoms. Preferably, they are independently any one of a phenyl group, naphthyl group, biphenyl group, terphenyl group and 9,9-dimethylfluorenyl group.

$L^{11}$ to $L^{19}$ are independently a substituted or unsubstituted arylene group having 6 to 50 ring carbon atoms. Preferably, they are independently any one of a substituted or unsubstituted phenylene group, biphenylene group, and fluorenylene group. The same groups as ones of $L^1$ of the formula (1) can be exemplified. Because they have no hetero ring (heteroarylene group) between two nitrogen atoms, preferably the hole mobility thereof does not increase and the driving voltage thereof does not excessively increase.

When $Ar^4$ to $Ar^{24}$ that are not the group of formula (2) and $L^{11}$ to $L^{19}$ have a substituent (this means "a substituent" of "substituted or unsubstituted" as mentioned above), the substitutes are independently a linear or branched alkyl group having 1 to 10 carbon atoms, a cycloalkyl group having 3 to 10 ring carbon atoms, a substituted or unsubstituted silyl group, an aryl group having 6 to 14 ring carbon atoms, a heteroaryl group having 5 to 20 ring atoms, a halogen atom or a cyano group.

In the specification, the "ring carbon atoms" mean carbon atoms that form a saturated ring, unsaturated ring or aromatic ring. The "ring atoms" mean carbon atoms and hetero atoms that form a ring including a saturated ring, unsaturated ring or aromatic ring.

The "unsubstituted" means that a group is substituted with a hydrogen atom and the hydrogen atom of the invention includes light hydrogen, deuterium and tritium.

The groups shown by $R^1$, $R^2$, $L^1$, $L^2$, $L^{11}$ to $L^{19}$ and $Ar^1$ to $Ar^{24}$ and the substitutents thereof in the formulas (1), (2) and (6) to (9) will be described hereinafter.

Examples of the alkyl group include methyl, ethyl, propyl, isopropyl, n-butyl, s-butyl, isobutyl, t-butyl, n-pentyl, n-hexyl, n-heptyl and n-octyl.

The group preferably has 1 to 10 carbon atoms and more preferably 1 to 6 carbon atoms. Particulary, methyl, ethyl, propyl, isopropyl, n-butyl, s-butyl, isobutyl, t-butyl, n-pentyl and n-hexyl are preferable.

Examples of the cycloalkyl group include cyclopropyl, cyclobutyl, cyclopentyl, cyclohexyl, adamantyl and norbornyl. The group has preferably 3 to 10 ring carbon atoms and more preferably 3 to 8 ring carbon atoms.

Examples of the substituted silyl group include a alkylsilyl group having 3 to 30 carbon atoms (for example, a trialkylsilyl group having 3 to 10 carbon atoms), a arylsilyl group having 8 to 30 ring carbon atoms (for example, triarylsilyl group having 18 to 30 ring carbon atoms), and an alkylarylsilyl group having 8 to 15 carbon atoms (the aryl part has 6 to 14 ring carbon atoms). Specific examples include trimethylsilyl, triethylsilyl, t-butyldimethylsilyl, vinyldimethylsilyl, propyldimethylsilyl, triisopropylsilyl and triphenylsilyl.

Examples of the aryl group include phenyl, 1-naphthyl, 2-naphthyl, 1-anthryl, 2-anthryl, 9-anthryl, 1-phenanthryl, 2-phenanthryl, 3-phenanthryl, 4-phenanthryl, 9-phenanthryl, naphthacenyl, pyrenyl, chrysenyl, benzo[c]phenanthryl, benzo[g]chrysenyl, triphenylenyl, 1-fluorenyl, 2-fluorenyl, 3-fluorenyl, 4-fluorenyl, 9-fluorenyl, benzofluorenyl, dibenzofluorenyl, 2-biphenylyl, 3-biphenylyl, 4-biphenylyl, terphenyl and fluoranthenyl.

As examples of the arylene group, divalent groups corresponding to the above-mentioned aryl groups can be given.

The above-mentioned aryl group preferably has 6 to 20 ring carbon atoms and more preferably 6 to 12 ring carbon atoms. Phenyl, biphenyl, tolyl, xylyl and 1-naphthyl are particulaly preferable among the above-mentioned aryl groups.

Examples of the heteroaryl group include pyrrolyl, pyrazinyl, pyridinyl, indolyl, isoindolyl, imidazolyl, furyl, benzofuranyl, isobenzofuranyl, 1-dibenzofuranyl, 2-dibenzofuranyl, 3-dibenzofuranyl, 4-dibenzofuranyl. 1-dibenzothiophenyl, 2-dibenzothiophenyl, 3-dibenzothiophenyl, 4-dibenzothiophenyl, quinolyl, isoquinolyl, quinoxalinyl, 1-carbazolyl, 2-carbazolyl, 3-carbazolyl, 4-carbazolyl, 9-carbazolyl, phenantridinyl, acridinyl, phenanthrolinyl, phenazinyl, phenothiazinyl, phenoxazinyl, oxazolyl, oxadiazolyl, furazanyl, thienyl and benzothiophenyl.

The above-mentioned heteroaryl group preferably has 5 to 20 ring atoms and more preferably 5 to 14 ring atoms.

1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-carbazolyl, 2-carbazolyl, 3-carbazolyl, 4-carbazolyl and 9-carbazolyl are preferable.

As the halogen atom, fluorine, chlorine, bromine and iodine can be given. Fluorine is preferable.

The aromatic amine derivatives of the above formulas (6) to (9) also have an electron-transporting position and hole-transporting position like the aromatic amine derivative of the formula (1), and preferably have carrier resistance properties and the same advantages.

Examples of the above aromatic amine derivatives (1) and (6) to (9) of the invention are given below.

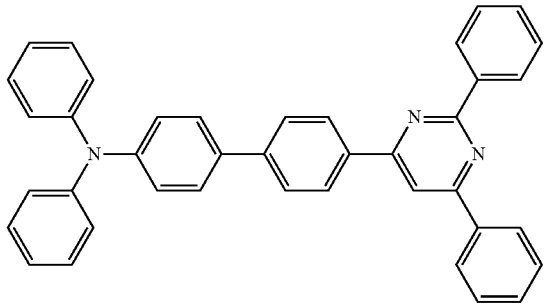

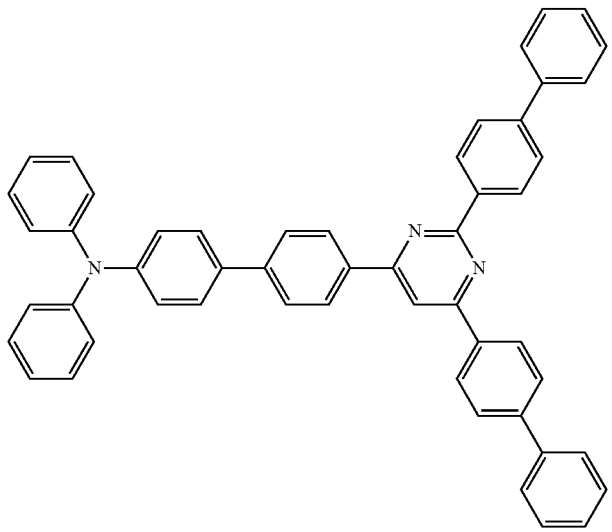

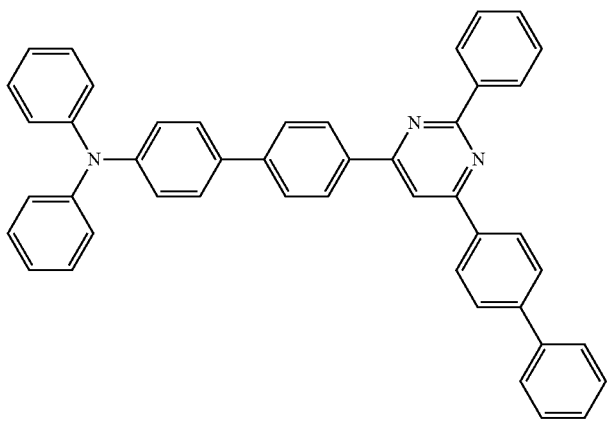

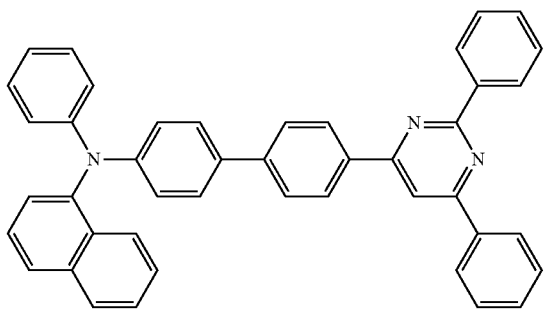

-continued
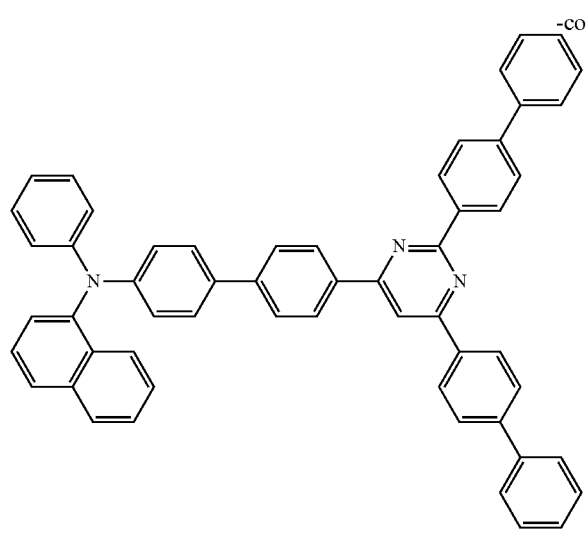
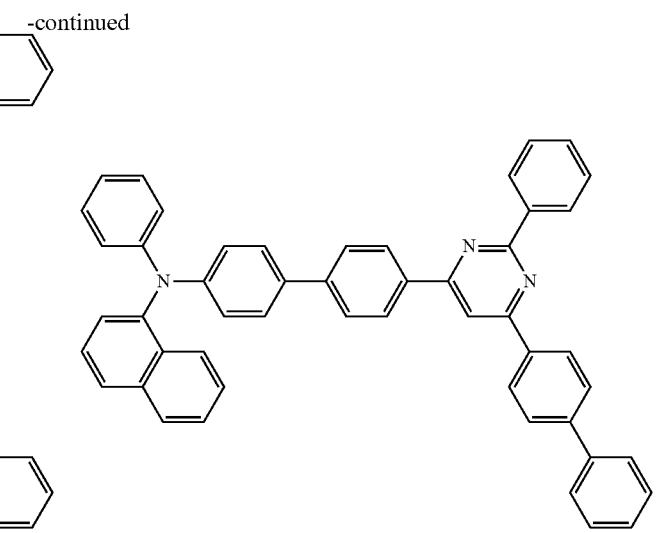
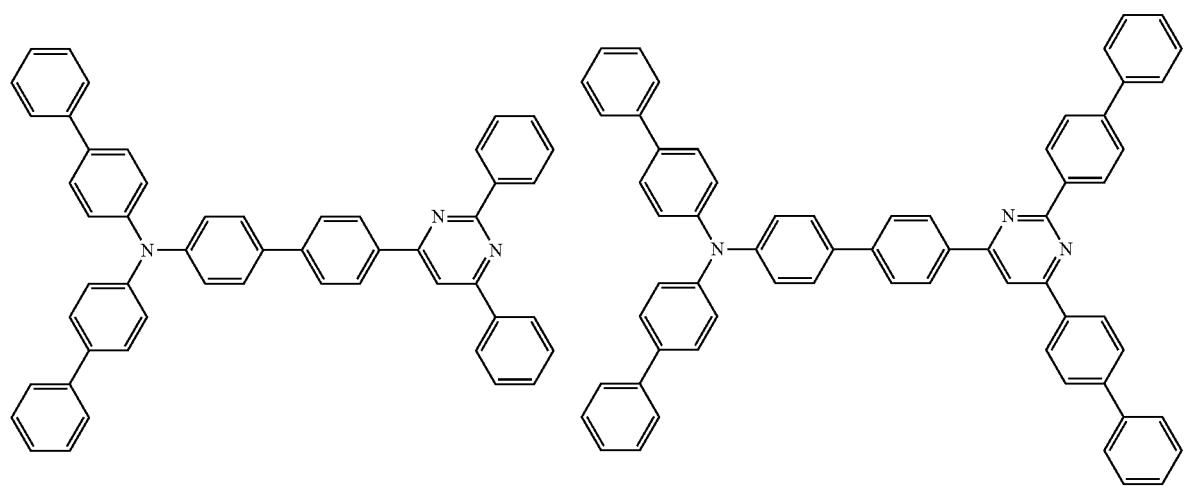
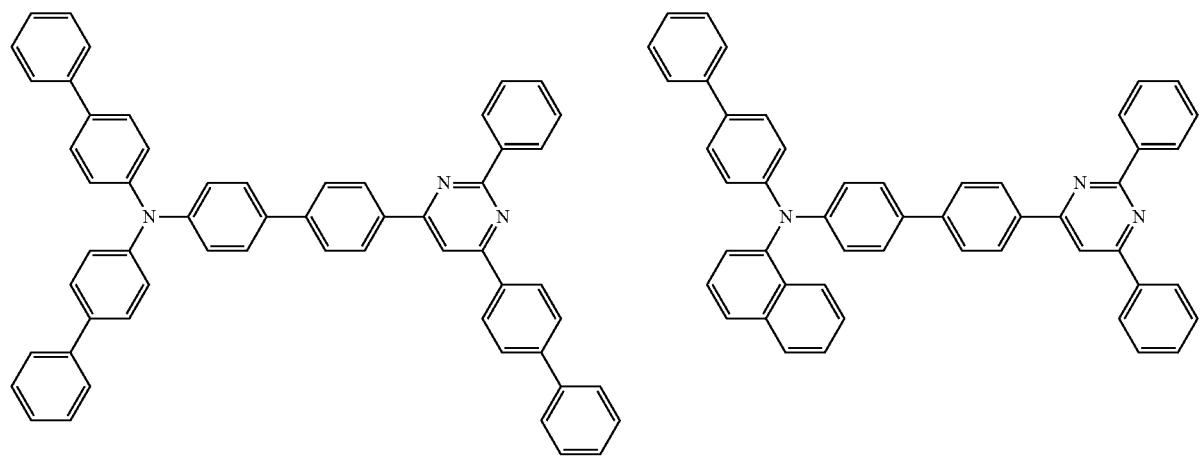

-continued
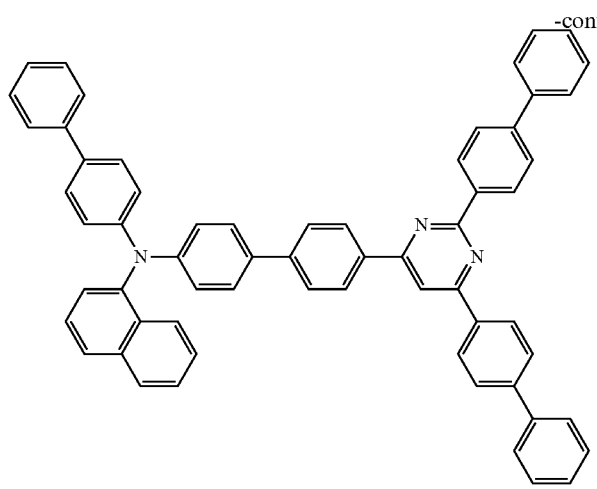
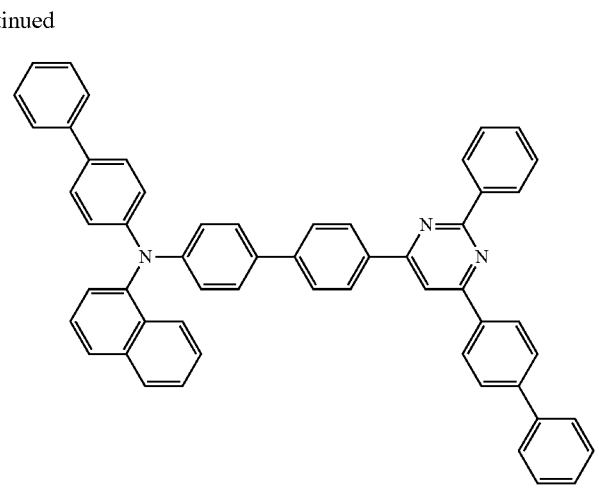
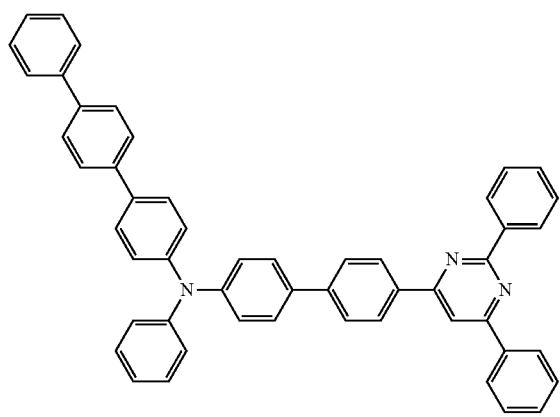
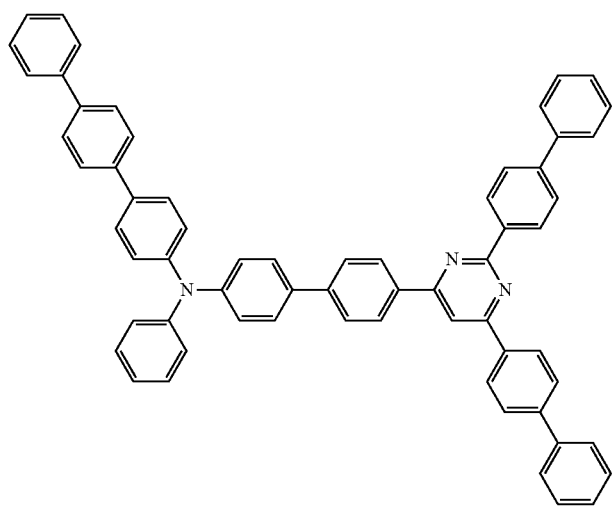
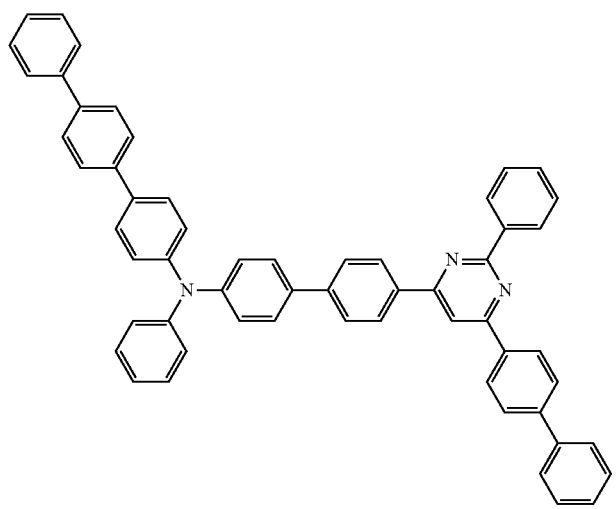
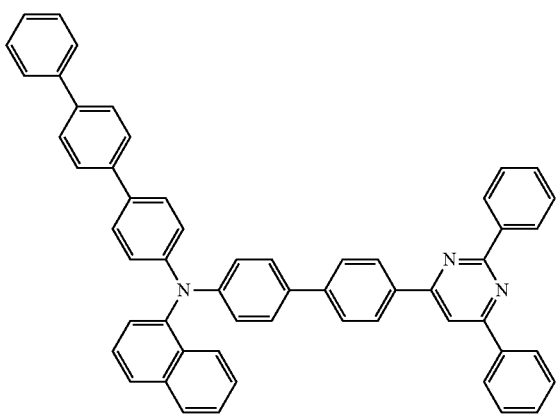

-continued
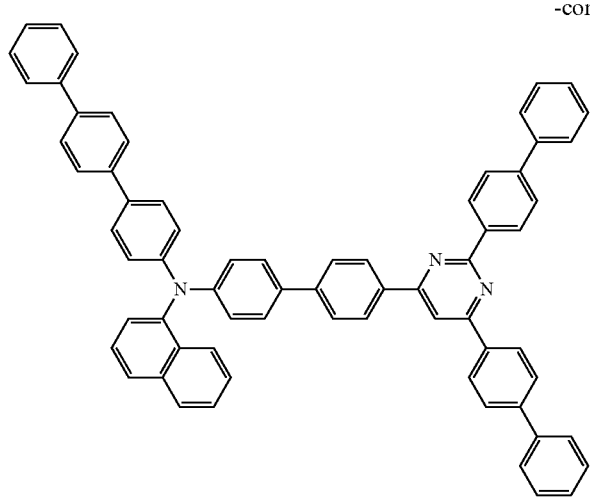
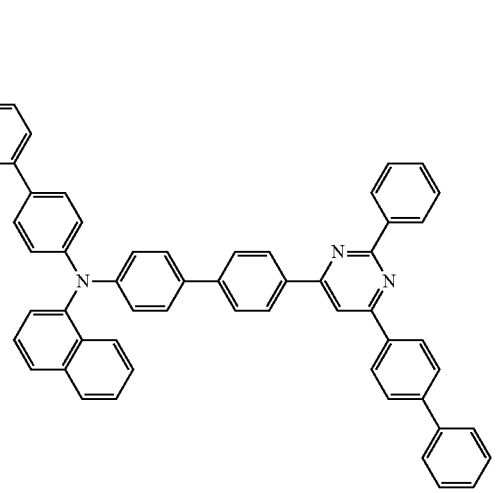
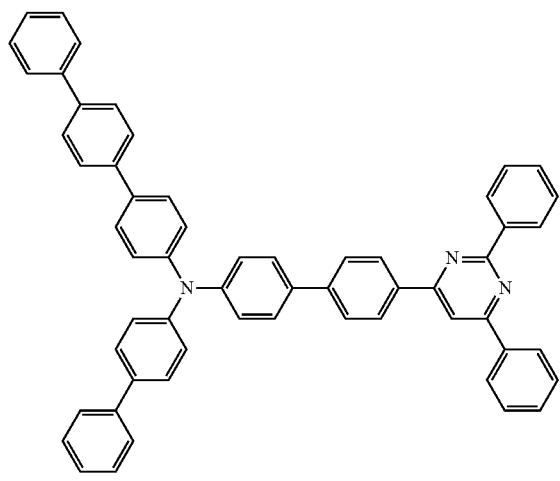
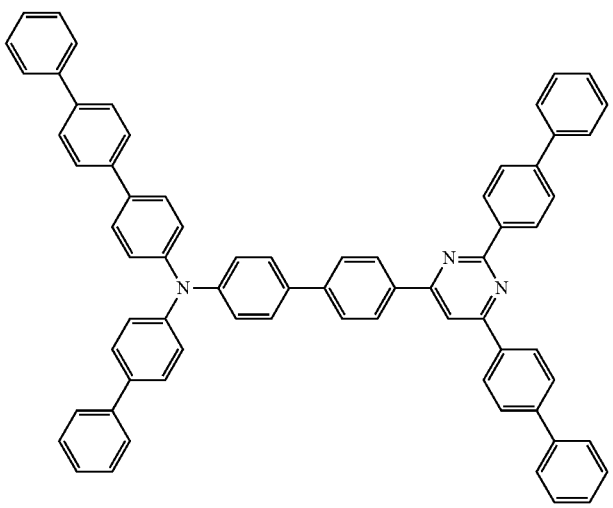
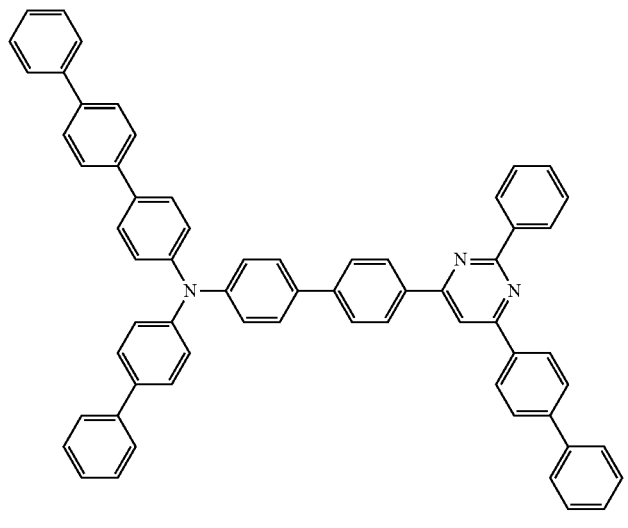
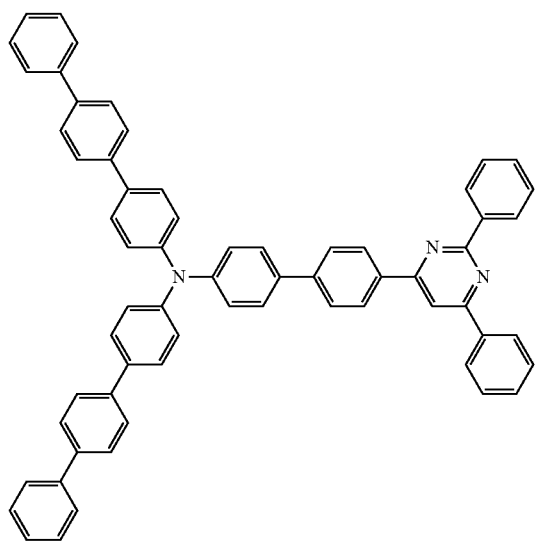

-continued
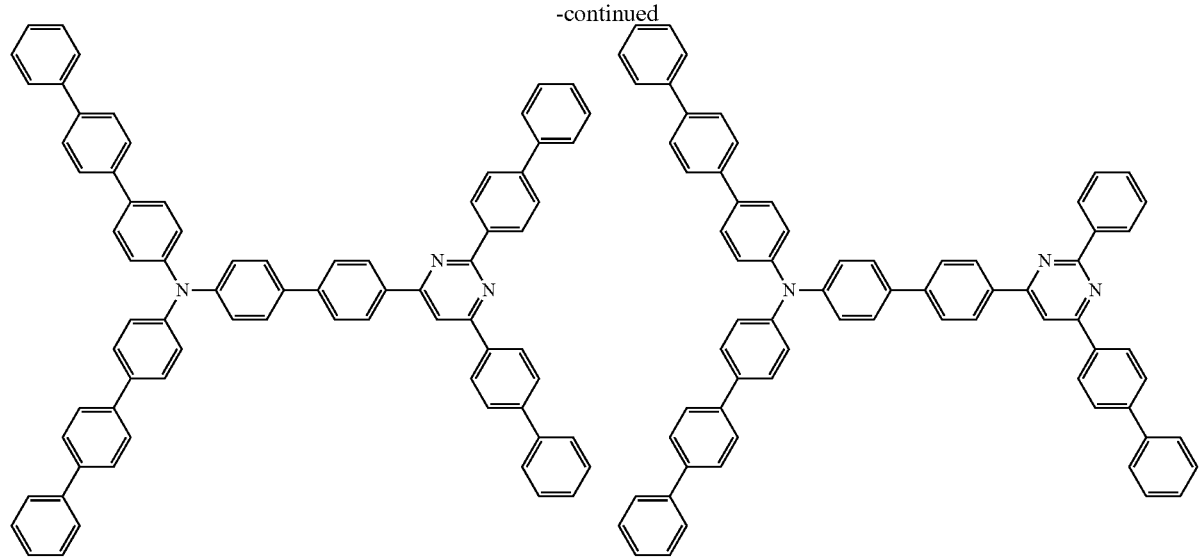
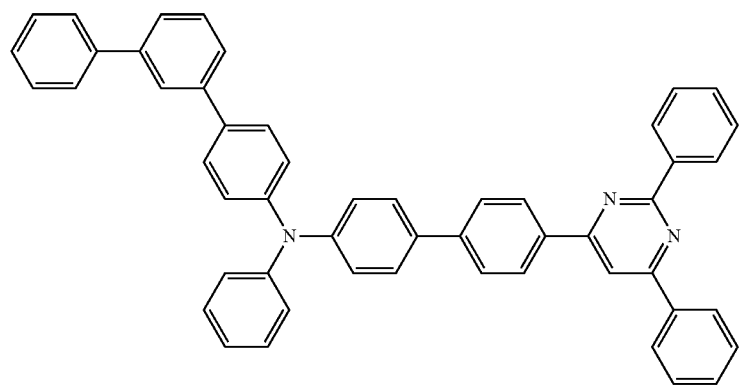
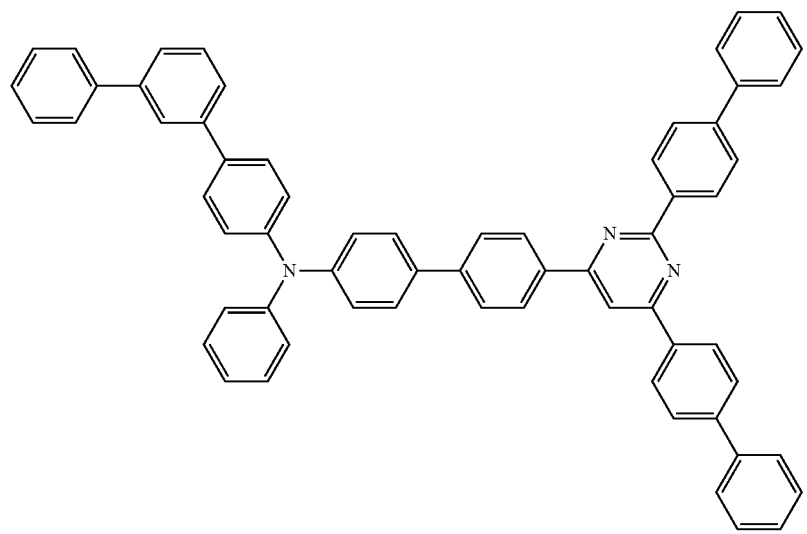

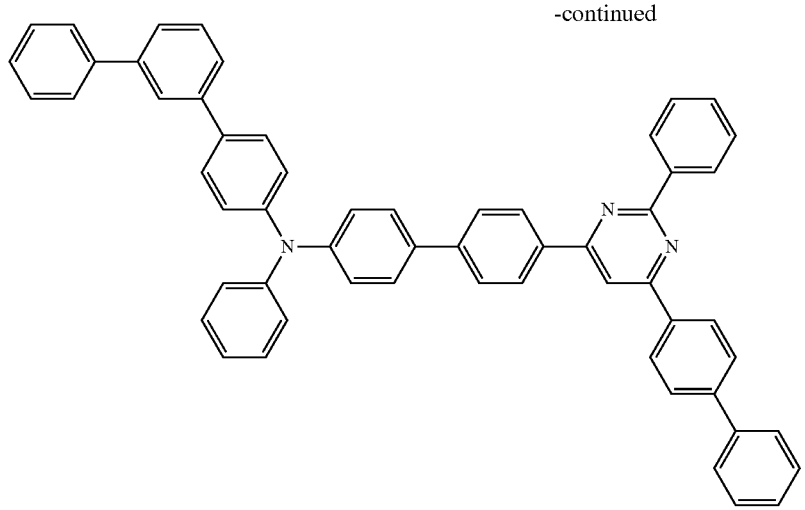
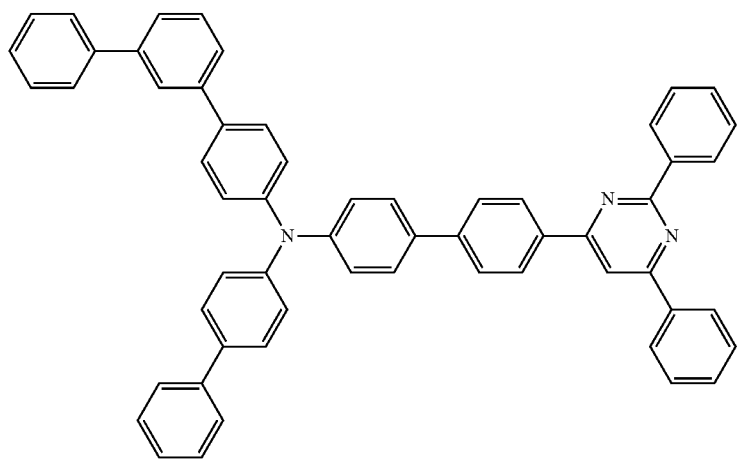
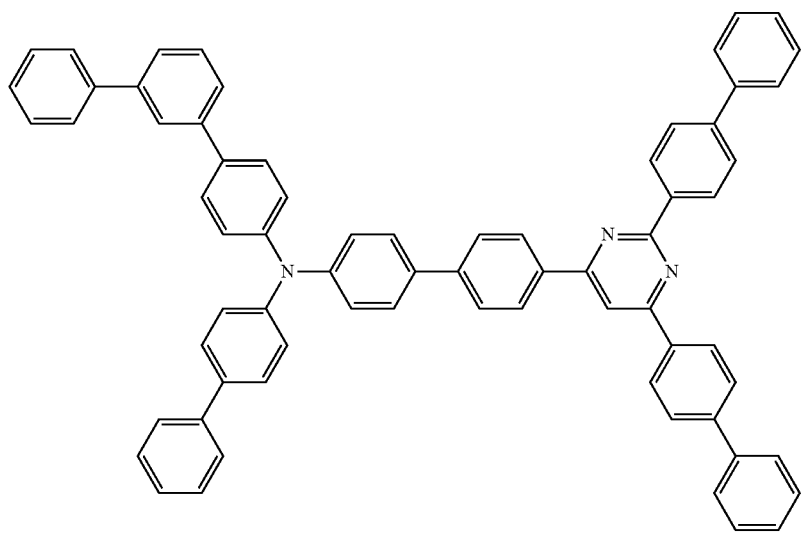

-continued
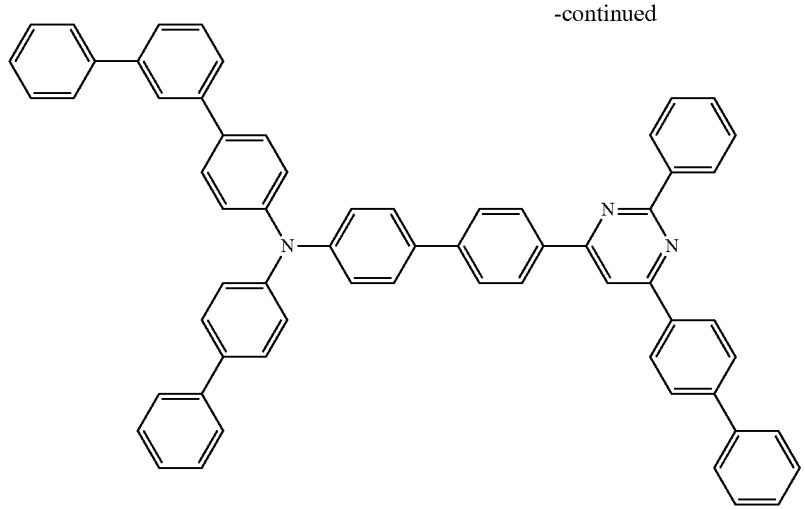
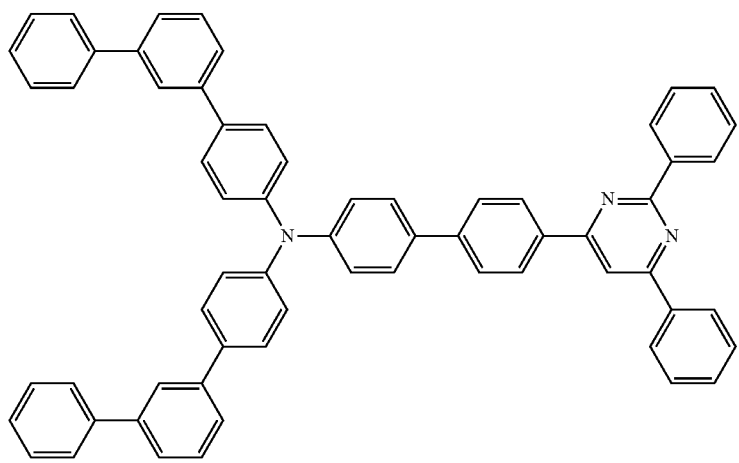
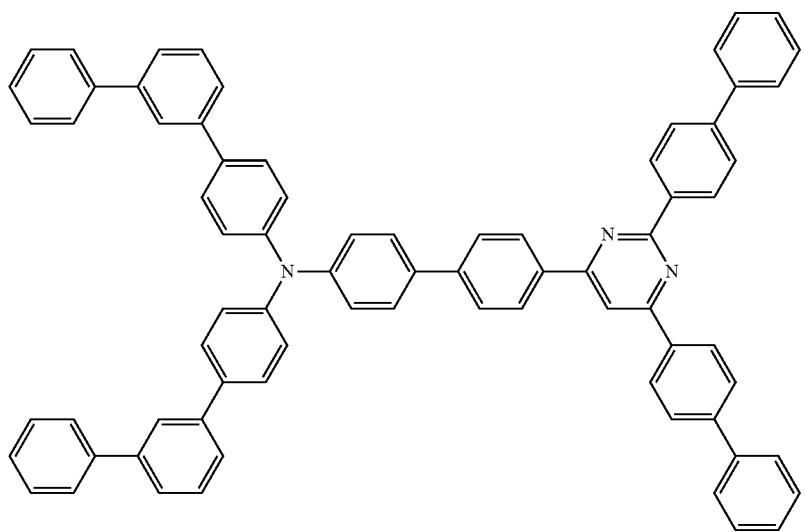

-continued
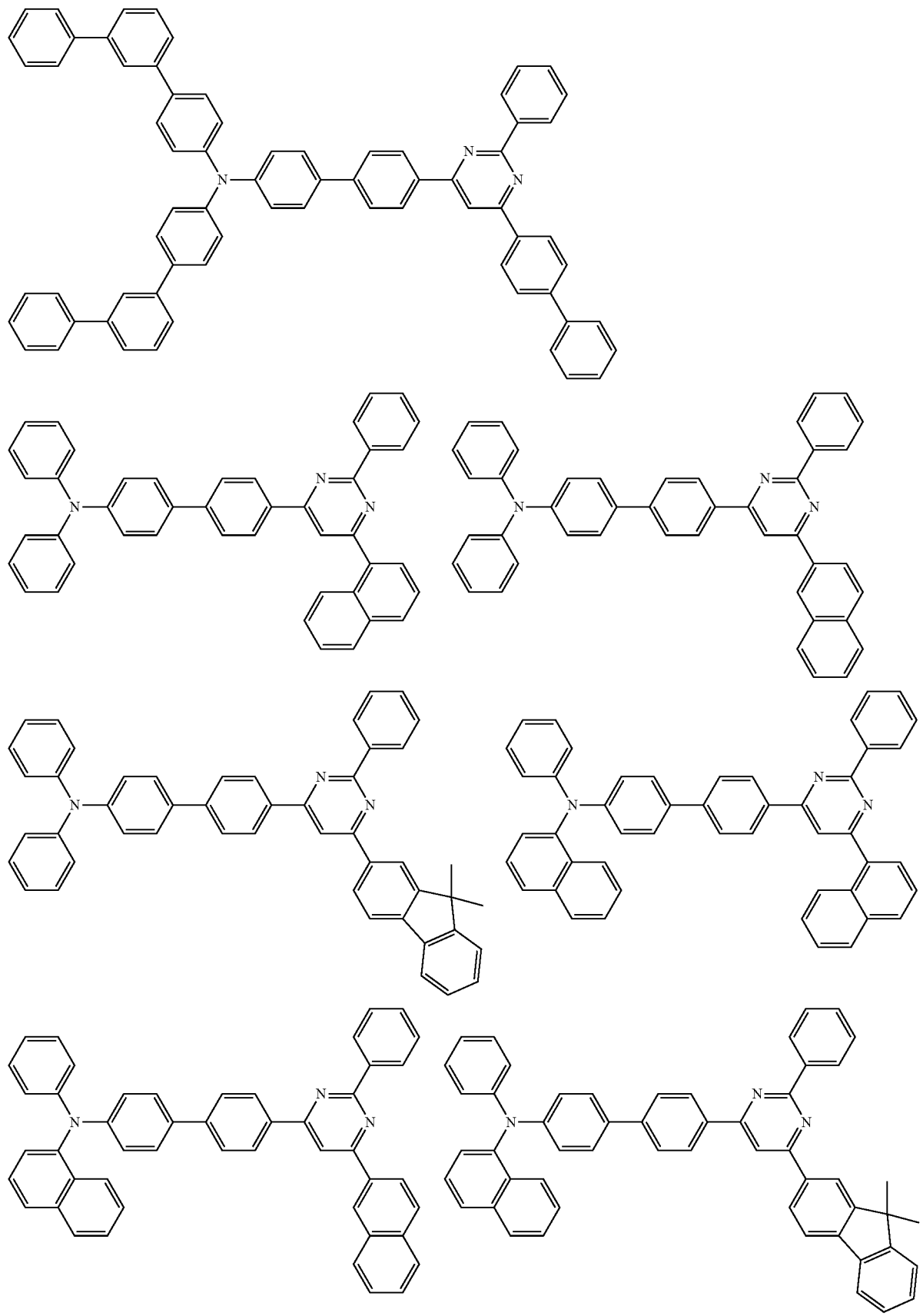

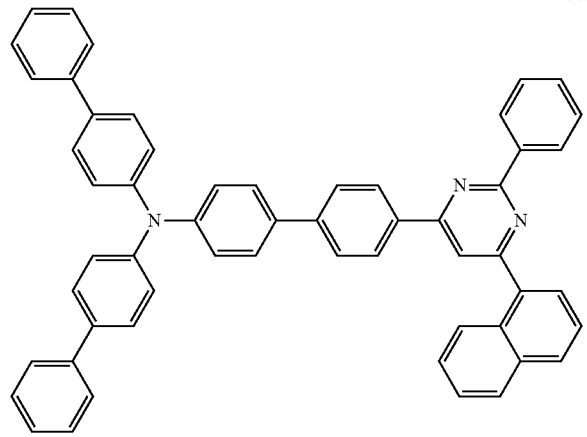
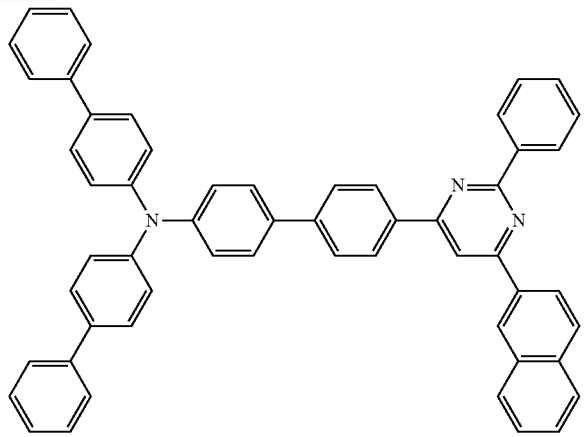
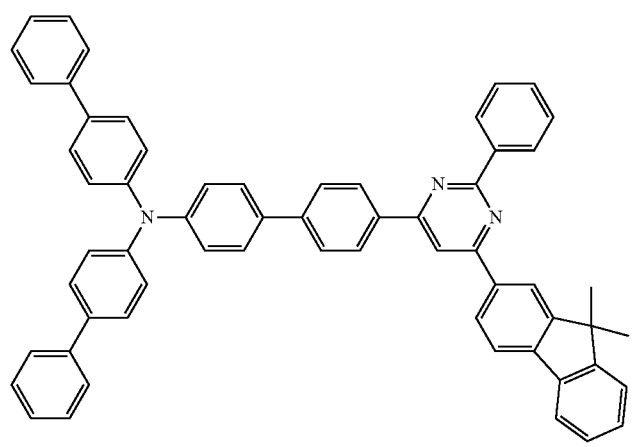
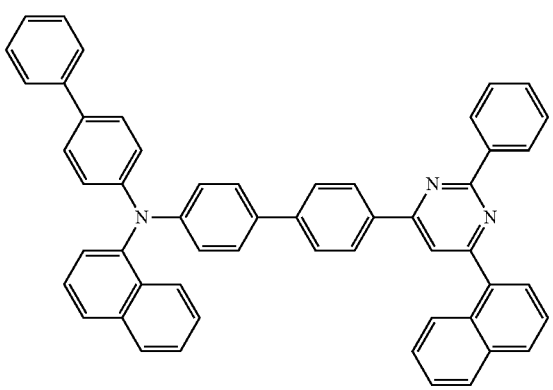
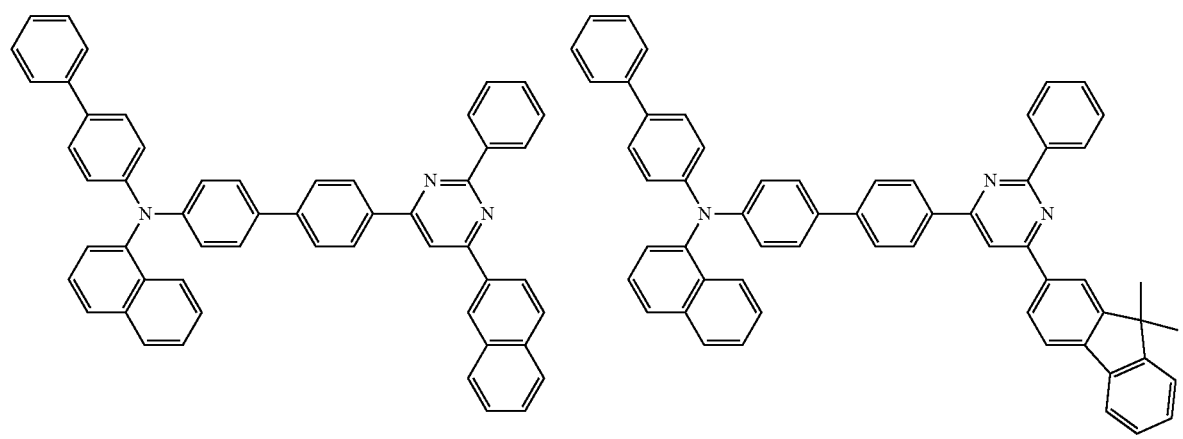

-continued
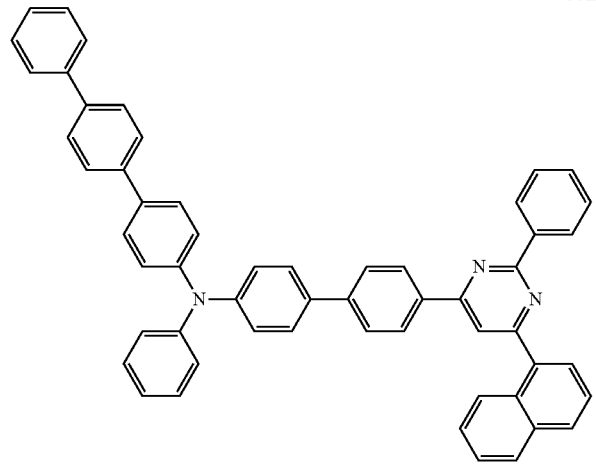
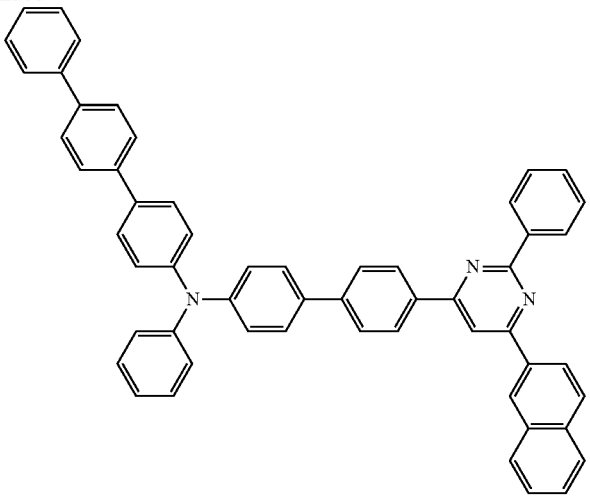
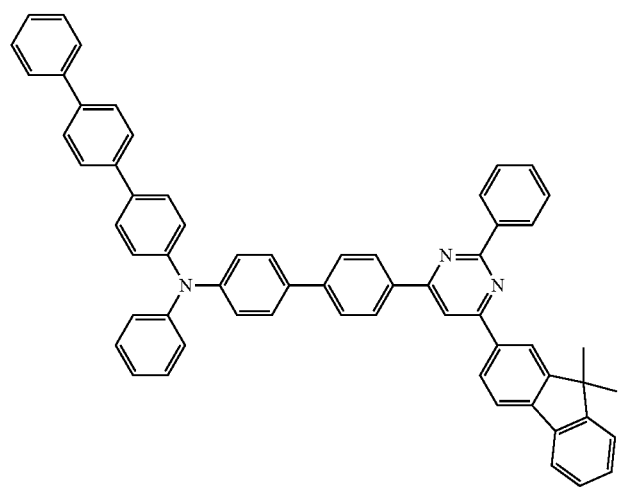
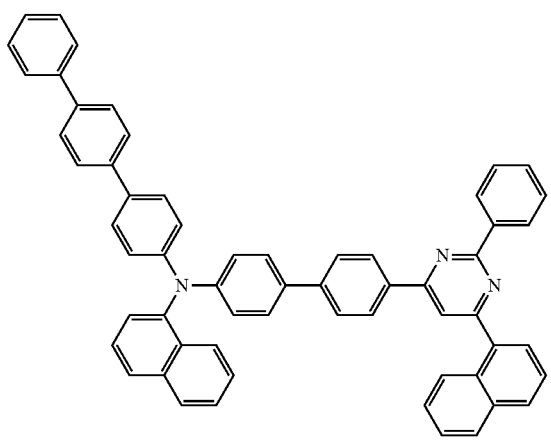
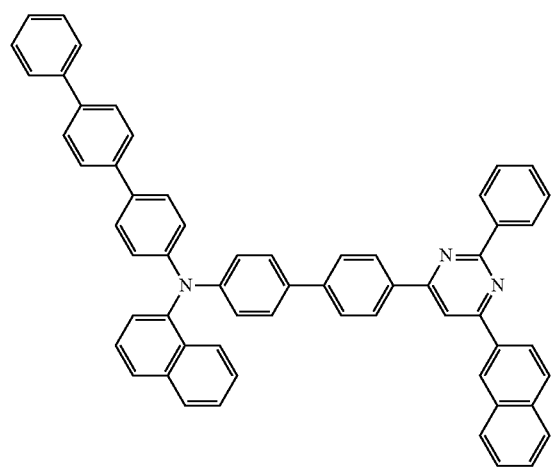
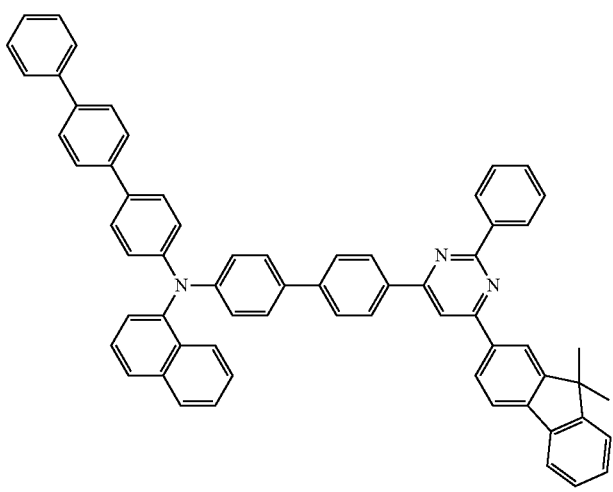

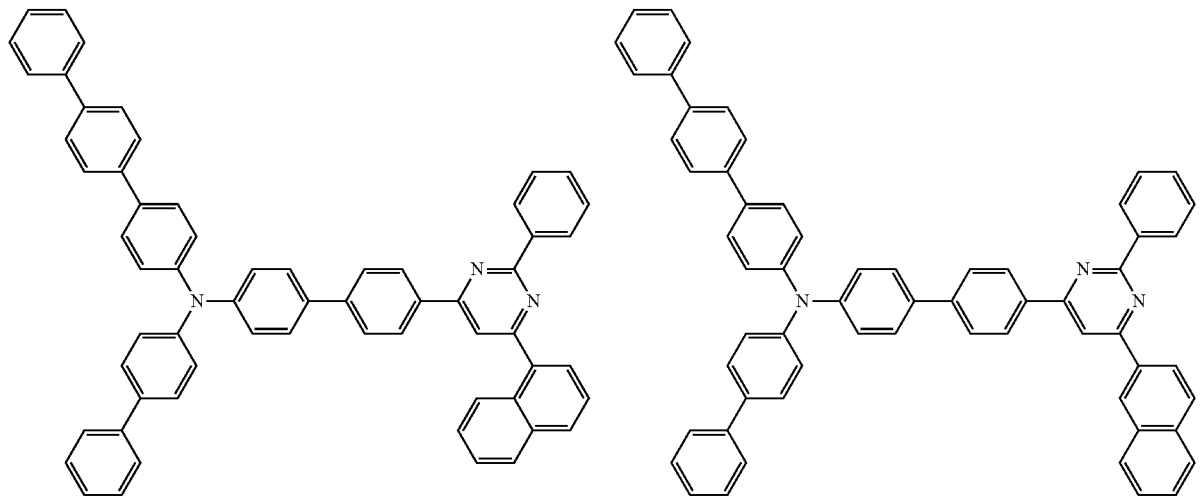
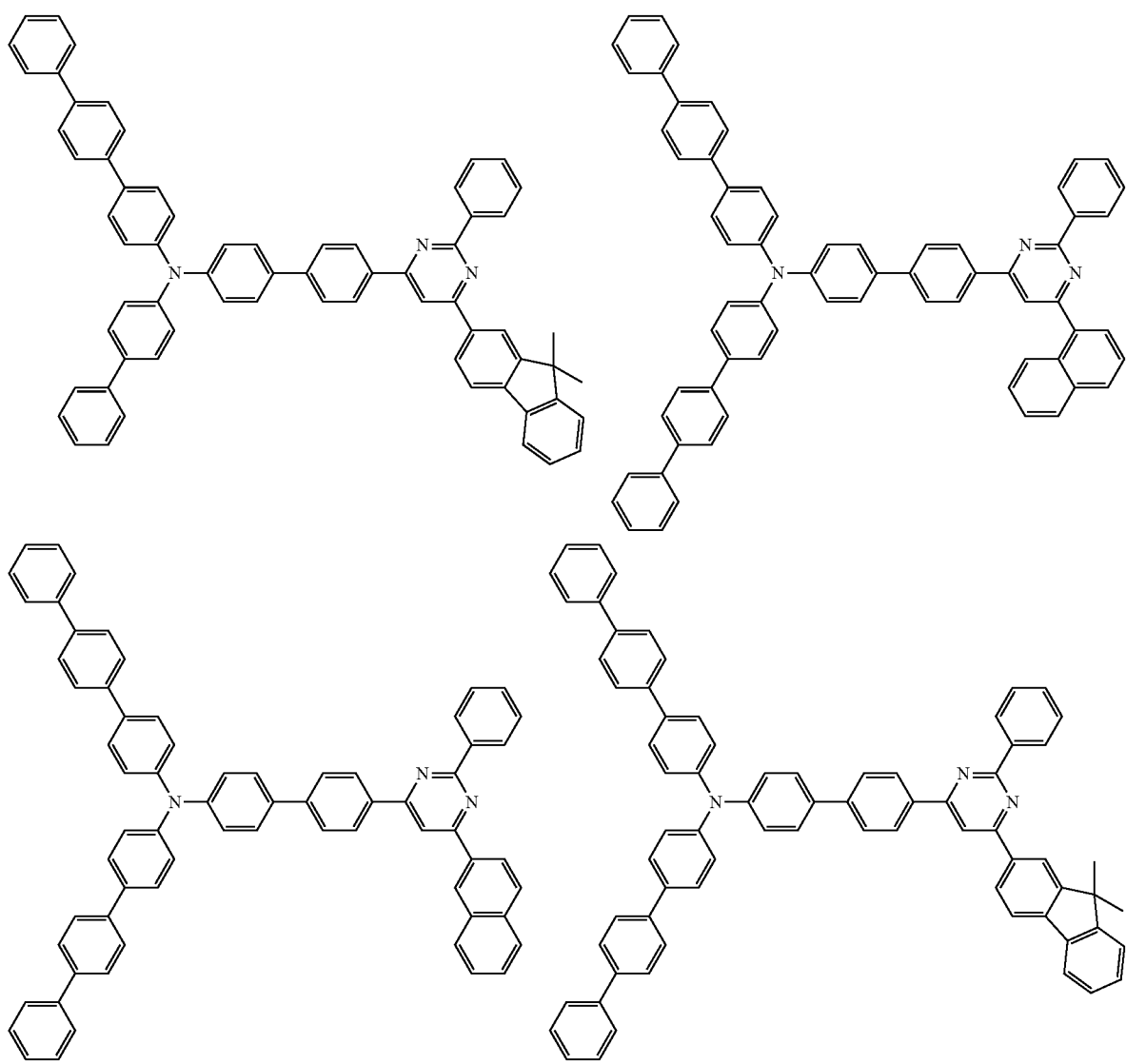

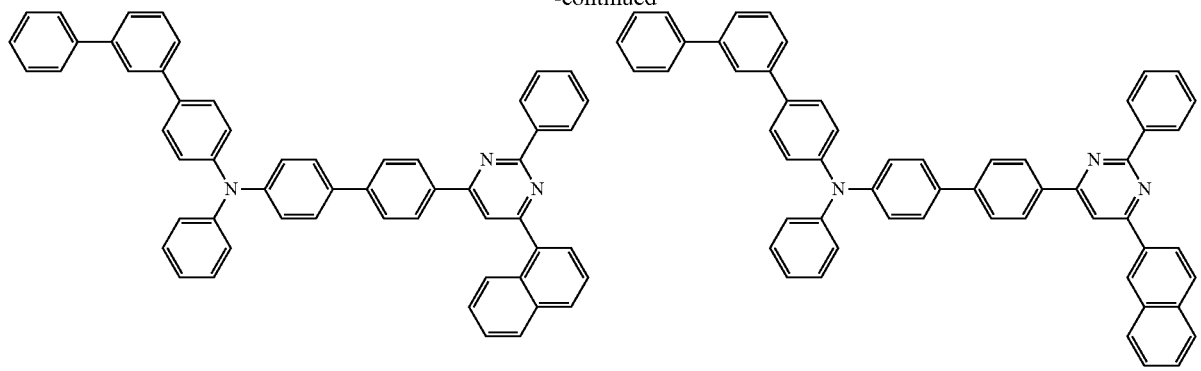
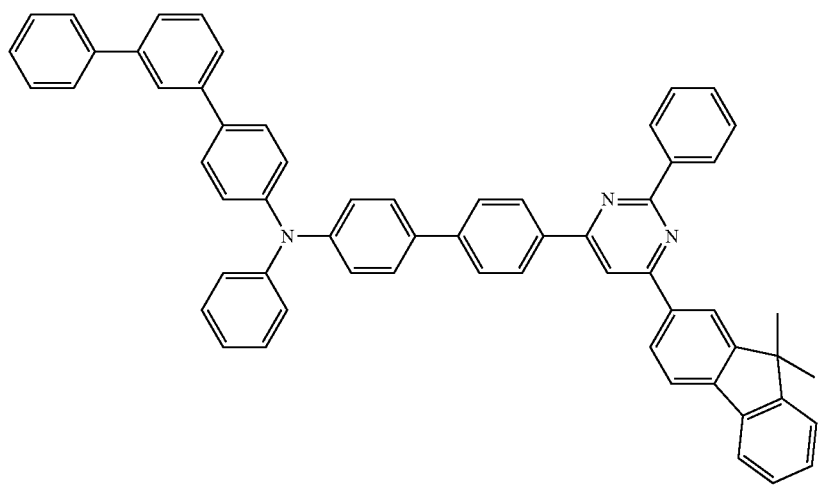
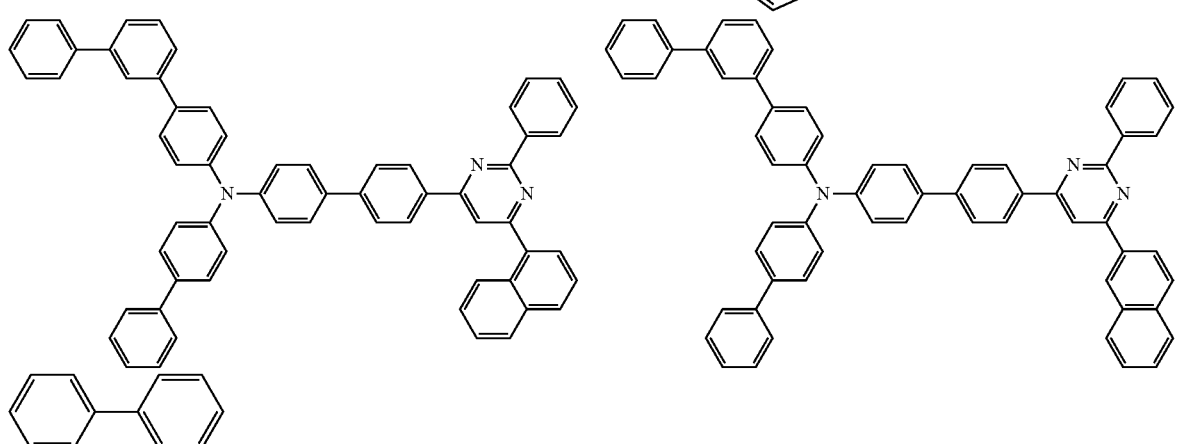
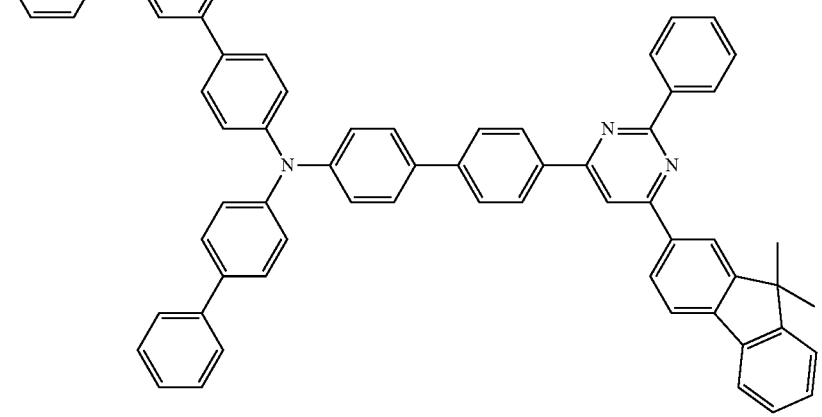

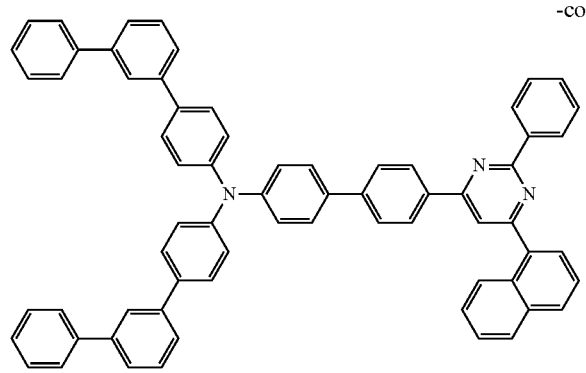
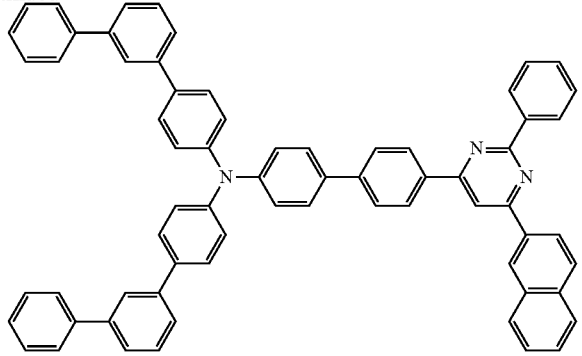
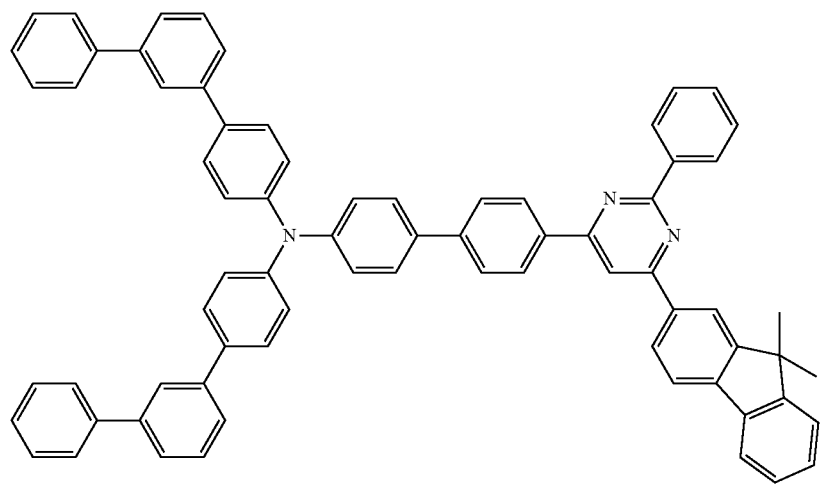
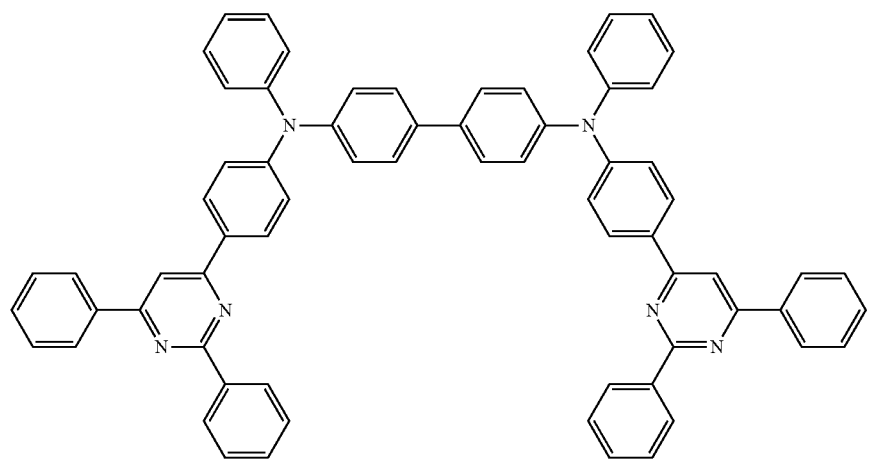

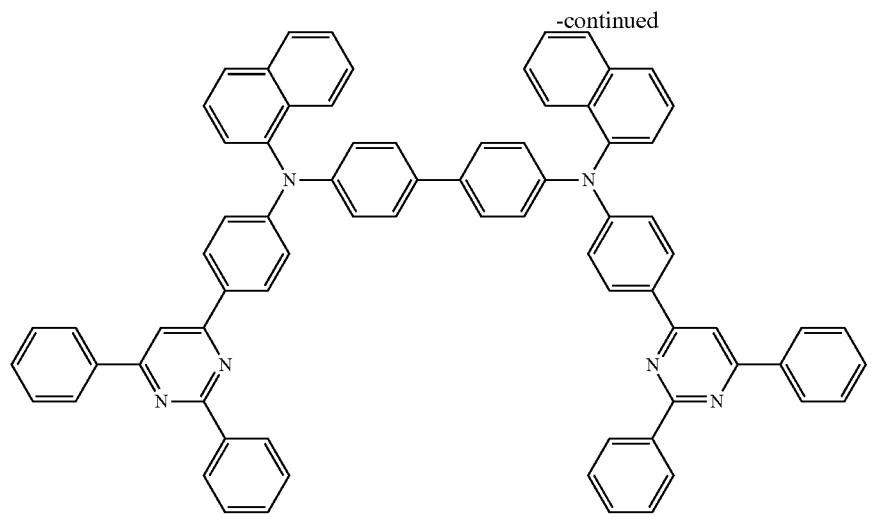
-continued
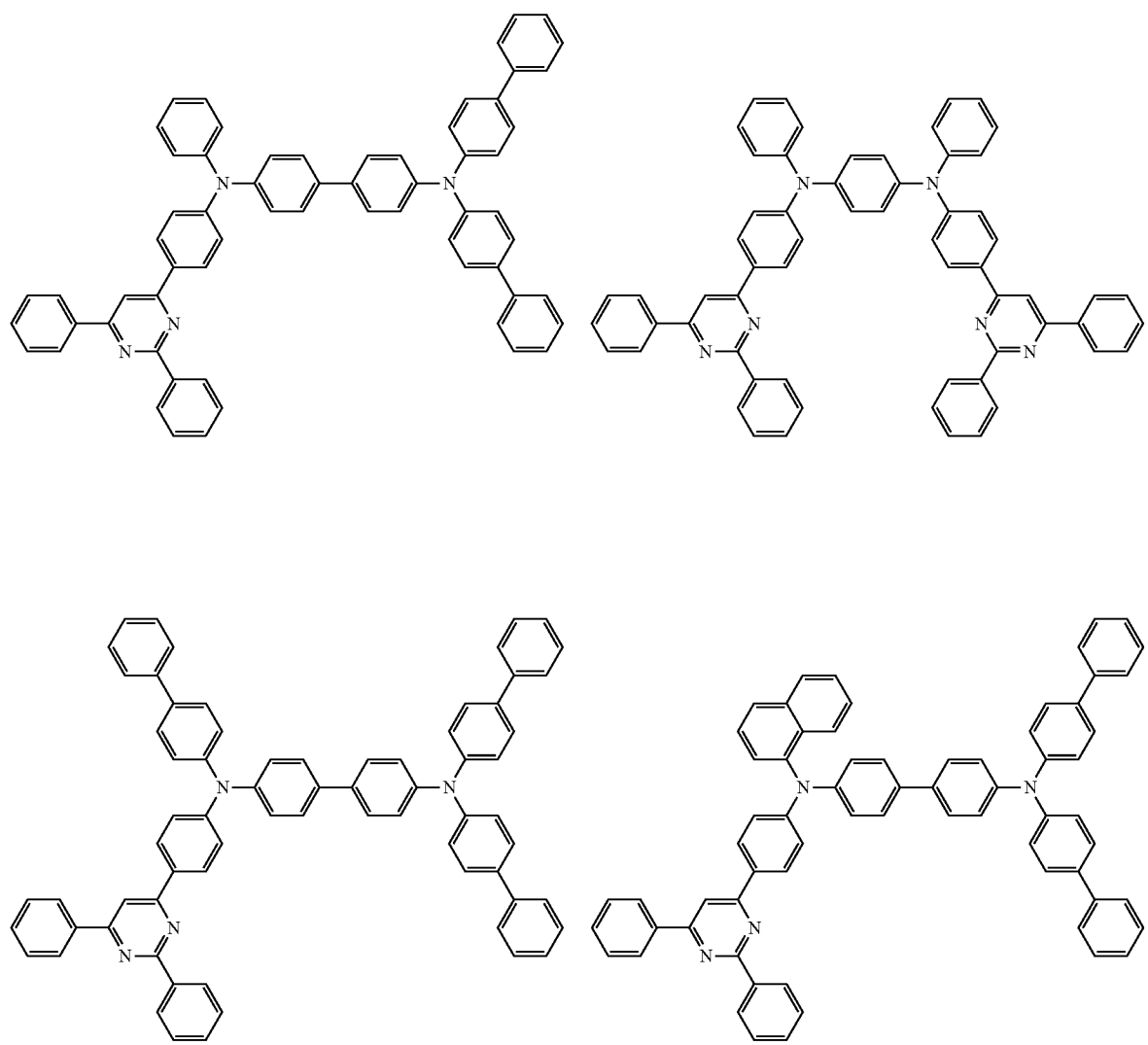

-continued
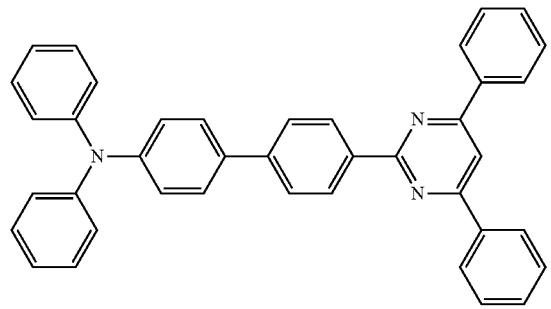
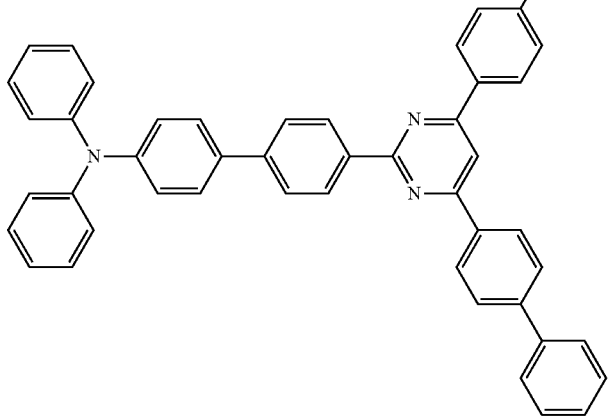
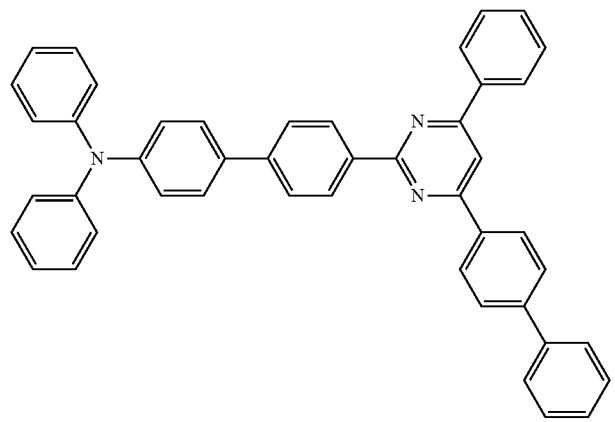
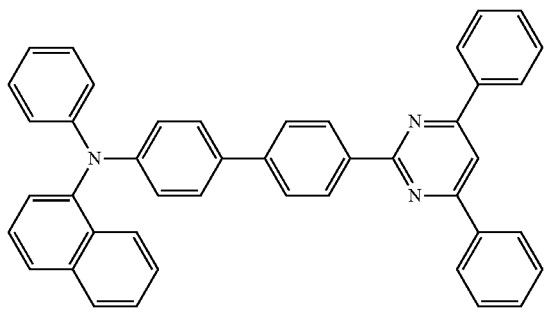
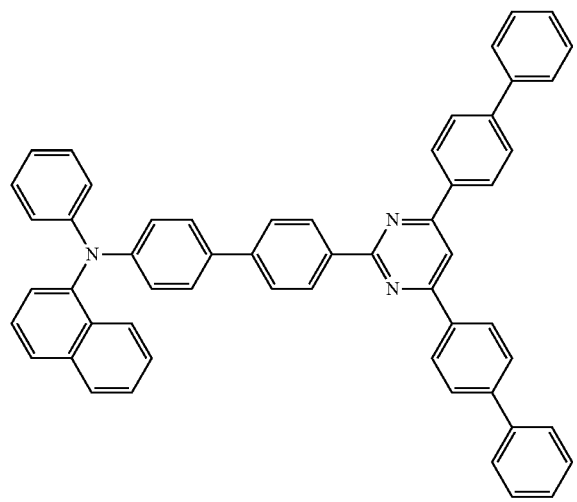
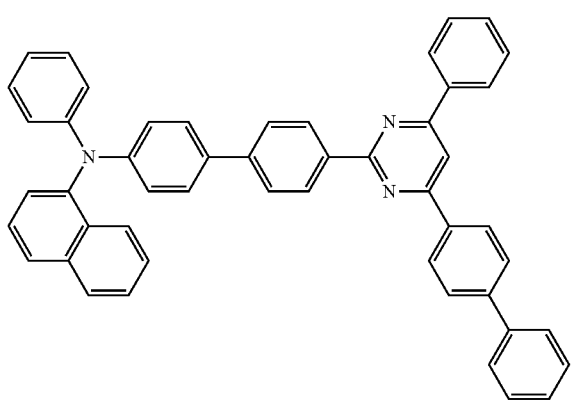

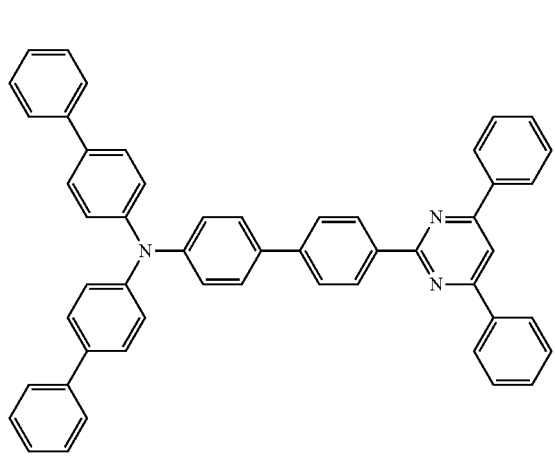
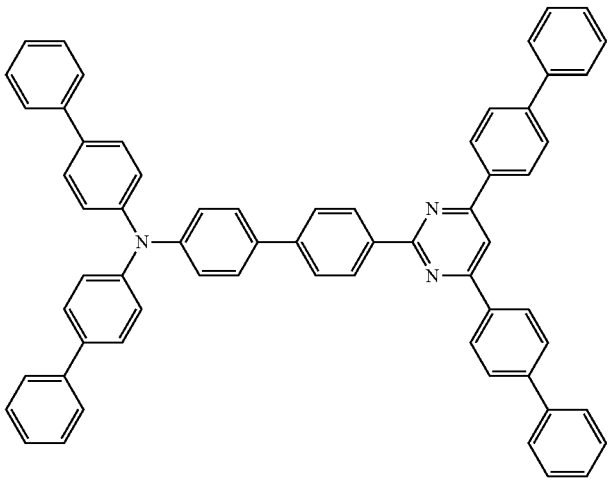
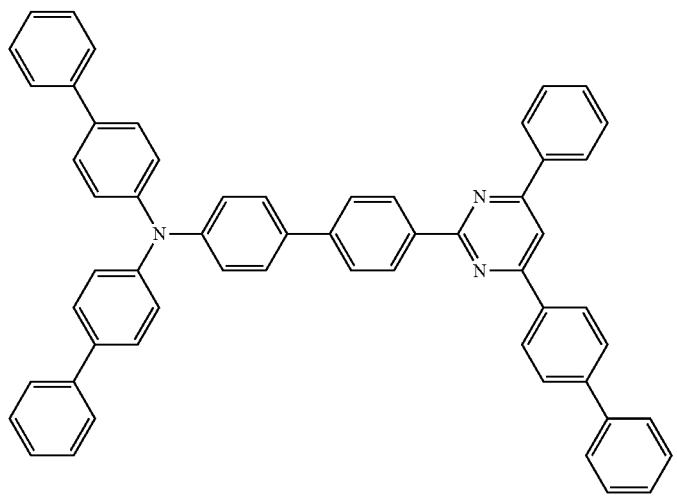
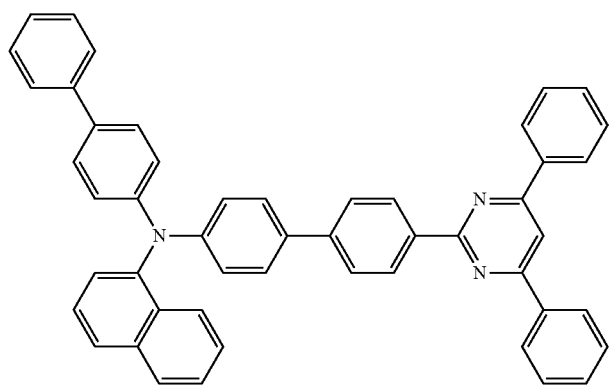

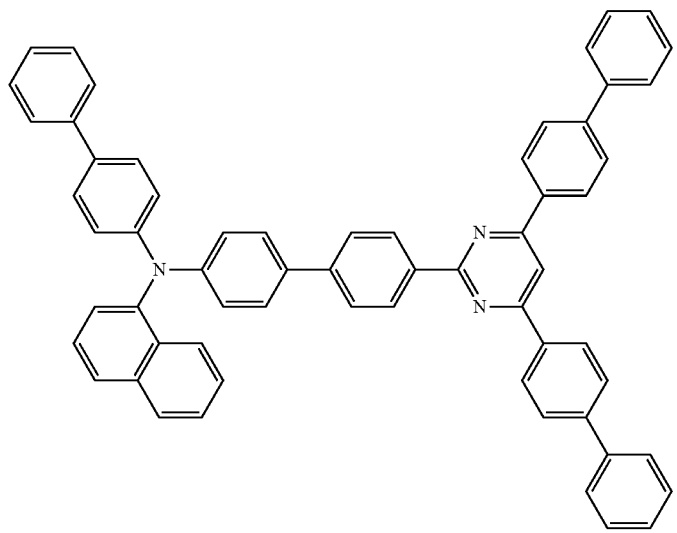
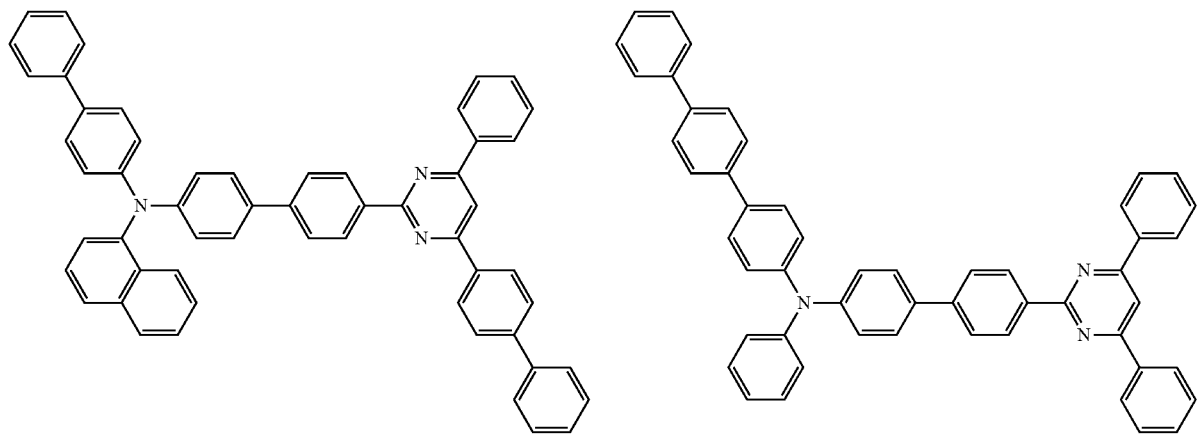
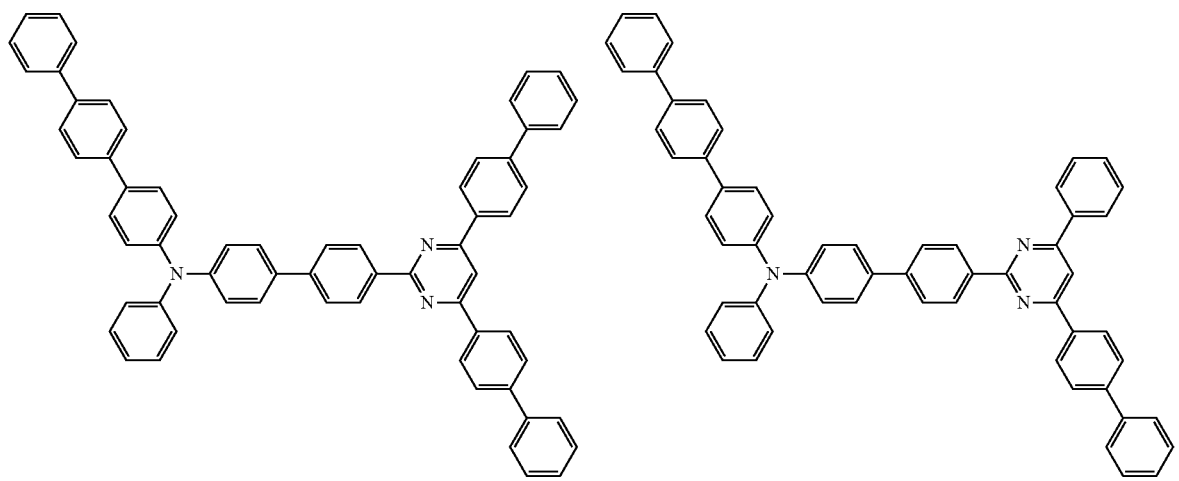

-continued
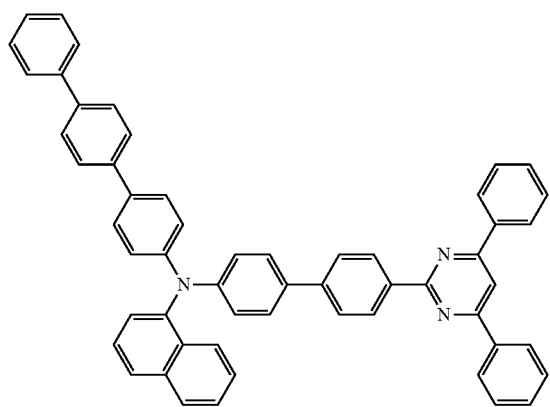
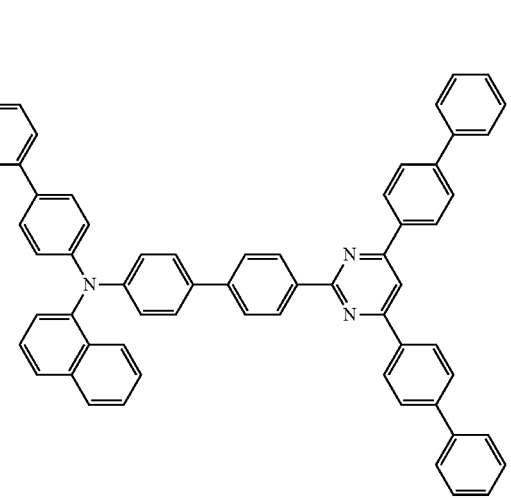
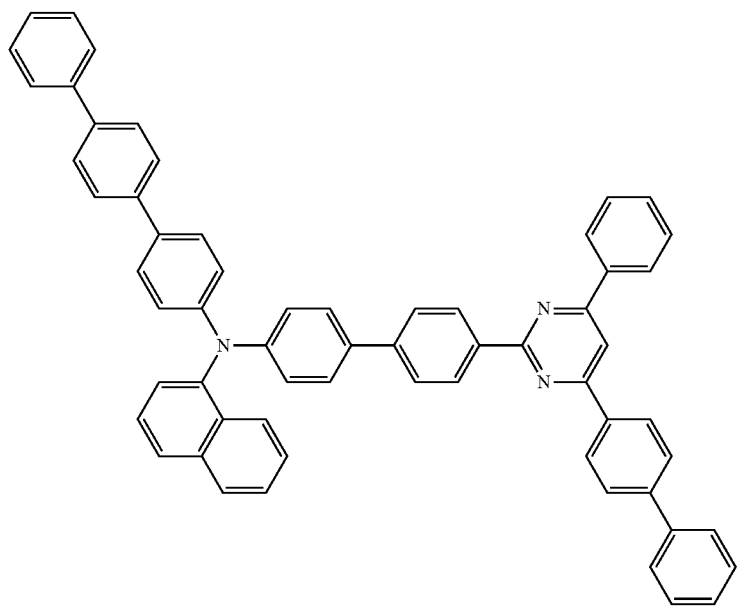 [SMILES: c1ccc(-c2ccc(-c3ccc(N(c4ccc(-c5ccc(-c6nc(-c7ccccc7)cc(-c7ccc(-c8ccccc8)cc7)n6)cc5)cc4)c4cccc5ccccc45)cc3)cc2)cc1]
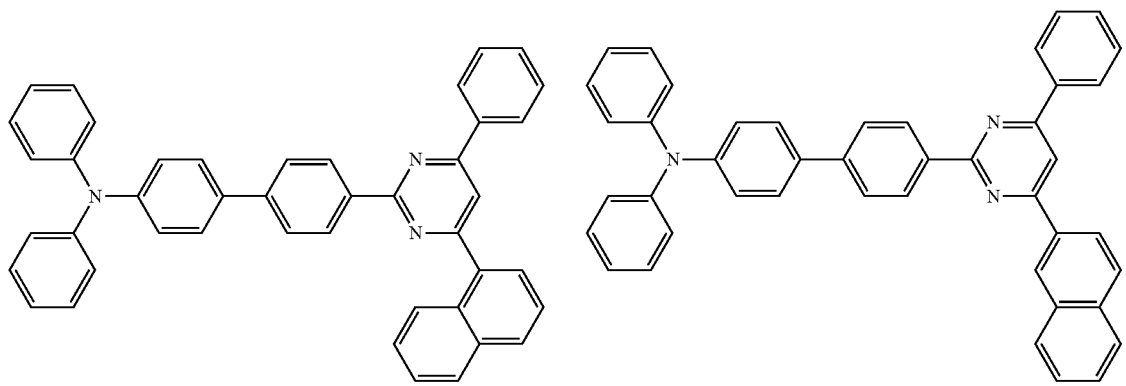

-continued
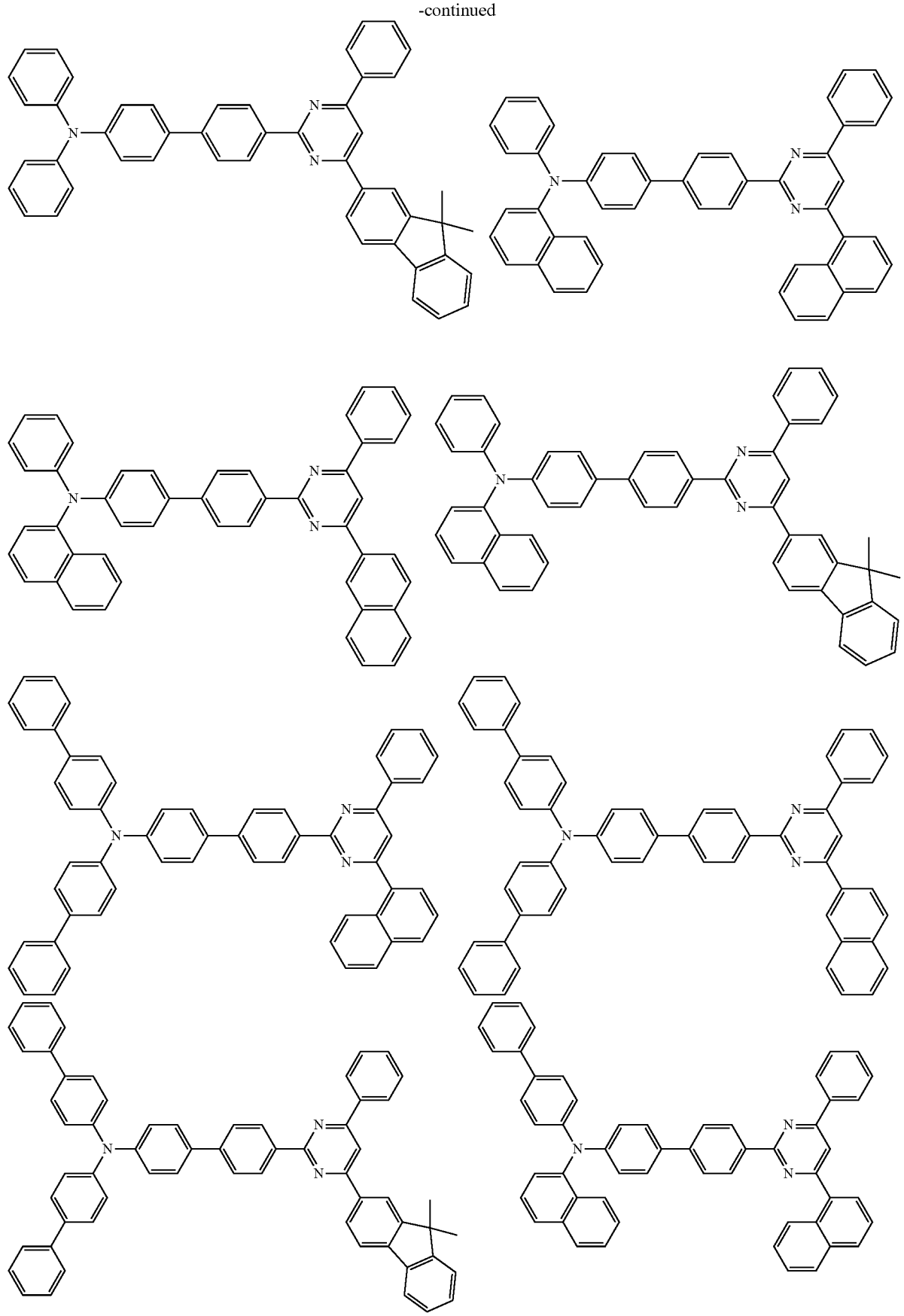

-continued
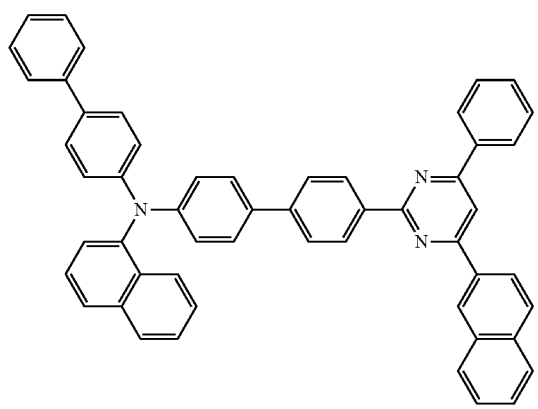
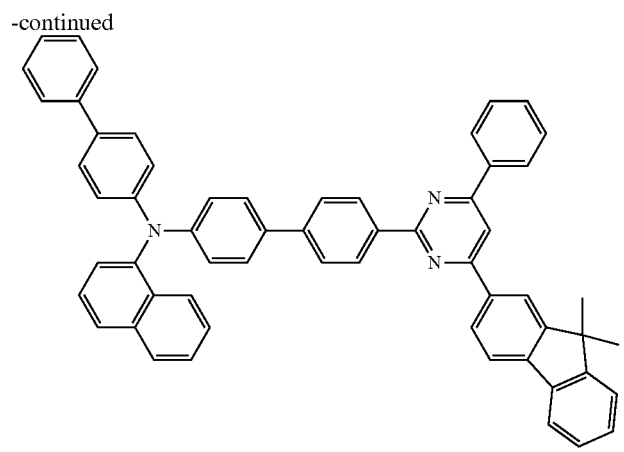
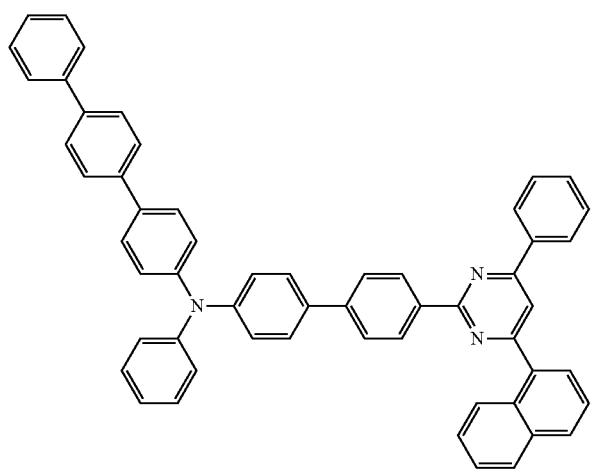
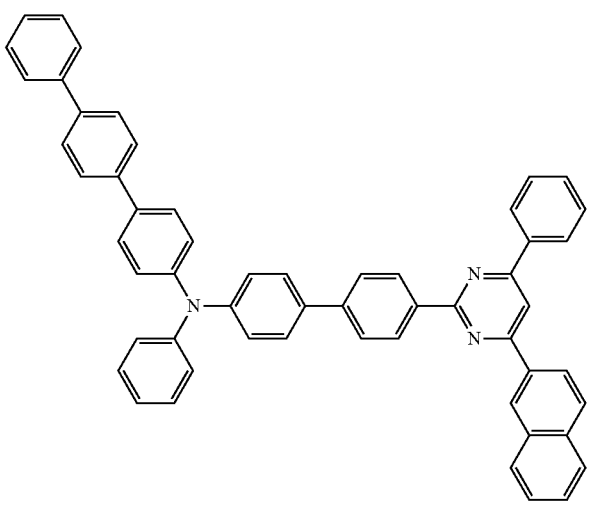
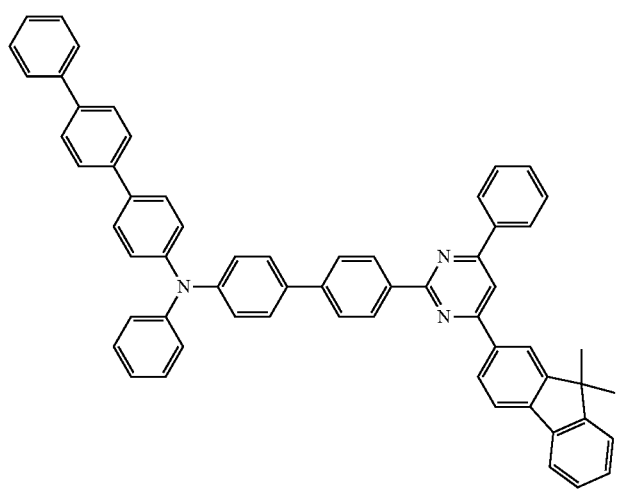
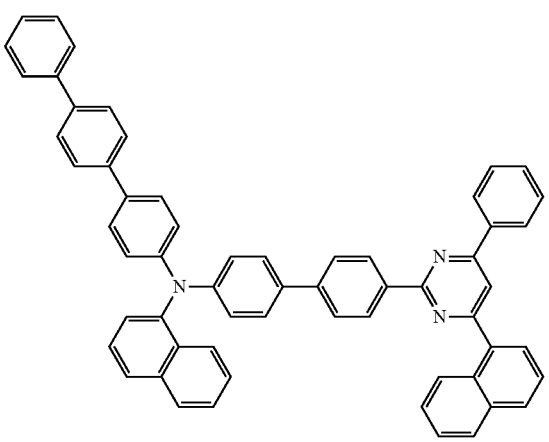

51
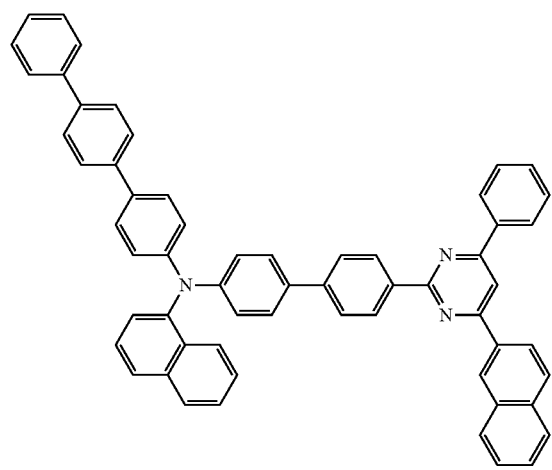
52
-continued
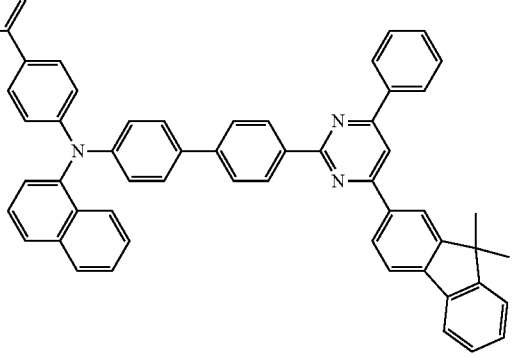
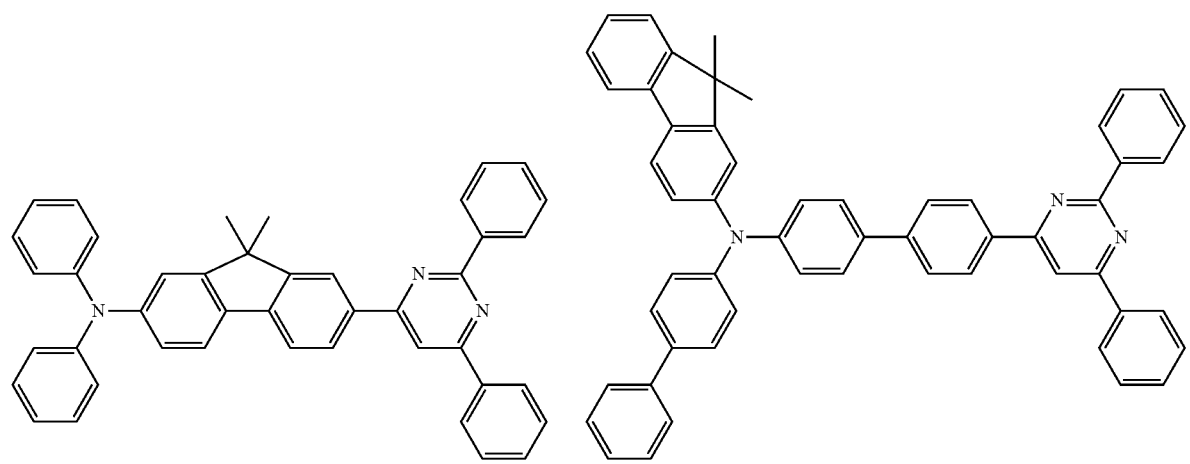
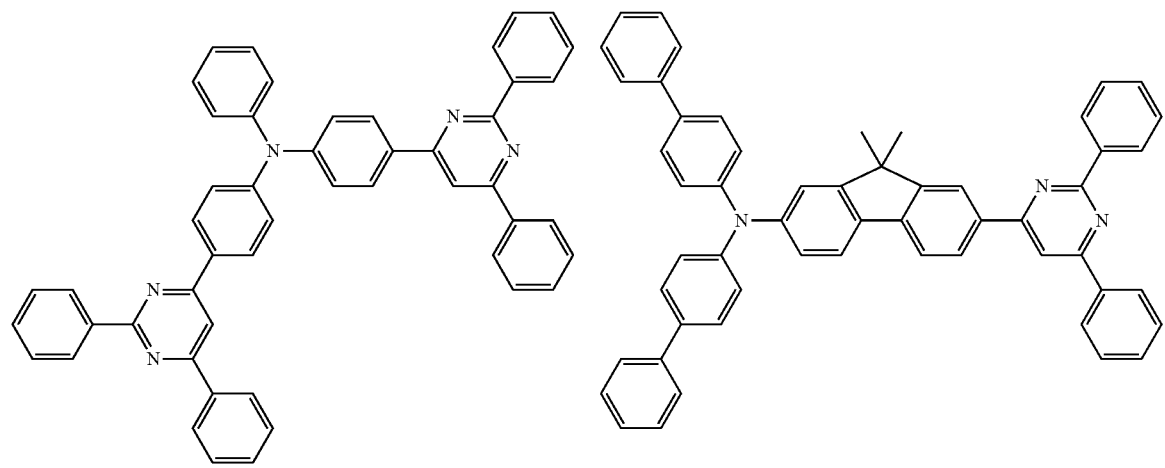

-continued
53
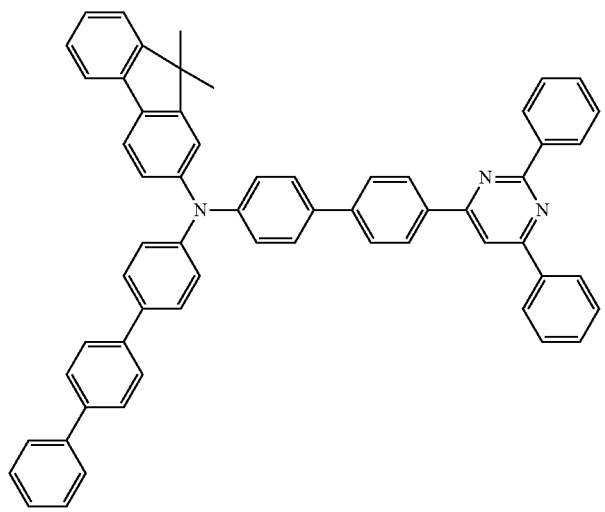
54
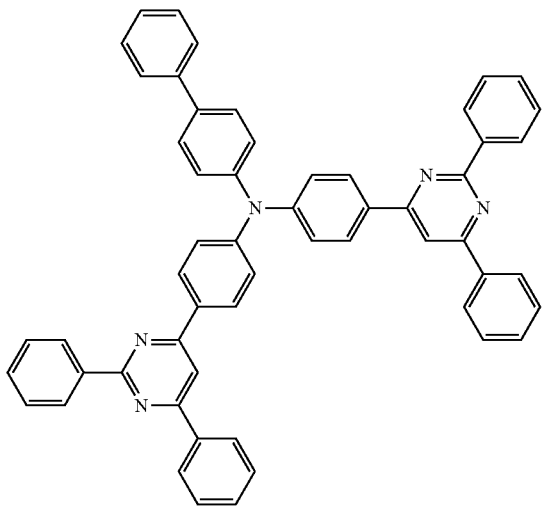
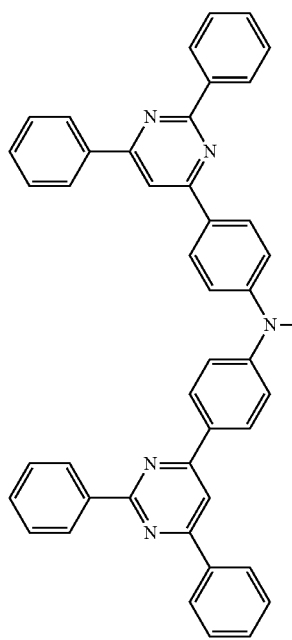
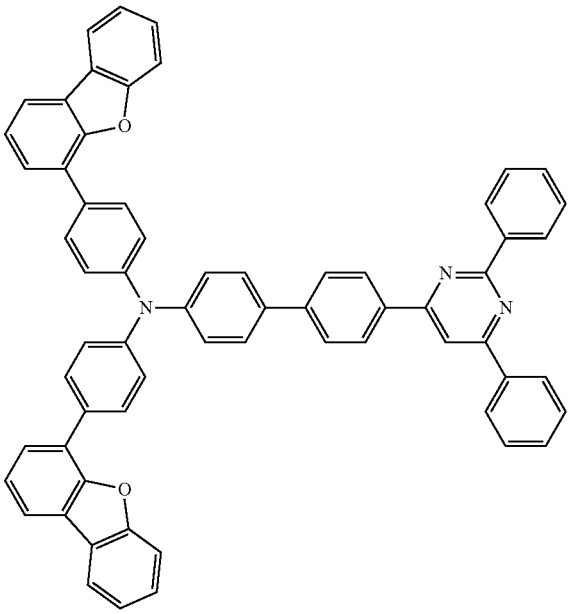

-continued
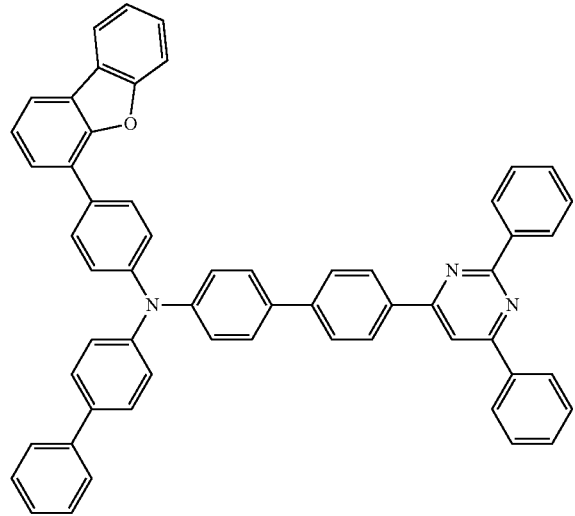
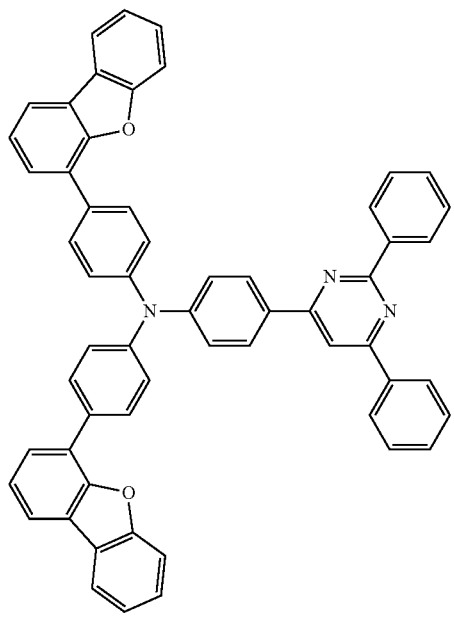
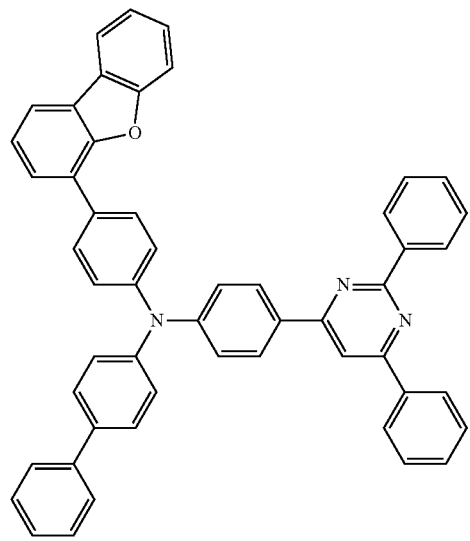
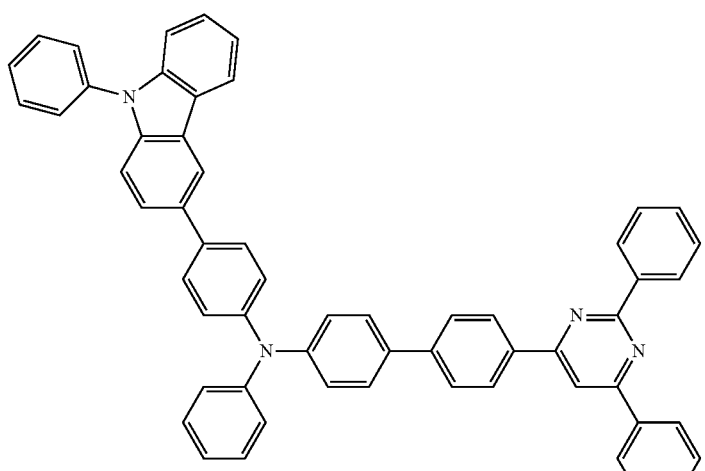

57
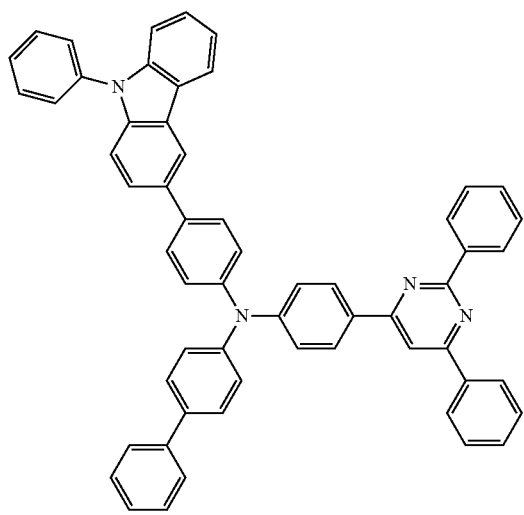
58
-continued
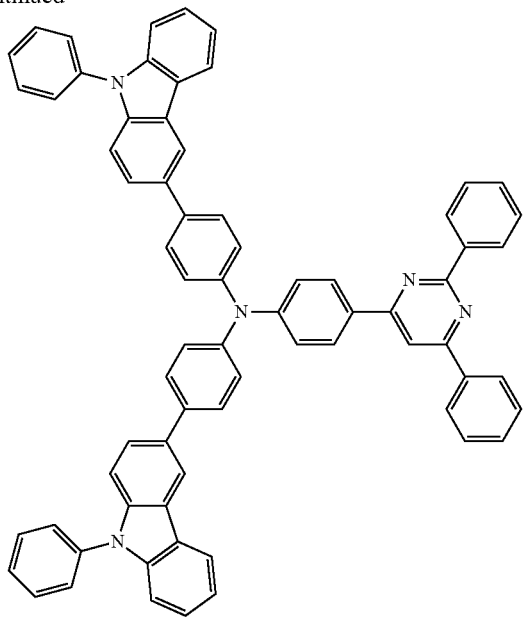
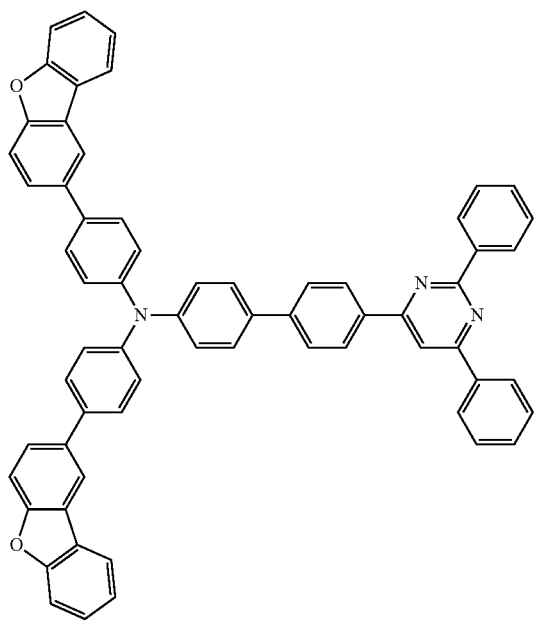
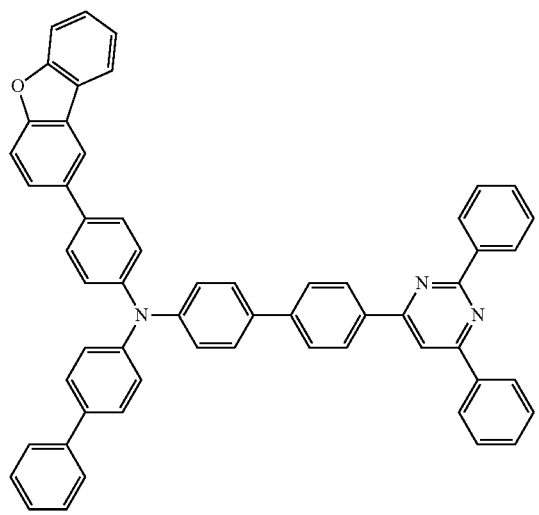

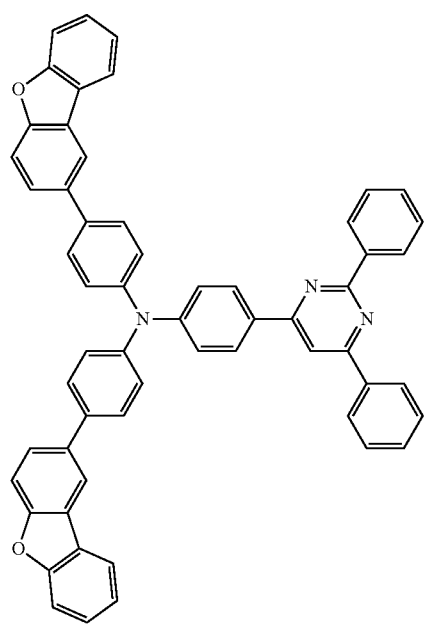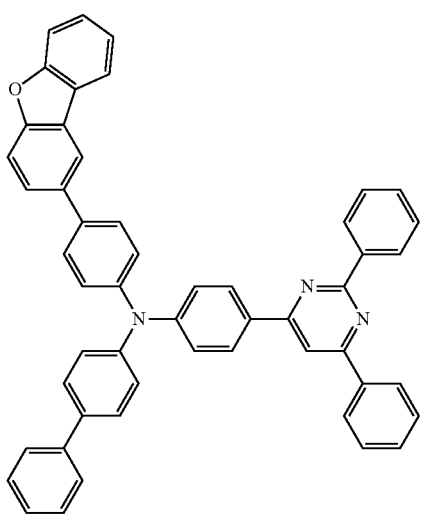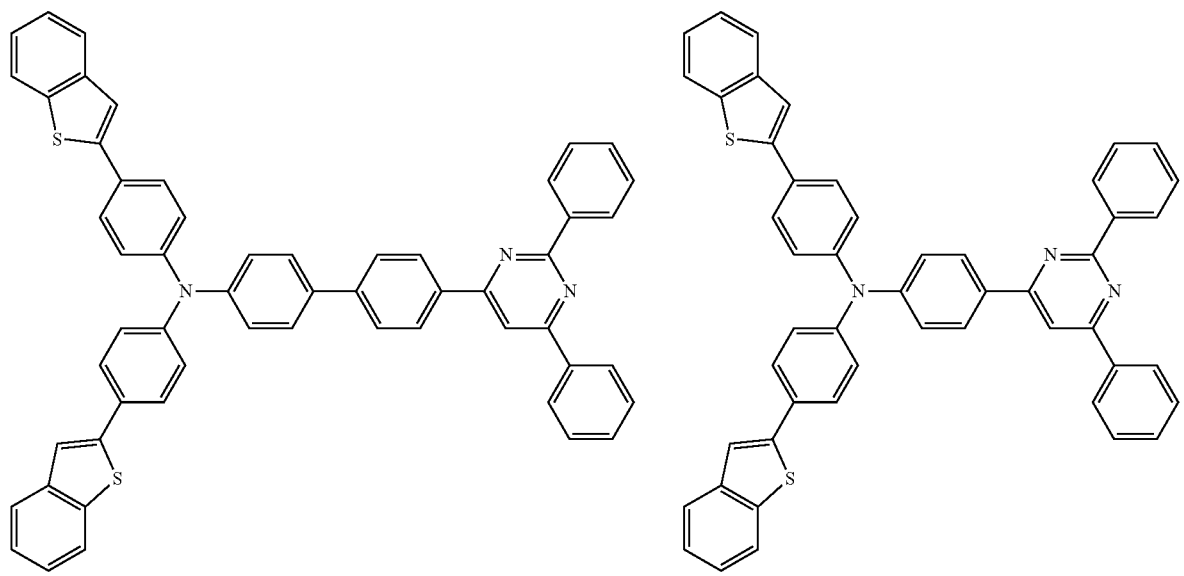

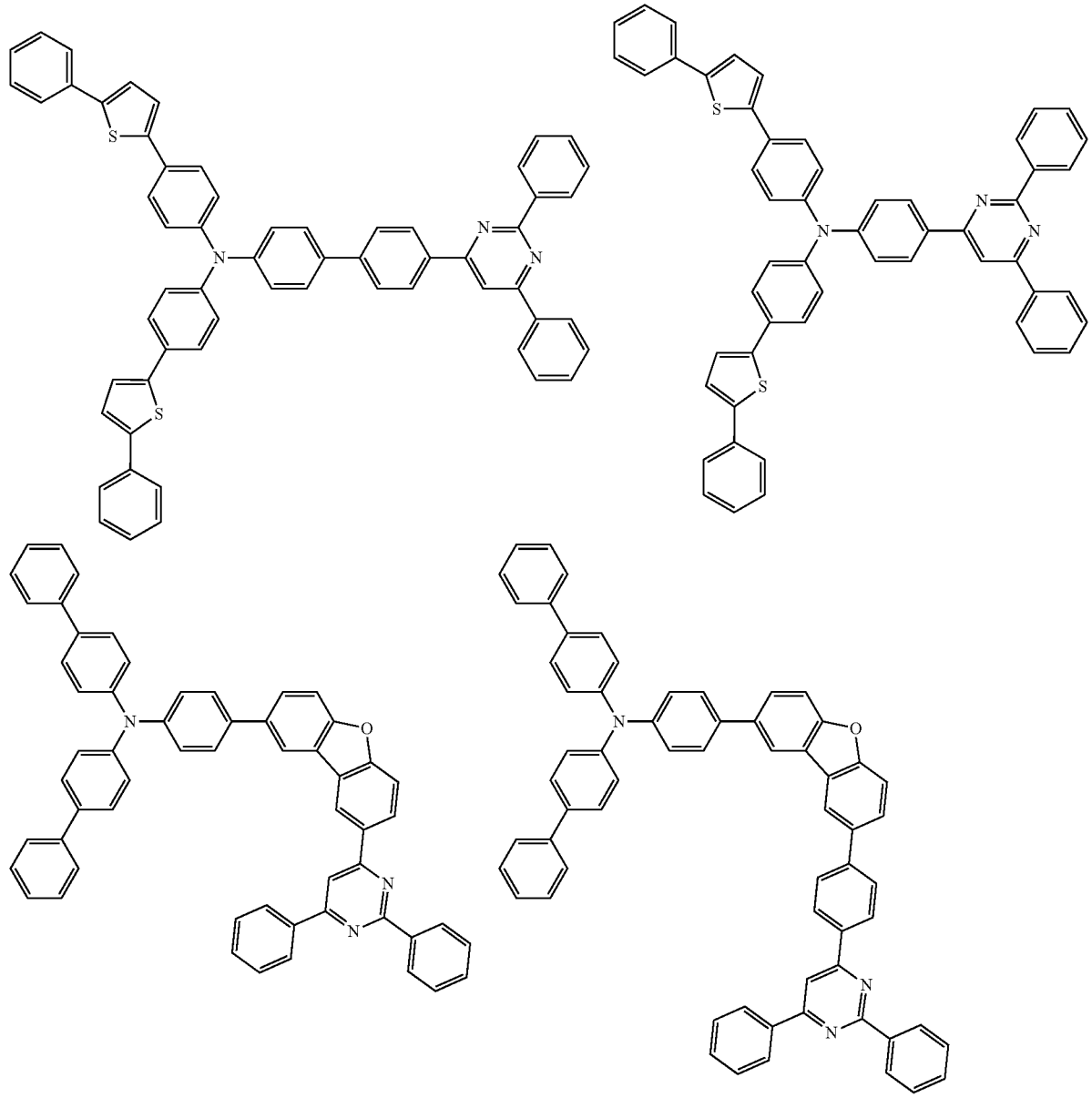

The above aromatic amine derivatives of the invention can be used as organic EL device materials such as a hole-transporting material, a phosphorescent host material or a carrier blocking layer for a white light emitting device.

The organic EL device of the invention includes a cathode, an anode, and one or more organic thin films including an emitting layer therebetween, and at least one layer of the organic thin films includes the above-described aromatic amine derivative.

The organic EL device of the invention is not limited so far as the anode, the emitting layer and the cathode are stacked in sequential order, and the device may have further one or more organic layers or inorganic layers. Furthermore, a plurality of emitting layers may be provided.

In the organic EL device of the invention, preferably, the above-mentioned organic thin film layers include a hole-transporting layer and/or a hole-injecting layer, and at least one of the hole-transporting layer and the hole-injecting layer contains the above-mentioned aromatic amine derivative. The hole-transporting layer and/or the hole-injecting layer may consist essentially of the aromatic amine derivative (contain the aromatic amine derivative as the major component) or may consist of the aromatic amine derivative.

As another embodiment of the organic EL device of the invention, preferably, at least one emitting layer contains the above-mentioned aromatic amine derivative. The emitting layer may consist essentially of the aromatic amine derivative (contain the aromatic amine derivatives as the major component) or may consist of the aromatic amine derivative. When the aromatic amine derivative is contained as the major component, the emitting layer may further contain the phosphorescent dopant described later.

As the device configuration of the organic EL device, the below-mentioned first to third embodiments can be given. In these embodiments, the emitting layer may be a multilayer stack of emitting layers. Furthermore, it is preferable that a hole-transporting region be provided between the anode and the emitting layer.

First Embodiment

The organic EL device according to this embodiment has a device configuration in which at least one emitting layer is provided. Specific examples of the configuration are given below.

(1) Anode/emitting layer/electron-injecting•transporting layer/cathode (2) Anode/hole-injecting layer/emitting layer/electron-injecting•transporting layer/cathode (3) Anode/hole-injecting layer/hole-transporting layer/emitting layer/electron-injecting•transporting layer/cathode Second Embodiment The organic EL device according to this embodiment has a tandem device configuration in which at least two emitting layers (units having a emitting layer) are provided. A carrier generation layer (may referred to as CGL) is provided between the two emitting layers. An electron-transporting region can be provided in each unit.

Specific examples of the tandem device configuration are given below.

(4) Anode/hole-injecting•transporting layer/fluorescent emitting layer/carrier generation layer/fluorescent emitting layer/electron-injecting•transporting layer/cathode (5) Anode/hole-injecting•transporting layer/fluorescent emitting layer/electron-injecting•transporting layer/carrier generation layer/fluorescent emitting layer/cathode (6) Anode/hole-injecting•transporting layer/fluorescent emitting layer/electron-injecting•transporting layer/carrier generation layer/fluorescent emitting layer/blocking layer/cathode (7) Anode/hole-injecting•transporting layer/phosphorescent emitting layer/carrier generation layer/fluorescent emitting layer/electron-injecting•transporting layer/cathode (8) Anode/hole-injecting•transporting layer/fluorescent emitting layer/electron-injecting•transporting layer/carrier generation layer/phosphorescent emitting layer/cathode Third Embodiment The organic EL device according to this embodiment has a plurality of emitting layers and a carrier blocking layer between any two of the emitting layers.

As the preferred configuration of the organic EL device according to this embodiment, there can be given the configurations as disclosed in Japanese Patent No. 4134280, US2007/0273270A1 and WO2008/023623A1, and, specifically, the configuration in which an anode, a first emitting layer, a carrier blocking layer, a second emitting layer and a cathode are sequentially stacked, and an electron-transporting region having a blocking layer for preventing diffusion of triplet excitons is further provided between the second emitting layer and the cathode. Here, the carrier blocking layer means a layer for controlling the carrier injection to an emitting layer and the carrier balance between electrons and holes injected in the emitting layer by providing an energy barrier of a HOMO level or a LUMO level between adjacent emitting layers.

The specific examples of such configuration are given below.

(9) Anode/hole-injecting•transporting layer/first emitting layer/carrier blocking layer/second emitting layer/electron-injecting•transporting layer/cathode

(10) Anode/hole-injecting•transporting layers/first emitting layer/carrier blocking layer/second emitting layer/third emitting layer/electron-injecting•transporting layer/cathode In the specification, the "hole-injecting-transporting layer" means at least one of hole-injecting layer and hole-transporting layer, and the "electron-injecting•transporting layer" means at least one of electron-injecting layer and electron-transporting layer.

Of the hole-injecting•transporting layers, it is preferable that the layer in contact with the anode include an acceptor material.

Such a configuration realizes a device having a low voltage driving and a high luminous efficiency due to the effects as described in the below-mentioned patent publications.

As the acceptor material, a hexaazatriphenylene derivative as disclosed in Japanese Patent Nos. 3614405 and 3571977 or U.S. Pat. No. 4,780,536 can be used. In addition, an inorganic compound such as p-type Si or p-type SiC, an electron accepting inorganic oxide such as a molybdenum oxide, an electron accepting organic compound such as a TCNQ derivative or the like can be preferably used.

As the acceptor material, the compound shown by the following general formula (10) or (11) is used preferably.

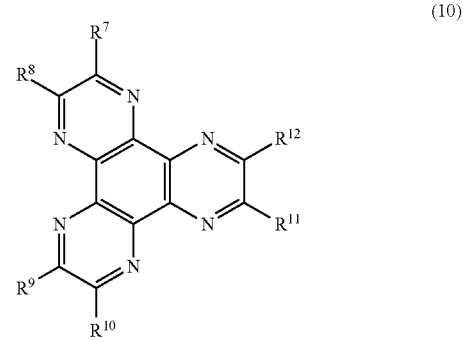

(10)

In the formula (10), $R^7$ to $R^{12}$ are independently a cyano group, —$CONH_2$, carboxyl group or $COOR^{13}$ ($R^{13}$ is alkyl group having 1 to 20 carbon atoms or a cycloalkyl group), or $R^7$ and $R^8$, $R^9$ and $R^{10}$, and $R^{11}$ and $R^{12}$ bond to each other to form a group shown by —CO—O—CO—.

Examples of the above alkyl group or cycloalkyl group include a linear, branched or cyclic one, preferably having 1 to 12 carbon atoms, more preferably having 1 to 8 carbon atoms. Specific examples thereof include methyl, ethyl, n-propyl, isopropyl, n-butyl, sec-butyl, t-butyl, n-hexyl, n-octyl, n-decyl, n-hexadecyl, cyclopropyl, cyclopentyl and cyclohexyl.

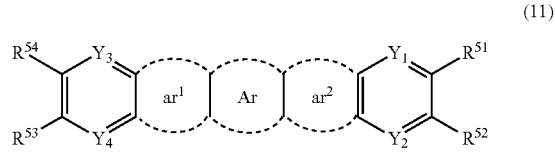

(11)

In the formula (11), Ar is a condensed ring having 6 to 24 ring carbon atoms or a hetro ring having 6 to 24 ring atoms. $ar^1$ and $ar^2$ may be the same or different and are the following formula (i) or (ii).

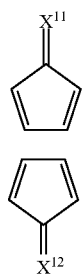

In the formula, $X^{11}$ and $X^{12}$ may be the same or different and are any of divalent groups shown by the following formulas (a) to (g).

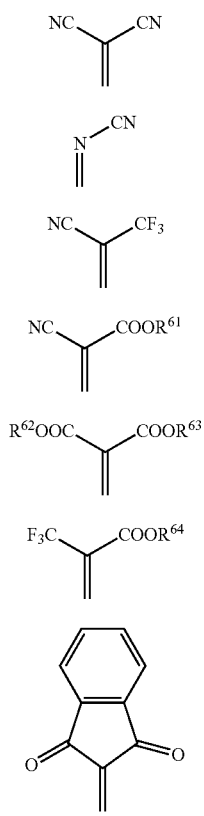

In the formulas, $R^{61}$ to $R^{64}$ may be the same or different and are a hydrogen atom, a substituted or unsubstituted fluoroalkyl group having 1 to 20 carbon atoms, a substituted or unsubstituted alkyl group having 1 to 20 carbon atoms, a substituted or unsubstituted aryl group having 6 to 50 carbon atoms, or a substituted or unsubstituted heterocyclic group having 3 to 50 ring atoms. $R^{62}$ and $R^{63}$ may bond to each other to form a ring.

In the general formula (11), $R^{51}$ to $R^{54}$ may be the same or different and are a hydrogen atom, a substituted or unsubstituted alkyl group having 1 to 20 carbon atoms, a substituted or unsubstituted aryl group having 6 to 50 carbon atoms, a substituted or unsubstituted heterocyclic group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 carbon atoms, or a cyano group. Adjacent groups of $R^{51}$ to $R^{54}$ may bond to each other to form a ring. $Y^1$ to $Y^4$ may be the same or different, and are —N=, —CH=, or $C(R^{55})$=. $R^{55}$ is a substituted or unsubstituted alkyl group having 1 to 20 carbon atoms, a substituted or unsubstituted aryl group having 6 to 50 carbon atoms, a substituted or unsubstituted heterocyclic group having 3 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 carbon atoms, or a cyano group.

The organic EL device of the invention may contain at least one of the anthracene derivative represented by the following formula (5-1) and the pyrene derivative represented by the following formula (5-2) in at least one layer of the organic thin film layers, preferably in the emitting layer. It is preferable that the emitting layer contain the anthracene derivative represented by the following formula (5-1) or the pyrene derivative represented by the following formula (5-2) as a host.

(Anthracene Derivative)

The anthracene derivative represented by the formula (5-1) is the following compound.

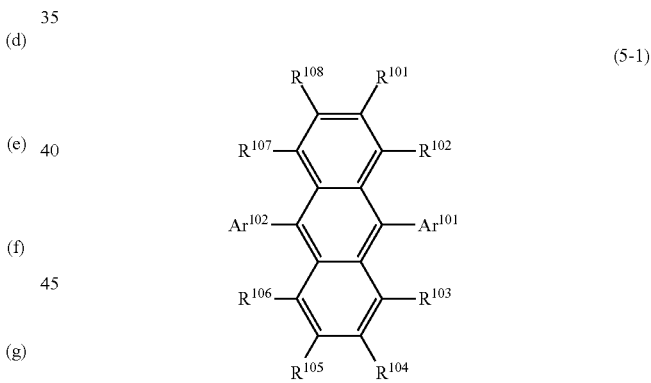

In the formula (5-1), $Ar^{101}$ and $Ar^{102}$ are independently a substituted or unsubstituted monocyclic group having 5 to 50 ring atoms, a substituted or unsubstituted condensed ring group having 8 to 50 ring atoms, or a group formed by combination of a monocyclic group and a condensed ring group and $R^{101}$ to $R^{108}$ are independently a group selected from a hydrogen atom, a substituted or unsubstituted monocyclic group having 5 to 50 ring atoms, a substituted or unsubstituted condensed ring group having 8 to 50 ring atoms, or a group formed by combination of a monocyclic group and a condensed ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom and a cyano group.

The monocyclic group in the formula (5-1) means a group which is composed of only ring structures having no condensed structure.

As specific examples of the monocyclic group having 5 to 50 (preferably 5 to 30, more preferably 5 to 20) ring atoms, aromatic groups such as a phenyl group, biphenyl group, terphenyl group and quaterphenyl group, and heterocyclic groups such as a pyridyl group, pyradyl group, pyrimidyl group, triadinyl group, furyl group and thienyl group, can be given preferably.

Among these, a phenyl group, biphenyl group or terphenyl group is more preferable.

The condensed ring group in the formula (5-1) means a group formed by condensation of 2 or more ring structures.

As specific examples of the condensed ring group having 8 to 50 (preferably 8 to 30, more preferably 8 to 20) ring atoms, condensed aromatic ring groups such as a naphthyl group, phenanthryl group, anthryl group, chrysenyl group, benzanthryl group, benzophenanthryl group, triphenylenyl group, benzochrysenyl group, indenyl group, fluorenylene group, 9,9-dimethylfluorenyl group, benzofluorenyl group, dibenzofluorenyl group, fluoranthenyl group and benzofluoranthenyl group, and condensed heterocyclic groups such as a benzofuranyl group, benzothiophenyl group, indolyl group, dibenzofuranyl group, dibenzothiophenyl group, carbazolyl group, quinolyl group and phenanthrolinyl group, can be given preferably.

Among these, a naphthyl group, phenanthryl group, anthryl group, 9,9-dimethylfluorenyl group, fluoranthenyl group, benzanthryl group, dibenzothiophenyl group, dibenzofuranyl group or carbazolyl group is more preferable.

The specific examples of the alkyl group, silyl group, cycloalkyl group and halogen atom in the formula (5-1) are the same as those of each group represented by $R^1$, $R^2$, $L^1$, $L^2$, $L^{11}$ to $L^{19}$ and $Ar^1$ to $Ar^{24}$ and substituents thereof in the above-mentioned formulas (1), (2) and (6) to (9).

The alkoxy group is represented by —OY. Examples for Y include those described above for the alkyl group. The alkoxy group is methoxy or ethoxy, for example.

The aryloxy group is represented by —OZ. Examples for Z include those described above for the aryl group. The aryloxy group is phenoxy, for example.

The aralkyl group is represented by —Y—Z. Examples for Y include alkylene corresponding to those described above for the alkyl group. Examples for Z include those described above for the aryl group. The aralkyl group is preferably an aralkyl group having 7 to 50 carbon atoms, wherein the aryl part has 6 to 49 (preferably 6 to 30, more preferably 6 to 20, still more preferably 1 to 10, particular preferably 6 to 12) carbon atoms, and the alkyl part has 1 to 44 (preferably 1 to 30, more preferably 1 to 20, particularly preferably 1 to 6) carbon atoms. For example, a benzyl group, phenylethyl group, or 2-phenylpropane-2-yl group can be given.

Only preferable specific examples in the formula (5-1) are given below.

As preferable substituents of "substituted or unsubstituted" $Ar^{101}$, $Ar^{102}$, and $R^{101}$ to $R^{108}$, a monocyclic group, condensed ring group, alkyl group, cycloalkyl group, silyl group, alkoxy group, cyano group and halogen atom (in particular, fluorine) can be given. A monocyclic group and condensed ring group are particularly preferable. The preferable specific examples are the same as those described in the above-mentioned formulas (5-1), (1), (2), and (6) to (9).

It is preferred that the anthracene derivative of the formula (5-1) be any of the following anthracene derivatives (A), (B) and (C), which is selected depending on the constitution or demanded properties of an organic EL device to which it is applied.

(Anthracene Derivative (A))

This anthracene derivative is derivatives of formula (5-1) wherein $Ar^{101}$ and $Ar^{102}$ are independently a substituted or unsubstituted condensed ring group having 8 to 50 ring carbon atoms. This anthracene derivative can be classified into the case that $Ar^{101}$ and $Ar^{102}$ are the same substituted or unsubstituted condensed ring group and the case that $Ar^{101}$ and $Ar^{102}$ are different substituted or unsubstituted condensed ring groups.

Particularly preferred is the anthracene derivative wherein $Ar^{101}$ and $Ar^{102}$ are different (including difference in substituted positions) substituted or unsubstituted condensed ring groups. Preferable specific examples of the condensed ring are the same as those described above. Among those, a naphthyl group, phenanthryl group, benzanthryl group, 9,9-dimethylfluorenyl group and dibenzofuranyl group are preferable.

(Anthracene Derivative (B))

This anthracene derivative is derivatives of formula (5-1) wherein one of $Ar^{101}$ and $Ar^{102}$ is a substituted or unsubstituted monocyclic group having 5 to 50 ring atoms, and the other is a substituted or unsubstituted condensed ring group having 8 to 50 ring atoms.

Preferable are anthracene derivatives wherein $Ar^{102}$ is a naphthyl group, phenanthryl group, benzanthryl group, 9,9-dimethylfluorenyl group or dibenzofuranyl group, and $Ar^{101}$ is a phenyl group substituted by a monocyclic group or condensed ring group.

Preferable specific examples of the monocyclic group and condensed ring group are the same as those described above.

Preferable also are anthracene derivatives wherein $Ar^{102}$ is a condensed ring group, and $A^{101}$ is an unsubstituted phenyl group. In this case, as the condensed ring group, a phenanthryl group, 9,9-dimethylfluorenyl group, dibenzofuranyl group and benzoanthryl group are particularly preferable.

(Anthracene Derivative (C))

This anthracene derivative is derivatives of formula (5-1) wherein $Ar^{101}$ and $Ar^{102}$ are independently a substituted or unsubstituted monocyclic group having 5 to 50 ring carbon atoms.

Preferable are anthracene derivatives wherein both $Ar^{101}$ and $Ar^{102}$ are a substituted or unsubstituted phenyl group.

Further preferable are anthracene derivatives wherein $Ar^{101}$ is an unsubstituted phenyl group, and $Ar^{102}$ is a phenyl group having a monocyclic group and condensed ring group as a substitutent, and anthracene derivatives wherein $Ar^{101}$ and $Ar^{102}$ are independently a phenyl group having a monocyclic group and condensed ring group as a substitutent.

The preferable specific examples of the monocyclic group and condensed ring group as a substituent are the same as those described above. As the monocyclic group as a substituent, a phenyl group and biphenyl group are more preferable. As the condensed ring group as a substituent are a naphthyl group, phenanthryl group, 9,9-dimethylfluorenyl group, dibenzofuranyl group and benzanthryl group are more preferable.

(Pyrene Derivative)

The pyrene derivative represented by the formula (5-2) is the following compound.

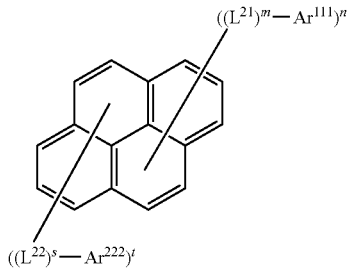

(5-2)

wherein $Ar^{111}$ and $Ar^{222}$ are independently a substituted or unsubstituted aryl group having 6 to 30 ring carbon atoms;

$L^{21}$ and $L^{22}$ are independently a substituted or unsubstituted divalent aryl group or heterocyclic group having 6 to 30 ring carbon atoms;

m is an integer of 0 to 1, n is an integer of 1 to 4, s is an integer of 0 to 1, and t is an integer of 0 to 3; and $L^{21}$ or $Ar^{111}$ bonds at any one position of 1 to 5 of the pyrene, and $L^{22}$ or $Ar^{222}$ bonds at any one position of 6 to 10 of the pyrene.

$L^{21}$ and $L^{22}$ in the general formula (5-2) are preferably a divalent aryl group composed of a substituted or unsubstituted phenylene group, a substituted or unsubstituted biphenylene group, a substituted or unsubstituted naphthylene group, a substituted or unsubstituted terphenylene group, a substituted or unsubstituted fluorenylene group, or a combination of these substituents.

These substituents are the same as those of "substituted or unsubstituted" described above. The substituents of $L^{21}$ and $L^{22}$ are preferably an alkyl group having 1 to 20 carbon atoms.

m in the general formula (5-2) is preferably an integer of 0 to 1. n in the general formula (5-2) is preferably an integer of 1 to 2. s in the general formula (5-2) is preferably an integer of 0 to 1.

t in the general formula (5-2) is preferably an integer of 0 to 2.

The aryl groups of $Ar^{111}$ and $Ar^{222}$ are the same as those described above.

Preferable aryl groups are a substituted or unsubstituted aryl group having 6 to 20 ring carbon atoms, with a substituted or unsubstituted aryl group having 6 to 16 ring carbon atoms being more preferable. Preferable specific examples of the aryl groups include a phenyl group, naphthyl group, phenanthryl group, fluorenyl group, biphenyl group, anthryl group and pyrenyl group.

The emitting layer may contain a luminous dopant (phosphorescent dopant and/or fluorescent dopant) in addition to an emitting material.

The fluorescent dopant is a compound which can emit light from singlet excitons. It is preferred that the fluorescent dopant be selected from amine compounds, aromatic compounds, chelate complexes such as tris(8-quinolinato)aluminum complex, coumalin derivatives, tetraphenylbutadiene derivatives, bisstyrylarylene derivatives, oxadiazole derivatives and the like depending on demanded emitting color. More preferable are styrylamine compounds, styryldiamine compounds, arylamine compounds and aryldiamine compounds. Still more preferable is condensed polycyclic amine derivatives. These fluorescent dopants can be used singly or in combination thereof.

Preferable are condensed polycyclic amine derivatives represented by the following formula (12).

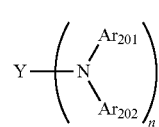

(12)

wherein Y is a substituted or unsubstituted condensed aryl group having 10 to 50 ring carbon atoms; and $Ar_{201}$ and $Ar_{202}$ are independently a substituted or unsubstituted aryl group having 6 to 50 ring carbon atoms or a substituted or unsubstituted heterocyclic group having 5 to 50 ring atoms.

The condensed aryl group is an aryl group formed by condensation of 2 or more ring structures among the above-mentioned aryl groups.

The condensed aryl group is a condensed aryl group having 10 to 50 (preferably 10 to 30, more preferably 10 to 20) ring carbon atoms. Among the specific examples of aryl group mentioned above, preferable are naphthyl, anthryl, pyrenyl, phenanthryl, fluorenyl, fluorantenyl and naphtacenyl, etc.

Specific Examples of Y include the condensed aryl groups described above. Preferable are a substituted or unsubstituted anthryl group, a substituted or unsubstituted pyrenyl group, and a substituted or unsubstituted chrysenyl group.

Preferable examples of $Ar_{201}$ and $Ar_{202}$ include a substituted or unsubstituted phenyl group and a substituted or unsubstituted dibenzofuranyl group. Preferable examples of the substituent of $Ar_{201}$ and $Ar_{202}$ include an alkyl group, a cyano group, and a substituted or unsubstituted silyl group.

n is an integer of 1 to 4. n is preferably an integer of 1 to 2.

As the styrylamine compounds and styryldiamine compounds, the compounds represented by the following formulas (17) and (18) are preferable.

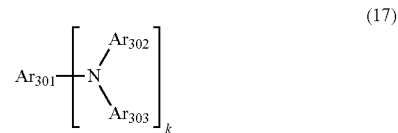

(17)

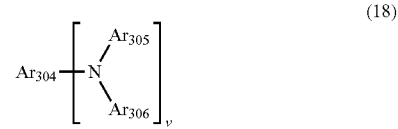

(18)

wherein $Ar_{301}$ is a k-valent group which corresponds to phenyl, naphthyl, biphenyl, terphenyl, stilbene, styrylaryl, or distyrylaryl. $Ar_{302}$ and $Ar_{303}$ are independently an aryl group having 6 to 20 ring carbon atoms. $Ar_{301}$, $Ar_{302}$ and $Ar_{303}$ may be substituted.

k is an integer of 1 to 4. k is preferably an integer of 1 to 2. Any one of $Ar_{301}$ to $Ar_{303}$ is a group containing a styryl group. At least one of $Ar_{302}$ and $Ar_{303}$ is more preferably substituted with a styryl group.

Here, as the aryl group having 6 to 20 ring carbon atoms, the above-mentioned aryl groups can be given specifically. Among these, a phenyl group, naphthyl group, anthranil group, phenanthryl group, terphenyl group and the like are preferable.

Ar$_{304}$ to Ar$_{306}$ in the formula (18) is a substituted or unsubstituted v-valent aryl group having 6 to 40 ring carbon atoms. v is an integer of 1 to 4. Among these, v is preferably an integer of 1 to 2.

Here, as the aryl group having 6 to 40 ring carbon atoms in the formula (18), the above-mentioned aryl groups can be given specifically. Preferable is a naphthyl group, anthranil group, crysenyl group or pyrenyl group.

Preferable substituents of the aryl group include an alkyl group having 1 to 6 carbon atoms, an alkoxy group having 1 to 6 carbon atoms, an aryl group having 6 to 40 ring carbon atoms, an amino group substituted with an aryl group having 6 to 40 ring carbon atoms, an ester group having an aryl group having 5 to 40 ring carbon atoms, an ester group having an alkyl group having 1 to 6 carbon atoms, a cyano group, a nitro group and a halogen atom.

The phosphorescent dopant is a compound of which the optical energy can be deactivated from the lowest excited triplet state at normal temperature.

The phosphorescent dopant includes a metal complex. It is preferred that the metal complex have a metal atom selected from Ir, Pt, Os, Au, Cu, Re and Ru, and a ligand. In particular, the ligand has preferably an ortho metal bonding.

It is preferred that the phosphorescent dopant be a compound containing a metal atom selected from Ir, Os and Pt in view of high phosphorescent quantum yield and more improved external quantum efficiency of the light emitting device. More preferable are a metal complex such as an iridium complex, osmium complex and platinum complex. In particular, an iridium complex and platinum complex are more preferable, and an ortho metalated iridium complex is most preferable.

Specific examples of preferable metal complex are shown below.

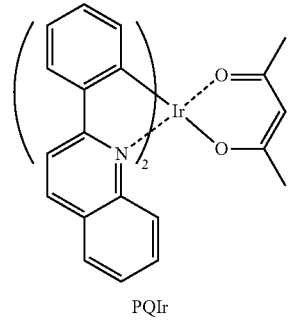

PQIr

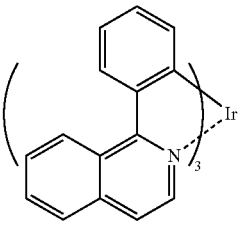

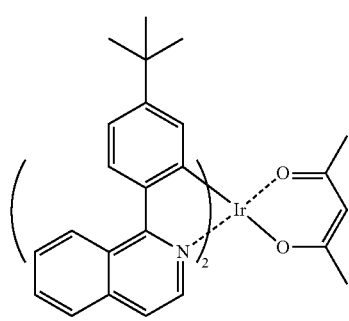

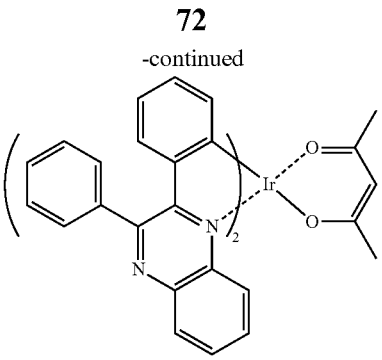

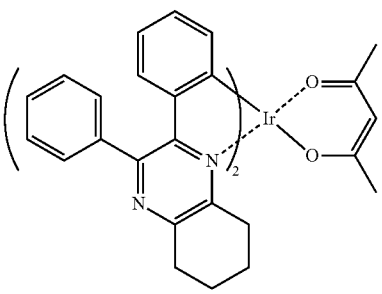

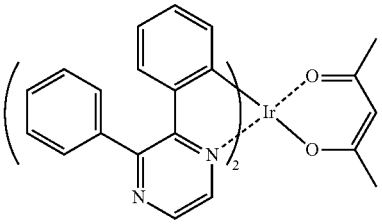

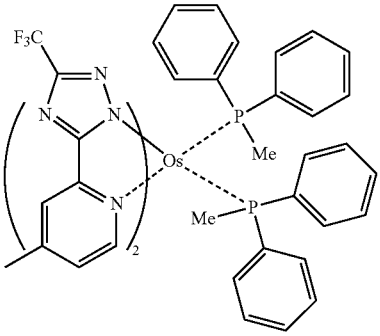

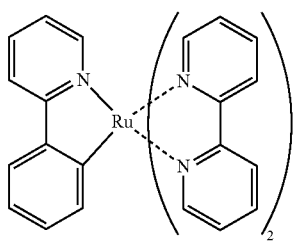

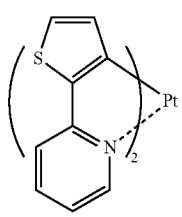

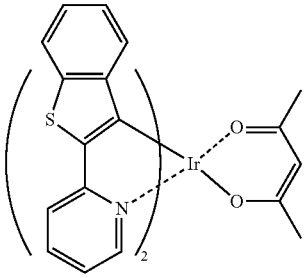

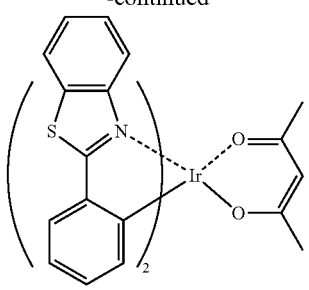
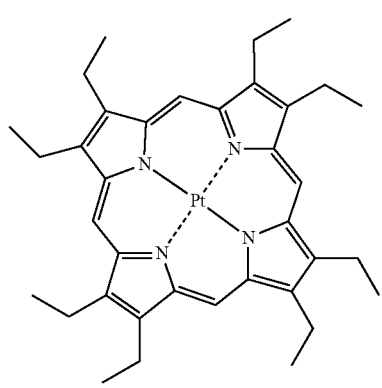
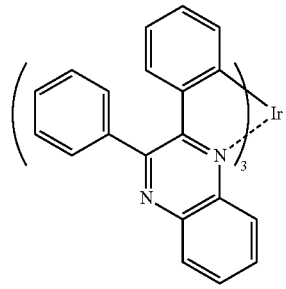
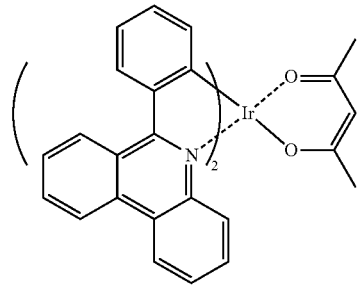
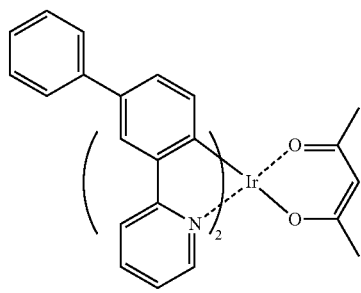
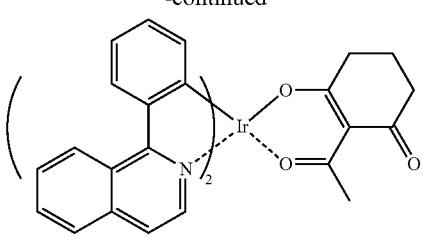
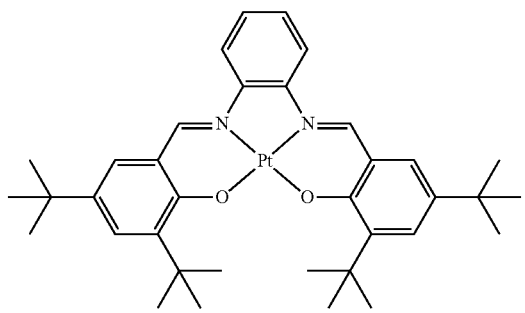
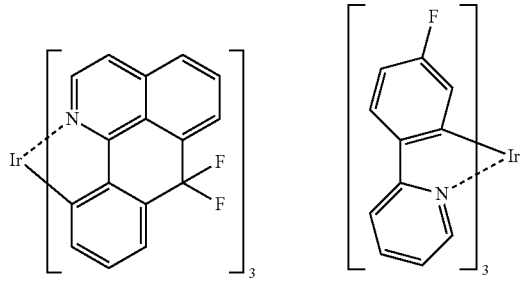
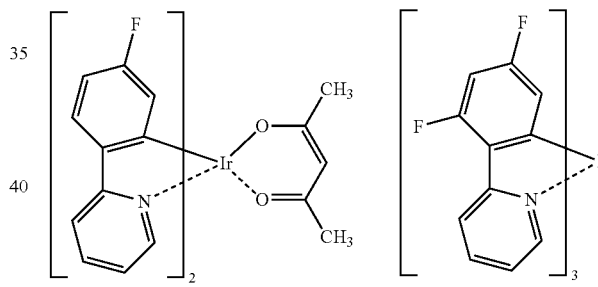
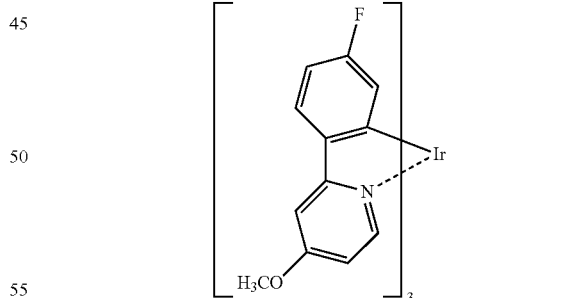
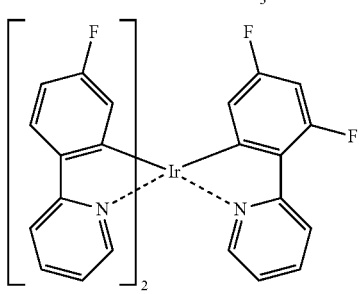

75
-continued
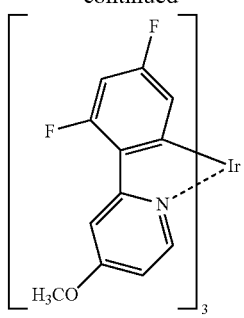
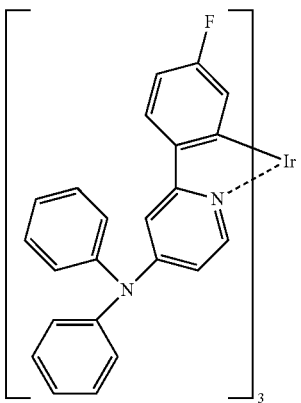
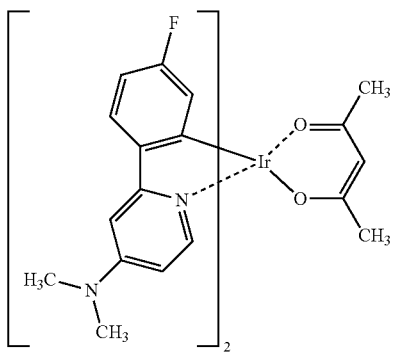
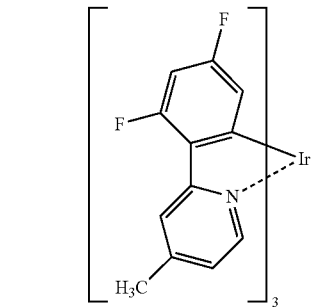
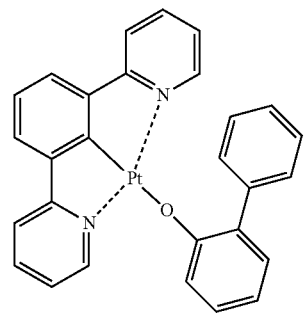 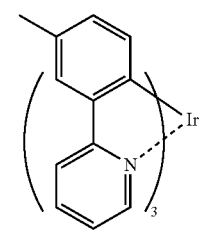
76
-continued
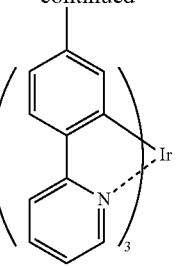
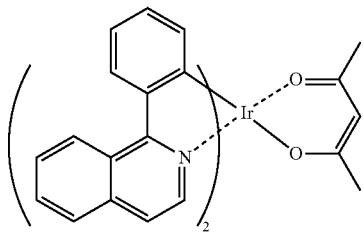
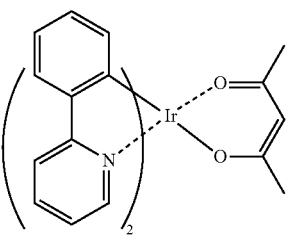
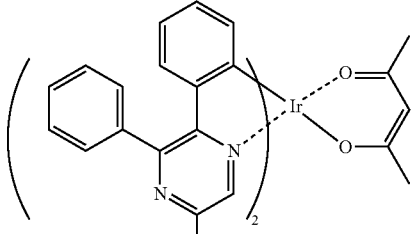
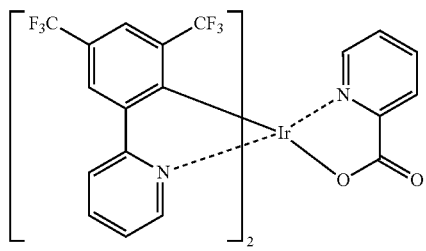
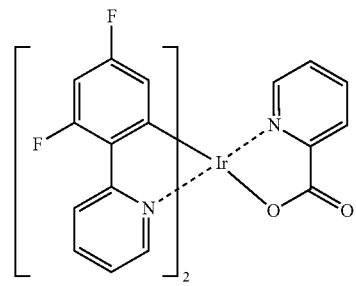

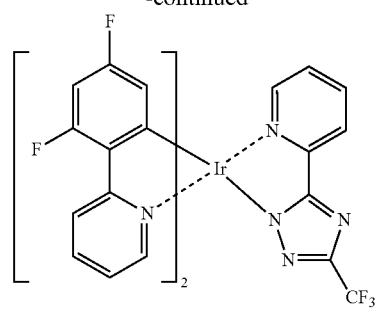
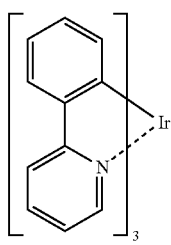
Ir(ppy)₃
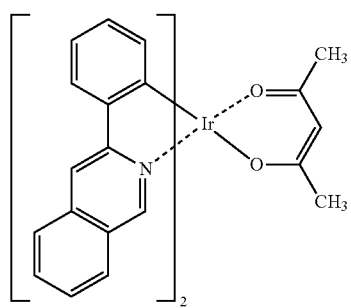
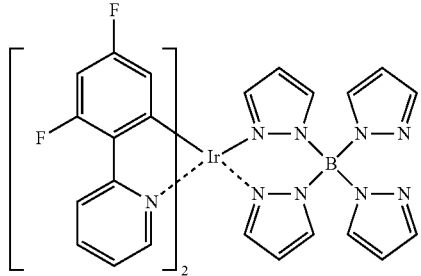
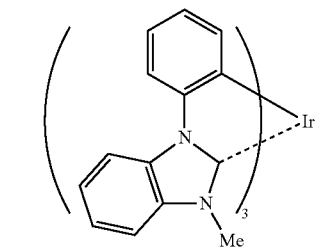
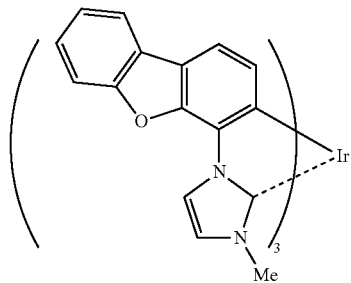
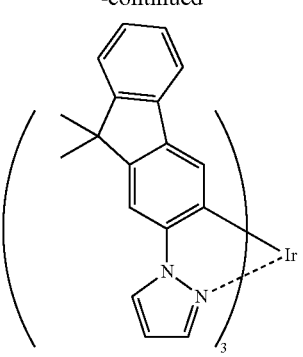
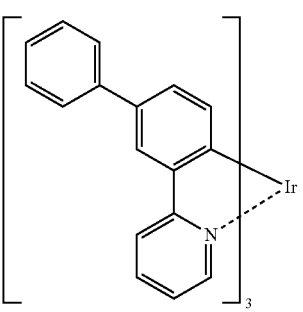
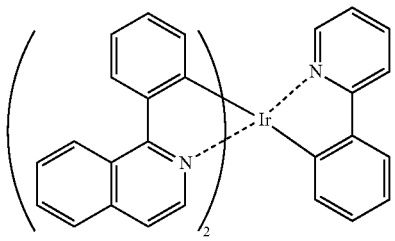
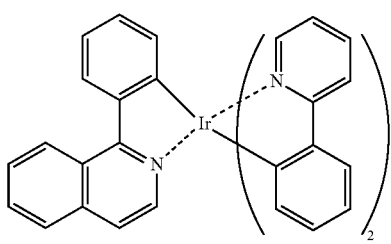
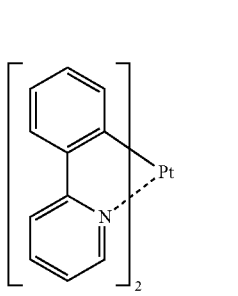
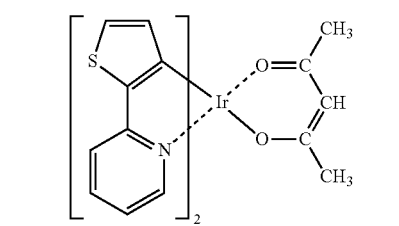

-continued

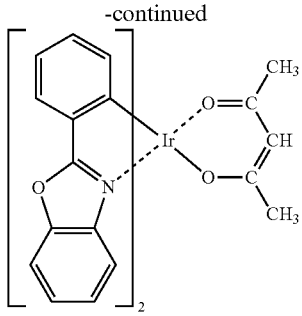

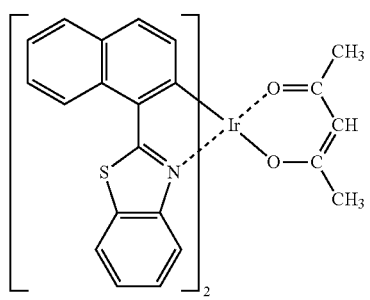

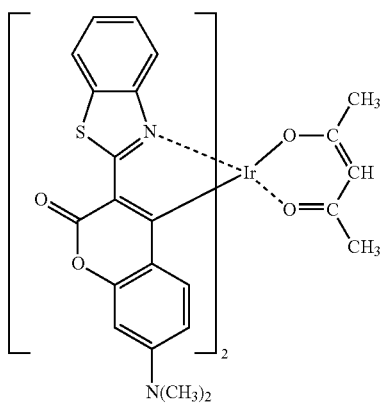

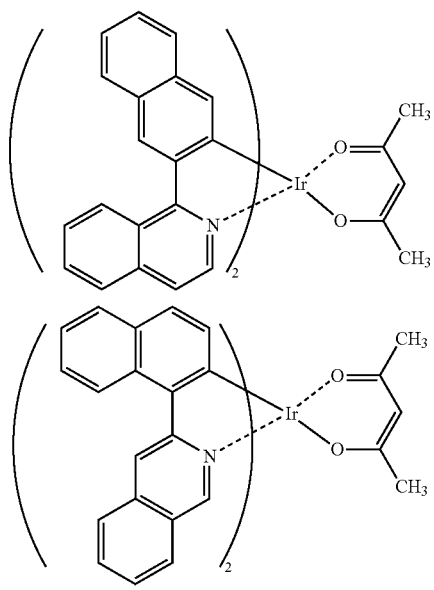

-continued

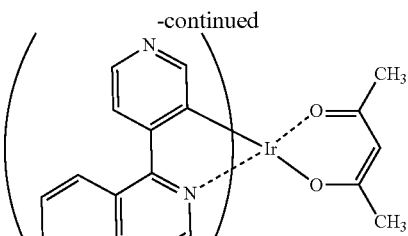

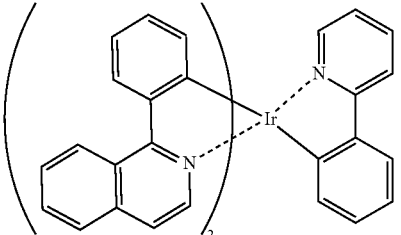

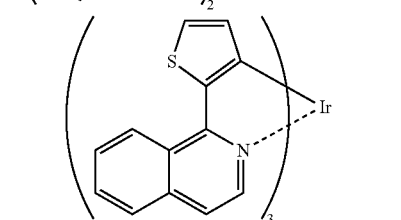

Preferable electron-injecting•transporting material is a compound which can transport electrons, into which a cathode injects electrons, and which excellently injects electrons into an emitting layer or emitting material, and exhibits an excellent thin-film forming ability.

In the organic EL device of the invention, more effective electron-injecting material is a metal complex compound and a nitrogen-containing heterocyclic derivative.

Examples of the metal complex compound include 8-hydroxyquinolinatelithium, bis(8-hydroxyquinolinato)zinc, tris(8-hydroxyquinolinato)aluminum, tris(8-hydroxyquinolinato)gallium, bis(10-hydroxybenzo[h]quinolinato)beryllium and bis(10-hydroxybenzo[h]quinolinato)zinc. However, it is not limited to these.

Preferable examples of the nitrogen-containing heterocyclic derivative include oxazole, thiazole, oxadiazole, thiadiazole, triazole, pyridine, pyrimidine, triazine, phenanthroline, benzimidazole and imdazopyridine. Among these, benzimidazole derivatives, phenanthroline derivatives and imidazopyridine derivatives are preferable.

In a preferable organic EL device of the invention, a dopant is also contained in these electron-injecting materials. It is more preferred that the neighborhood of the interface between a second organic layer and cathode be doped with a dopant represented by an alkali metal in order to facilitate accepting of electrons from the cathode.

As the dopant, a donor metal, donor metal compound and donor metal complex can be given. These reducing dopants can be used singly or in combination of two or more.

For the members such as a substrate, an anode and a cathode of the organic EL device, in addition to those described above, it is possible to select appropriately and use known materials described in documents such as WO2009/107596A1, WO2009/081857A1, US2009/0243473A1, US2008/0014464A1 and US2009/0021160A1.

EXAMPLES
The structures of immediate produced in Synthesis Examples 1 to 14 are as follows:
Intermediate 1
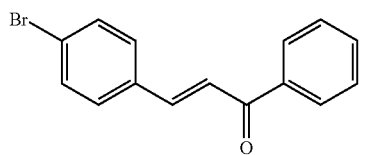
Intermediate 2
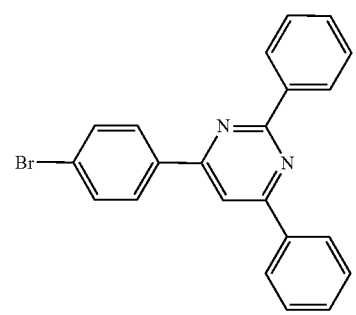
Intermediate 3
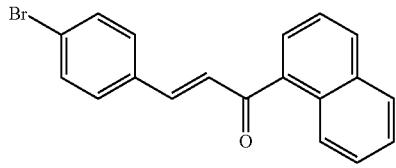
Intermediate 4
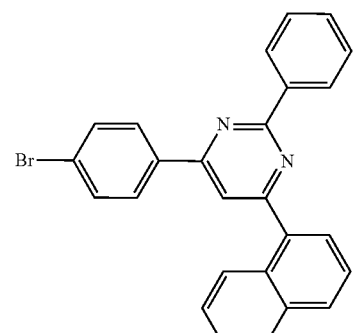
Intermediate 5
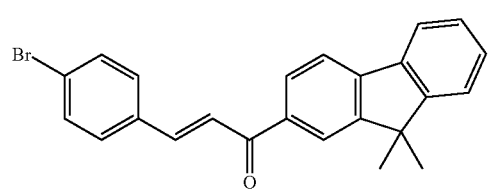
Intermediate 6
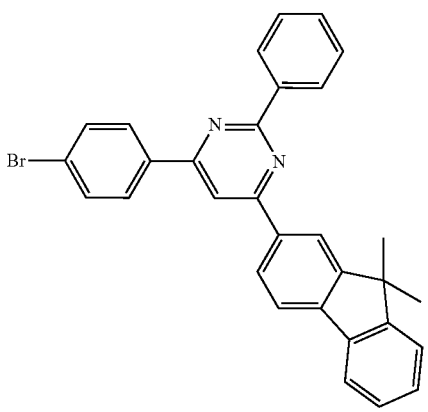
Intermediate 7
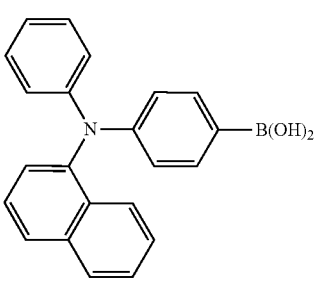
Intermediate 8
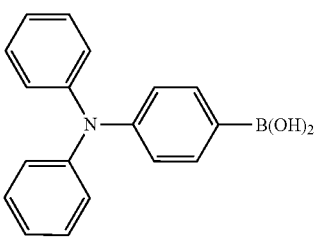
Intermediate 9
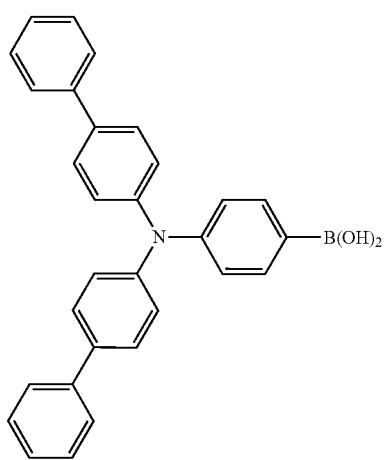

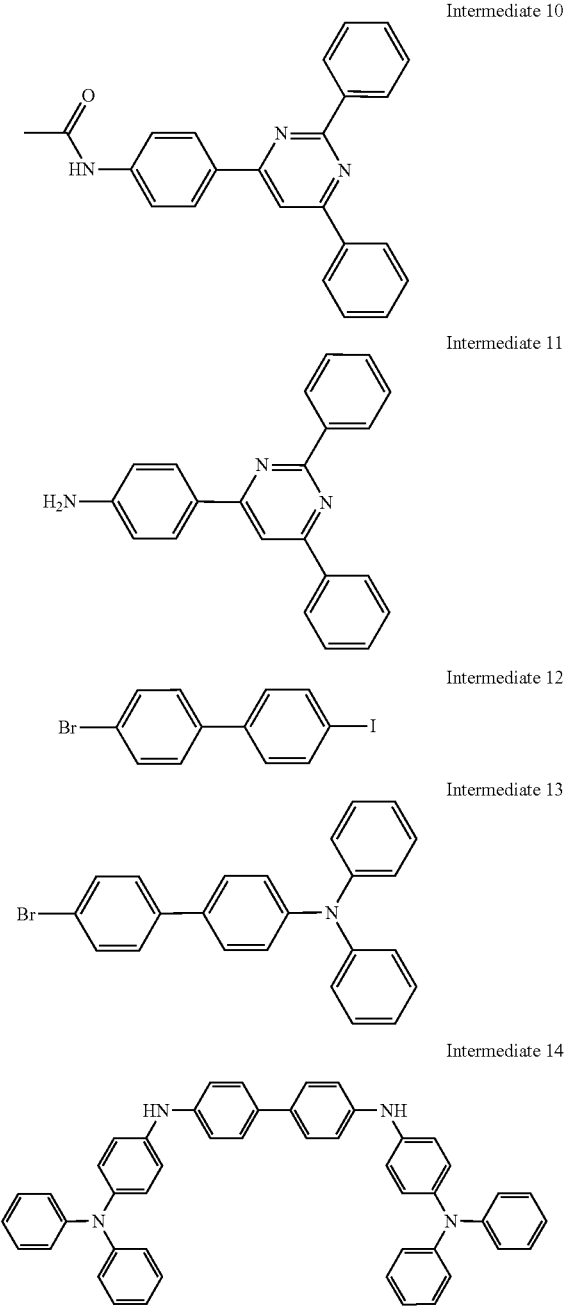

Synthesis Example 1

Synthesis of Intermediate 1

4-bromobenzaldehyde (25 g, 135 mmol) and acetophenone (16.2 g, 135 mmol) were added to ethanol (200 mL) and a 3M aqueous solution of potassium hydroxide (60 mL) was further added. The mixture was stirred at room temperature for 7 hours. The precipitates were separated by filtration and washed with methanol to obtain white solids (28.3 g, yield 73%). The solids were identified as Intermediate 1 by FD-MS analysis.

Synthesis Example 2

Synthesis of Intermediate 2

Intermediate 1 (20 g, 69.7 mmol) and benzamidine hydrochloride (10.8 g, 69.7 mmol) were added to ethanol (300 mL) and sodium hydroxide (5.6 g, 140 mmol) was further added. The mixture was heated under reflux for 8 hours. The precipitates were separated by filtration and washed with hexane to obtain white solids (10.3 g, yield 38%). The solids were identified as Intermediate 2 by FD-MS analysis.

Synthesis Example 3

Synthesis of Intermediate 3

Reaction was conducted in a similar way to Synthesis Example 1 except that 23.0 g of 1-acetylnaphthalene was used instead of acetophenone to obtain 34.1 g of white powder (yield 75%). The powder was identified as Intermediate 3 by FD-MS analysis.

Synthesis Example 4

Synthesis of Intermediate 4

Reaction was conducted in a similar way to Synthesis Example 2 except that 23.5 g of Intermediate 3 was used instead of Intermediate 1 to obtain 10.7 g of white powder (yield 35%). The powder was identified as Intermediate 4 by FD-MS analysis.

Synthesis Example 5

Synthesis of Intermediate 5

Reaction was conducted in a similar way to Synthesis Example 1 except that 31.9 g of 2-acetyl-9,9-dimethylfluorene was used instead of acetophenone to obtain 39.2 g of white powder (yield 72%). The powder was identified as Intermediate 5 by FD-MS analysis.

Synthesis Example 6

Synthesis of Intermediate 6

Reaction was conducted in a similar way to Synthesis Example 2 except that 28.2 g of Intermediate 5 was used instead of Intermediate 1 to obtain 14.4 g of white powder (yield 41%). The powder was identified as Intermediate 6 by FD-MS analysis.

Synthesis Example 7

Synthesis of Intermediate 7

11.1 g of N-phenyl-1-naphthylamine, 15.6 g of 4-iodobromobenzene, 1.9 g of copper(I)iodide, 2.0 g of N,N'-dimethylethylenediamine, 8.6 g of sodium tert-butoxide and 100 mL of dehydrated toluene were placed in a 300 mL three-necked flask under a flow of argon. The mixture was stirred at 110° C. for 8 hours. After the reaction was completed, the resultant was extracted with toluene and then dried with magnesium sulfate. The extract was condensed under reduced pressure, and the crude product obtained was purified using column chromatography. The purified substance was recrystallized with toluene, filtered out and dried to obtain 16.8 g of white powder.

16.8 g of the above-mentioned white powder and 100 mL of dehydrated xylene were placed in a 300 mL three-necked flask under a flow of argon, and cooled to −30° C. 30 mL of n-butyllithium (1.6M hexane solution) was added thereto and reacted for an hour. After cooled to −70° C., 28 mL of triisopropyl borate was added. After heated slowly, the mixture was stirred at room temperature for an hour. 32 mL of 10% hydrochloric acid solution was added and stirred. The mixture was extracted with ethyl acetate and water, and the organic layer was washed with water. The resultant was dried with anhydrous sodium sulfate and the solvent was distilled away. The resultant was washed with hexane to obtain 7.5 g of white powder.

Synthesis Example 8

Synthesis of Intermediate 8

Reaction was conducted in a similar way to Synthesis Example 7 except that 8.6 g of diphenylamine was used instead of N-phenyl-1-naphthylamine to obtain 6.6 g of white powder.

Synthesis Example 9

Synthesis of Intermediate 9

Reaction was conducted in a similar way to Synthesis Example 7 except that 16.3 g of N,N-bisbiphenylamine was used instead of N-phenyl-1-naphthylamine to obtain 10.0 g of white powder.

Synthesis Example 10

Synthesis of Intermediate 10

18.5 g of 1-acetamide, 38.7 g of Intermediate 2, 54.4 g of potassium carbonate, 1.3 g of copper powder and 200 mL of decalin were mixed under an argon atmosphere. The mixture was stirred at 190° C. for 4 days. After the reaction was completed, the mixture was cooled and 200 mL of toluene was added, and then insoluble matters were filtered out. The filtered matters were solved in 450 mL of chloroform. After removing insoluble matters, the remaining solution was subjected to an activated carbon treatment, and condensed. 300 mL of acetone was added thereto to precipitate a crystal. The crystal was filtered out to obtain 17.5 g of a white crystal. The crystal was identified as Intermediate 10 by FD-MS analysis.

Synthesis Example 11

Synthesis of Intermediate 11

In a 300 mL three-necked flask, 17.5 g of Intermediate 10 was suspended in 500 mL of ethylene glycol and 5 mL of water. After adding 21 g of 85% potassium hydroxide solution, the mixture was stirred at 120° C. for 8 hours. After the reaction was completed, the reaction solution was added to 1 L of water, a precipitated crystal was filtered out and then washed with water and methanol. The crystal obtained was solved in 300 mL of tetrahydrofuran while heating. The solution was subjected to an activated carbon treatment, and then condensed. A crystal was precipitated by adding acetone. The crystal was filtered out to obtain 14.5 g of white powder. The white powder was identified as Intermediate 11 by FD-MS analysis.

Synthesis Example 12

Synthesis of Intermediate 12

47 g of 4-bromobiphenyl, 23 g of iodine, 9.4 g of periodic acid 2-hydrate, 42 mL of water, 360 mL of acetic acid and 11 mL of sulfuric acid were placed in a 1000 mL three-necked flask under a flow of argon. After stirring at 65° C. in 30 minutes, the mixture was stirred at 90° C. for 6 hours. The resultant mixture was poured into iced water, and then filtrated. The filtrated matters were washed with water and then methanol to obtain 67 g of white powder. The white powder was identified as Intermediate 12 by FD-MS analysis.

Synthesis Example 13

Synthesis of Intermediate 13

5.1 g of diphenylamine, 10.8 g of Intermediate 12, 3 g of sodium tert-butoxide (manufactured by HIROSHIMA WAKO CO., LTD.), 0.5 g of bis(triphenylphosphine) palladium (II) chloride (manufactured by TOKYO CHEMICAL INDUSTRY CO., LTD.) and 500 mL of xylene were mixed under a flow of argon. The mixture was stirred at 130° C. for 24 hours.

After cooling, 1000 mL of water was added thereto, the mixture was celite-filtrated. The filtrate was extracted with toluene and then dried with anhydrous magnesium sulfate. This was condensed under reduced pressure, and the crude product obtained was purified using column chromatography. The purified matters were recrystallized with toluene, filtered out and dried to obtain 3.4 g of pale yellow powder. The pale yellow powder was identified as Intermediate 13 by FD-MS analysis.

Synthesis Example 14

Synthesis of Intermediate 14

25.8 g of diphenylamine, 46.8 g of 4-iodobromobenzene, 5.7 g of copper (I) iodide, 6.0 g of N,N'-dimethylethylenediamine, 25.8 g of sodium tert-butoxide and 300 mL of dehydrated toluene were placed in a 300 mL three-necked flask under a flow of argon. The mixture was stirred at 110° C. for 8 hours. After the reaction was completed, the resultant was extracted with toluene and then dried with magnesium sulfate. The extract was condensed under reduced pressure, and the crude product obtained was purified using column chromatography. The purified matters were recrystallized with toluene, filtered out and dried to obtain 43.8 g of white powder.

32.4 g of the above-mentioned white powder, 18.5 g of 1-acetamide, 54.4 g of potassium carbonate, 1.3 g of copper powder and 200 mL of decalin were mixed under an argon atmosphere. The mixture was stirred at 190° C. for 4 days. After the reaction was completed, the resultant was cooled and 200 mL of toluene was added, and then insoluble matters were filtered out. The filtrated matters were solved in 450 mL of chloroform. After removing insoluble matters, the remaining solution was subjected to an activated carbon treatment, and condensed. 300 mL of acetone was added thereto to precipitate a crystal. The crystal was filtered out to obtain 17.5 g of crystal.

To this crystal, 12 g of 4,4'-diiodobiphenyl, 16.3 g of potassium carbonate, 0.4 g of copper powder and 60 mL of decalin were added. The mixture was stirred at 190° C. for 4 days. After the reaction was completed, the mixture was cooled. 60 mL of toluene was added and then insoluble matters were filtered out. The filtrated matters were solved in 140 mL of chloroform. After removing insoluble matters, the remaining solution was subjected to an activated carbon treatment, and condensed. 100 mL of acetone was added thereto to precipitate a crystal. The crystal was filtered out to obtain 38.2 g of crystal.

This filtrated crystal was suspended in 150 mL of ethylene glycol and 1.5 mL of water. After adding 4.4 g of 85% potassium hydroxide solution, the mixture was stirred at 120° C. for 8 hours. After the reaction was completed, the reaction solution was added to 1 L of water, a precipitated crystal was filtered out and then washed with water and methanol. The crystal obtained was solved in 100 mL of tetrahydrofuran while heating. The solution was subjected to an activated carbon treatment, and condensed. A crystal was precipitated by adding acetone. The crystal was filtered out to obtain 13 g of white powder. The white powder was identified as Intermediate 14 by FD-MS analysis.

The structures of the aromatic amine derivatives according to the invention prepared in Examples 1 to 10 are as follows:

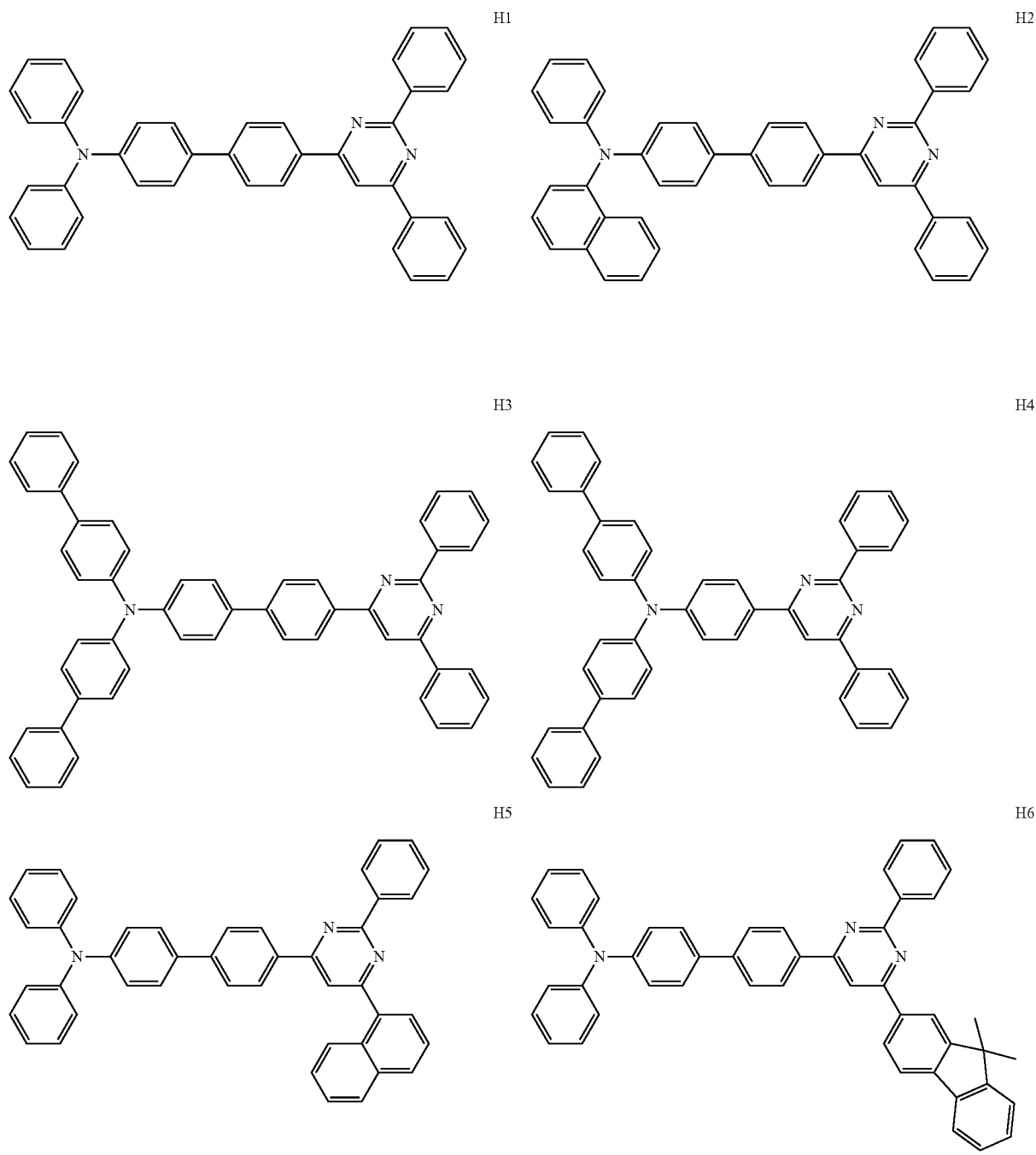

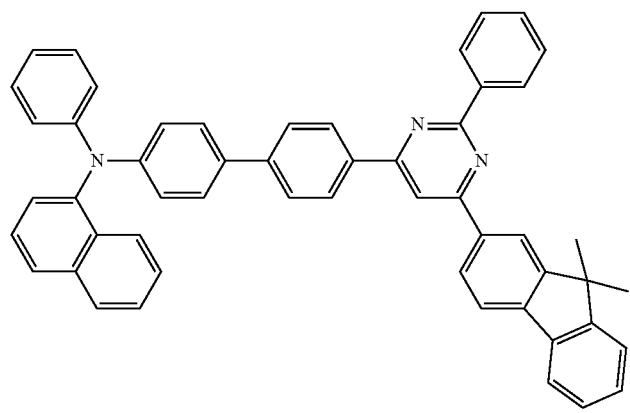
H7
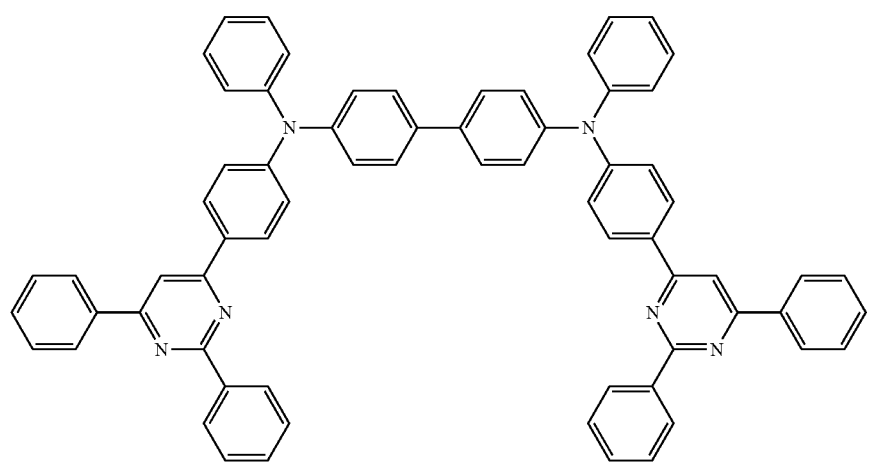
H8
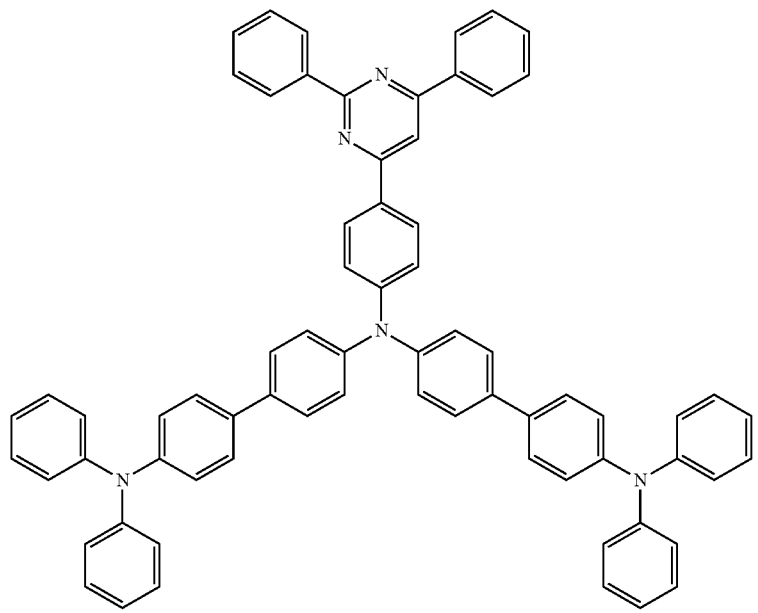
H9

-continued

H10

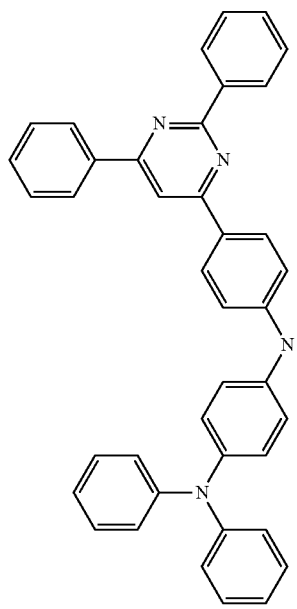
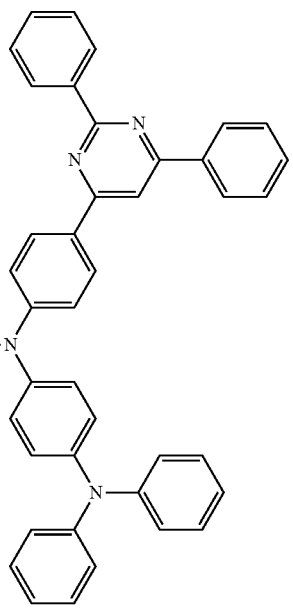

Example 1

Preparation of Aromatic Amine Derivative (H1)

Intermediate 8 (2.9 g, 10.0 mmol), Intermediate 2 (3.9 g, 10.0 mmol), Pd(PPH$_3$)$_4$ (0.21 g, 0.2 mmol), toluene (30 mL) and a 2M aqueous solution of potassium hydroxide (15 mL) were mixed under an argon atmosphere. The mixture was stirred at 80° C. for 7 hours. Water was added to the reaction solution to precipitate solid matters. The solid matters were washed with methanol. The solid matters obtained were filtrated and washed with heated toluene, and then dried to obtain 3.8 g of pale yellow powder. The pale yellow powder was identified as Aromatic amine derivative (H1) by FD-MS analysis.

Example 2

Preparation of Aromatic Amine Derivative (H2)

Reaction was conducted in a similar way to Example 1 except that 3.4 g of Intermediate 7 was used instead of Intermediate 8 to obtain 4.3 g of pale yellow powder. The pale yellow powder was identified as Aromatic amine derivative (H2) by FD-MS analysis.

Example 3

Preparation of Aromatic Amine Derivative (H3)

Reaction was conducted in a similar way to Example 1 except that 4.4 g of Intermediate 9 was used instead of Intermediate 8 to obtain 4.8 g of pale yellow powder. The pale yellow powder was identified as Aromatic amine derivative (H3) by FD-MS analysis.

Example 4

Preparation of Aromatic Amine Derivative (H4)

3.2 g of di-4-biphenylamine, 3.9 g of Intermediate 2, 1.3 g of sodium tert-butoxide, 46 mg of tris(dibenzylideneacetone) dipalladium, 21 mg of tri-tert-butylphosphine and 50 mL of dehydrated toluene were mixed under an argon atmosphere. The mixture was stirred at 80° C. for 2 hours.

After cooling, 500 mL of water was added thereto, the mixture was celite-filtrated. The filtrate was extracted with toluene and then dried with anhydrous magnesium sulfate. The extract was condensed under reduced pressure, and the crude product obtained was purified using column chromatography. The purified matters were recrystallized with toluene, filtered out and dried to obtain 4.2 g of pale yellow powder. The pale yellow powder was identified as Aromatic amine derivative (H4) by FD-MS analysis.

Example 5

Preparation of Aromatic Amine Derivative (H5)

Reaction was conducted in a similar way to Example 1 except that 4.4 g of Intermediate 4 was used instead of Intermediate 2 to obtain 4.0 g of pale yellow powder. The pale yellow powder was identified as Aromatic amine derivative (H5) by FD-MS analysis.

Example 6

Preparation of Aromatic Amine Derivative (H6)

Reaction was conducted in a similar way to Example 1 except that 5.0 g of Intermediate 6 was used instead of Intermediate 2 to obtain 4.3 g of pale yellow powder. The pale yellow powder was identified as Aromatic amine derivative (H6) by FD-MS analysis.

Example 7

Preparation of Aromatic Amine Derivative (H7)

Reaction was conducted in a similar way to Example 1 except that 5.0 g of Intermediate 6 was used instead of Intermediate 2 and 3.4 g of Intermediate 7 was used instead of Intermediate 8 to obtain 4.6 g of pale yellow powder. The pale yellow powder was identified as Aromatic amine derivative (H7) by FD-MS analysis.

Example 8

Preparation of Aromatic Amine Derivative (H8)

Reaction was conducted in a similar way to Example 4 except that 7.7 g of Intermediate 2 was used and 3.4 g of N,N'-diphenylbenzidine was used instead of di-4-biphenylylamine to obtain 6.2 g of pale yellow powder. The pale yellow powder was identified as Aromatic amine derivative (H8) by FD-MS analysis.

Example 9

Preparation of Aromatic Amine Derivative (H9)

Reaction was conducted in a similar way to Example 4 except that 8.0 g of Intermediate 13 was used instead of Intermediate 2 and 3.2 g of Intermediate 11 was used instead of di-4-biphenylylamine to obtain 6.0 g of pale yellow powder. The pale yellow powder was identified as Aromatic amine derivative (H9) by FD-MS analysis.

Example 10

Preparation of Aromatic Amine Derivative (H10)

Reaction was conducted in a similar way to Example 4 except that 7.7 g of Intermediate 2 was used and 6.7 g of Intermediate 14 was used instead of di-4-biphenylylamine to obtain 7.2 g of pale yellow powder. The pale yellow powder was identified as Aromatic amine derivative (H10) by FD-MS analysis.

Example 1-1

Production of Organic EL Device

A glass substrate of 25 mm by 75 mm by 1.1 mm thick with an ITO transparent electrode (GEOMATEC CO., LTD.) was subjected to ultrasonic cleaning in isopropyl alcohol for 5 minutes, and cleaning with ultraviolet rays and ozone for 30 minutes.

The resultant substrate with transparent electrode lines was mounted on a substrate holder in a vacuum deposition device. First, the following electron-acceptor compound (C-1) was deposited to form a 10 nm-thick C-1 film so as to cover the surface of the transparent electrode on which the transparent electrode lines were formed. The aromatic amine derivative (H1) obtained in Synthesis Example 1 was deposited as a hole-transporting material on the C-1 film to form a 70 nm-thick hole-transporting layer. The following compound EM1 was deposited to form a 40 nm-thick emitting layer. Simultaneously, the following styrylamine derivative (D1) was deposited as a luminescent molecule such that the weight ratio of EM1 and D1 (EM1:D1) became 40:2.

The following organic metal complex (Alq) was formed to a 10 nm-thick film thereon. The film functioned as an electron-injecting layer. Then, Li as a reductive dopant (Li source: manufactured by SAES Getters Co., Ltd.) and Alq were co-deposited, whereby an Alq:Li film (film thickness: 10 nm) was formed as an electron-injecting layer (cathode). Metal aluminum was deposited on the Alq:Li film to form a metallic cathode, whereby an organic EL device was fabricated.

The color of light emitted from the organic EL device thus obtained was observed and the device was measured for luminous efficiency, driving voltage and half life at a 5000 cd/m² of initial luminance at room temperature by constant current driving. Table 1 shows the results.

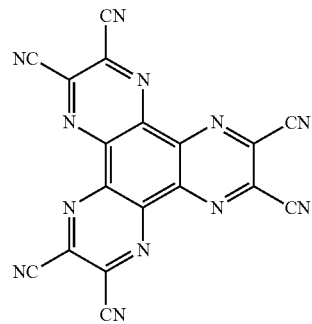

Electron-acceptor compound (C-1)

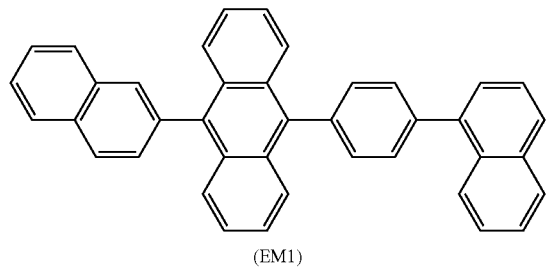

(EM1)

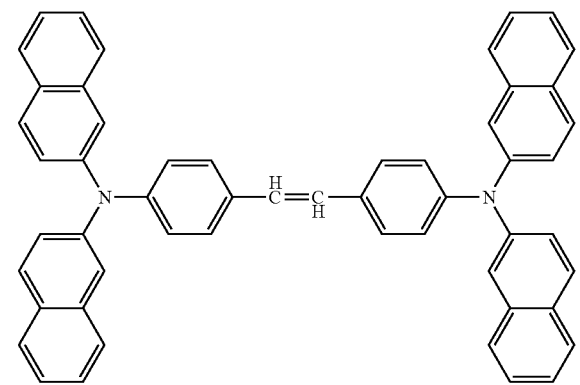

Styrylamine derivative (D1)

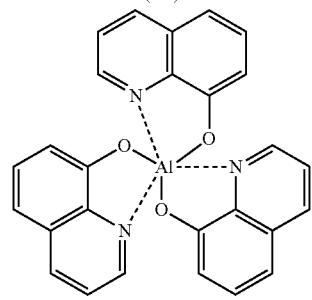

Organic metal complex (Alq)

Example 1-2

Production of Organic EL Device

An organic EL device was produced in the same manner as in Example 1-1, except that Aromatic amine derivative (H2) was used instead of Aromatic amine derivative (H1) as the hole-transporting material.

The color of light emitted from the organic EL device obtained was observed. In addition, the organic EL device was measured for luminous efficiency, driving voltage and half life at a 5000 cd/m$^2$ of initial luminance at room temperature by DC constant current driving. The results were shown in Table 1.

Example 1-3

Production of Organic EL Device

An organic EL device was produced in the same manner as in Example 1-1, except that the following arylamine derivative (D2) was used instead of Styrylamine derivative (D1).

The color of light emitted from the organic EL device obtained was observed. In addition, the organic EL device obtained was measured for luminous efficiency, driving voltage and half life at a 5000 cd/m$^2$ of initial luminance at room temperature by DC constant current driving. The results were shown in Table 1.

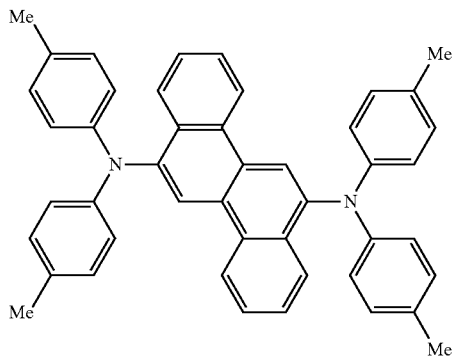

Arylamine derivative (D2)

Example 1-4

Production of Organic EL Device

An organic EL device was produced in the same manner as in Example 1-1, except that the following benzimidazole derivative (ET1) was used instead of organic metal complex (Alq) as the electron-transporting material.

The color light emitted from the organic EL device obtained was observed. In addition, the organic EL device obtained was measured for luminous efficiency, driving voltage and half life at a 5000 cd/m$^2$ of initial luminance at room temperature by DC constant current driving. The results were shown in Table 1.

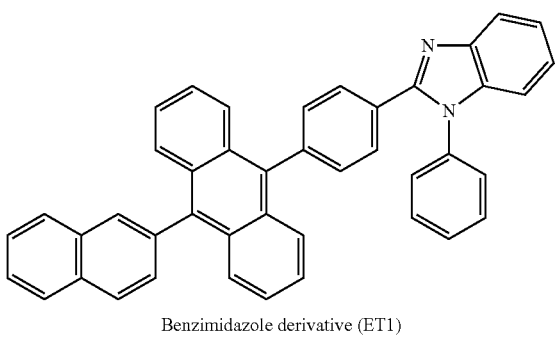 [SMILES: c1ccc(-n2c(-c3ccc(-c4c5ccccc5c(-c5ccc6ccccc6c5)c5ccccc45)cc3)nc3ccccc32)cc1]

Benzimidazole derivative (ET1)

Comparative Examples 1-1 to 1-3

Organic EL devices were produced in the same manner as in Example 1-1, except that any one of the following Comparative compounds 1 to 3 shown in Table 1 was used instead of Aromatic amine derivative (H1) as the hole-transporting material.

The color of light emitted from the organic EL device obtained was observed. In addition, the organic EL device obtained was measured for luminous efficiency, driving voltage and half life at a 5000 cd/m$^2$ of initial luminance at room temperature by DC constant current driving. The results were shown in Table 1.

Comparative compound 1

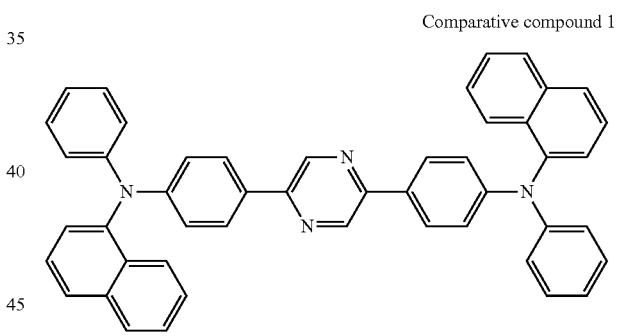

Comparative compound 2

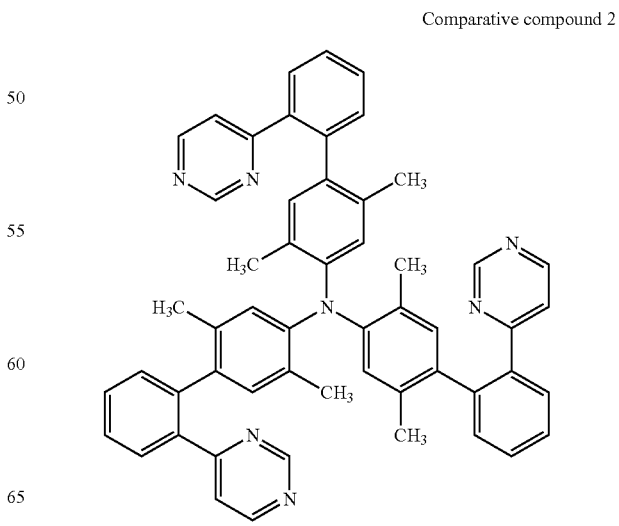

Comparative compound 3

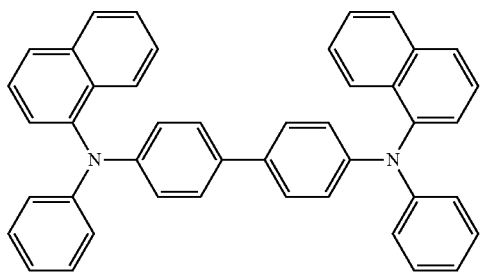

TABLE 1

|  |  | Hole-transporting material | Color of emitted light | Luminous efficiency (cd/A) | Driving voltage (V) | Half life (hour) |
|---|---|---|---|---|---|---|
| Exam. | 1-1 | H1 | Blue | 7.2 | 7.0 | 400 |
|  | 1-2 | H2 | Blue | 7.2 | 7.1 | 450 |
|  | 1-3 | H1 | Blue | 7.3 | 6.9 | 420 |
|  | 1-4 | H1 | Blue | 7.3 | 6.6 | 430 |
| Com. | 1-1 | Comparative compound 1 | Blue | 6.7 | 7.8 | 220 |
| Ex. | 1-2 | Comparative compound 2 | Blue | 6.5 | 7.9 | 160 |
|  | 1-3 | Comparative compound 3 | Blue | 6.8 | 7.0 | 210 |

As shown in Table 1, the organic EL devices using the aromatic amine derivative according to the invention could have a higher luminous efficiency at a low driving voltage and a longer device life compared with the organic EL devices using the known aromatic amine derivatives.

Example 2-1

Production of Organic EL Device

A glass substrate of 25 mm by 75 mm by 1.1 mm thick with an ITO transparent electrode (GEOMATEC CO., LTD.) was subjected to ultrasonic cleaning in isopropyl alcohol for 5 minutes, and cleaning with ultraviolet rays and ozone for 30 minutes.

The resultant substrate with transparent electrode lines was mounted on a substrate holder in a vacuum deposition device. First, the following electron-acceptor compound (C-1) was deposited to form a 5 nm-thick C-1 film so as to cover the surface of the transparent electrode on which the transparent electrode lines were formed. The following aromatic amine derivative (X1) was deposited as a first hole-transporting material on the C-1 film to form a 50 nm-thick first hole-transporting layer. Subsequent to the forming of the first hole-transporting layer, the following aromatic amine derivative (X2) was deposited as a second hole-transporting material to form a 60 nm-thick second hole-transporting layer.

Furthermore, on the second hole-transporting layer, Aromatic amine derivative (H1) obtained in Example 1 was deposited to form a 45 nm-thick emitting layer. Simultaneously, the following compound (D3) was co-deposited as a phosphorescent dopant. The concentration of Compound D3 was 8.0 mass %. This co-deposited film functioned as an emitting layer.

Following the formation of the emitting layer, the following compound (ET2) was formed to a 30 nm-thick film. The ET1 film functioned as an electron-transporting layer.

Next, LiF was formed to a 1 nm-thick film as an electron-injecting electrode (cathode) at a film forming rate of 0.1 Å/min. Metal Al was deposited on the LiF film to form a metal cathode with a thickness of 80 nm, whereby an organic EL device was fabricated.

The organic EL device obtained was measured for luminous efficiency at a 2000 cd/m² of initial luminance at room temperature by DC constant current driving. The results were shown in Table 2. In addition, the half life of the organic EL device was measured at a 5000 cd/m² of initial luminance at room temperature by DC constant current driving. The results were shown in Table 2.

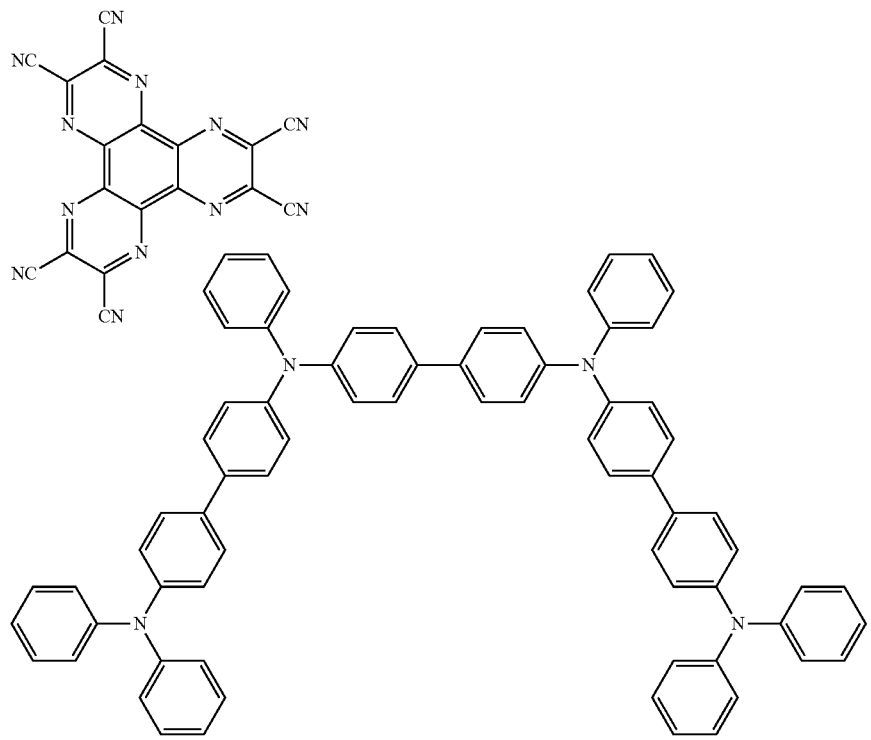

-continued

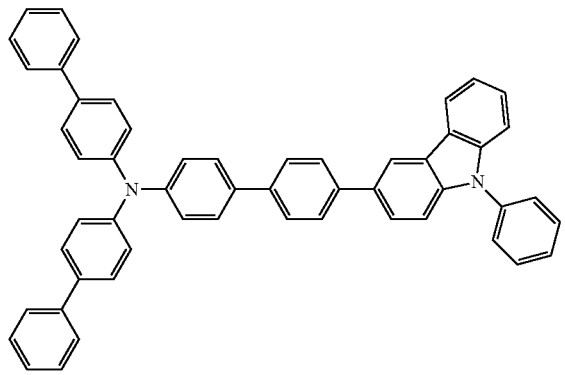
X2

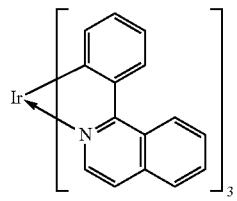
D3

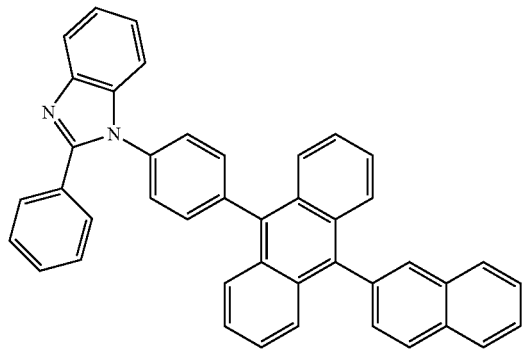
ET2

Example 2-2

Production of Organic EL Device

An organic EL device was produced in the same manner as in Example 2-1, except that Aromatic amine derivative (H2) was used instead of Aromatic amine derivative (H1) as the emitting material. The organic EL device obtained was measured for luminous efficiency at a 2000 cd/m$^2$ of initial luminance at room temperature by DC constant current driving. The results were shown in Table 2. In addition, half life of the organic EL device was measured at a 5000 cd/m$^2$ of initial luminance at room temperature by DC constant current driving. The results were shown in Table 2.

Comparative Examples 2-1 and 2-2

Production of Organic EL Devices

Organic EL devices were produced in the same manner as in Example 2-1, except that the above-mentioned Comparative compounds 1 and 2 were used instead of Aromatic amine derivative (H1) as the emitting material. The organic EL devices obtained were measured for luminous efficiency at a 2000 cd/m$^2$ of initial luminance at room temperature by DC constant current driving. The results were shown in Table 2. In addition, half life of the organic EL device was measured at a 5000 cd/m$^2$ of initial luminance at room temperature by DC constant current driving. The results were shown in Table 2.

TABLE 2

| | | Emitting material | Measurement results | | |
|---|---|---|---|---|---|
| | | | Luminous efficiency (cd/A) | Driving voltage (V) | Half life (hour) |
| Example | 2-1 | H1 | 11 | 4.2 | 400 |
| | 2-2 | H2 | 11 | 4.5 | 450 |
| Com. Ex. | 2-1 | Comparative compound 1 | 7.4 | 5.2 | 220 |
| | 2-2 | Comparative compound 2 | 7.2 | 5.3 | 160 |

As shown in Table 2, the organic EL devices using in the emitting layer the aromatic amine derivatives according to the invention could have a higher luminous efficiency and longer life compared with the organic EL devices using the comparative compounds.

INDUSTRIAL APPLICABILITY

The organic EL device of the invention can be used as a planar emitting body such as a flat panel display of a wall-hanging television, backlight of a copier, a printer or a liquid crystal display, light sources for instruments, a display panel, a navigation light, and the like.

Although only some exemplary embodiments and/or examples of this invention have been described in detail above, those skilled in the art will readily appreciated that many modifications are possible in the exemplary embodiments and/or examples without materially departing from the novel teachings and advantages of this invention. Accordingly, all such modifications are intended to be included within the scope of this invention.

The contents of the above-described documents are herein incorporated by reference in its entirety.

The invention claimed is:
1. An organic electroluminescence device comprising:
a cathode, an anode, and one or more organic thin films including an emitting layer therebetween,
wherein one or more layers of the organic thin films comprise an aromatic amine derivative represented by the following formula (1):

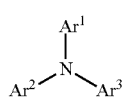

(1)

wherein one or more of $Ar^1$ to $Ar^3$ are represented by the following formula (2):

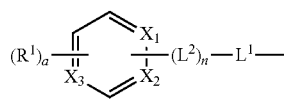

(2)

wherein $X_1$ to $X_3$ are independently a nitrogen atom or $CR^2$, provided that two of $X_1$ to $X_3$ are a nitrogen atom and $X_1$ and $X_3$ are not simultaneously a nitrogen atom,
$R^1$ is a linear or branched alkyl group having 1 to 10 carbon atoms, a cycloalkyl group having 3 to 10 ring carbon atoms, a substituted or unsubstituted silyl group, an aryl group having 6 to 50 ring carbon atoms, a heteroaryl group having 5 to 50 ring atoms, a halogen atom or a cyano group,
$R^2$ is a hydrogen atom or a group represented by $R^1$,
a is an integer of 1 to 2 and n is an integer of 0 to 3,
$L^1$ is a substituted or unsubstituted arylene group having 6 to 50 ring carbon atoms,
$L^2$ is a substituted or unsubstituted arylene group having 6 to 50 ring carbon atoms, or a substituted or unsubstituted heteroarylene group having 5 to 50 ring atoms,
$Ar^1$ to $Ar^3$ that are not the group of formula (2) are independently a substituted or unsubstituted aryl group having 6 to 50 ring carbon atoms,
when $L^1$, $L^2$ and $Ar^1$ to $Ar^3$ that are not the group of formula (2) have a substituent, the substitutes are independently a linear or branched alkyl group having 1 to 10 carbon atoms, a cycloalkyl group having 3 to 10 ring carbon atoms, a substituted or unsubstituted silyl group, an aryl group having 6 to 14 ring carbon atoms, a heteroaryl group having 5 to 20 ring atoms, a halogen atom or a cyano group,
when two or more of $Ar^1$ to $Ar^3$ are the groups of formula 2, the groups of formula (2) may be the same or different,
when a is 2, $R^1$s may be the same or different, and
when n is 2 or more, $L^2$s may be the same or different.
2. An organic electroluminescence device comprising:
a cathode, an anode, and one or more organic thin films including an emitting layer therebetween,
wherein one or more layers of the organic thin films comprise an aromatic amine derivative represented by any one of the following formulas (6) to (9):

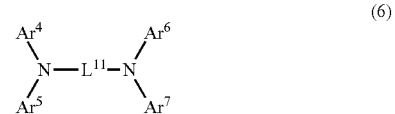

(6)

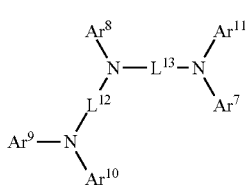

(7)

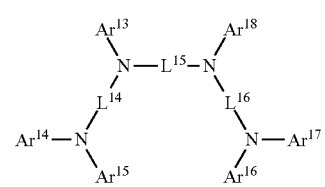

(8)

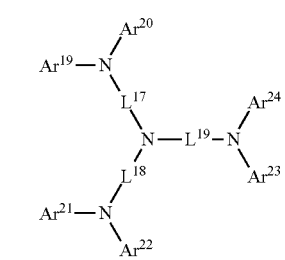

(9)

wherein one or more of $Ar^4$ to $Ar^7$ are represented by the following formula (2), one or more of $Ar^8$ to $Ar^{12}$ are represented by the following formula (2), one or more of $Ar^{13}$ to $Ar^{18}$ are represented by the following formula (2), and one or more of $Ar^{19}$ to $Ar^{24}$ are represented by the following formula (2),

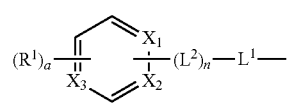

(2)

wherein $X_1$ to $X_3$ are independently a nitrogen atom or $CR^2$, provided that two of $X_1$ to $X_3$ are a nitrogen atom and $X_1$ and $X_3$ are not simultaneously a nitrogen atom,
$R^1$ is a linear or branched alkyl group having 1 to 10 carbon atoms, a cycloalkyl group having 3 to 10 ring carbon atoms, a substituted or unsubstituted silyl group, an aryl group having 6 to 50 ring carbon atoms, a heteroaryl group having 5 to 50 ring atoms, a halogen atom or a cyano group,
$R^2$ is a hydrogen atom or a group represented by $R^1$,
a is an integer of 1 to 2 and n is an integer of 0 to 3,
$L^1$ is a substituted or unsubstituted arylene group having 6 to 50 ring carbon atoms,
$L^2$ is a substituted or unsubstituted arylene group having 6 to 50 ring carbon atoms, or a substituted or unsubstituted heteroarylene group having 5 to 50 ring atoms,
the substituents of $L^1$ and $L^2$ are independently a linear or branched alkyl group having 1 to 10 carbon atoms, a cycloalkyl group having 3 to 10 ring carbon atoms, a substituted or unsubstituted silyl group, an aryl group having 6 to 14 ring carbon atoms, a halogen atom or a cyano group, $Ar^4$ to $Ar^{24}$ that are not the group of formula (2) are independently a substituted or unsubstituted aryl group having 6 to 50 ring carbon atoms, $L^{11}$ to $L^{19}$ are independently a substituted or unsubstituted arylene group having 6 to 50 ring carbon atoms, when $Ar^4$ to $Ar^{24}$ that are not the group of formula (2) and $L^{11}$ to $L^{19}$ have a substituted group, the substitutes are independently a linear or branched alkyl group having 1 to 10 carbon atoms, a cycloalkyl group having 3 to 10 ring carbon atoms, a substituted or unsubstituted silyl group, an aryl group having 6 to 14 ring carbon atoms, a heteroaryl group having 5 to 20 ring atoms, a halogen atom or a cyano group, when two or more of $Ar^4$ to $Ar^7$, $Ar^8$ to $Ar^{12}$, $Ar^{13}$ to $Ar^{18}$, or $Ar^{19}$ to $Ar^{24}$ are the groups of formula (2), the groups of formula (2) may be the same or different, when a is 2, $R^1$s may be the same or different, and when n is 2 or more, $L^2$s may be the same or different.

3. The organic electroluminescence device according to claim 1, wherein one or more layers of the organic thin films are a hole transporting layer and/or hole injecting layer, and the aromatic amine derivative is contained in one or more of the hole transporting layer and hole injecting layer.

4. The organic electroluminescence device according to claim 2, wherein one or more layers of the organic thin films are a hole transporting layer and/or hole injecting layer, and the aromatic amine derivative is contained in one or more of the hole transporting layer and hole injecting layer.

5. The organic electroluminescence device according to claim 3, wherein the aromatic amine derivative is contained in one or more of the hole transporting layer and hole injecting layer as the main component.

6. The organic electroluminescence device according to claim 4, wherein the aromatic amine derivative is contained in one or more of the hole transporting layer and hole injecting layer as the main component.

7. The organic electroluminescence device according to claim 3, wherein a layer contacting the anode of the hole injecting layer and/or hole transporting layer comprises an acceptor material.

8. The organic electroluminescence device according to claim 4, wherein a layer contacting the anode of the hole injecting layer and/or hole transporting layer comprises an acceptor material.

9. The organic electroluminescence device according to claim 1, wherein the aromatic amine derivative is contained in one or more emitting layers.

* * * * *